US007473699B2

(12) United States Patent
Gravestock et al.

(10) Patent No.: US 7,473,699 B2
(45) Date of Patent: *Jan. 6, 2009

(54) 3-CYCLYL-5-(NITROGEN-CONTAINING 5-MEMBERED RING)METHYL-OXAZOLIDINONE DERIVATIVES AND THEIR USE AS ANTIBACTERIAL AGENTS

(75) Inventors: Michael Barry Gravestock, Waltham, MA (US); Neil James Hales, Maccleslesfield (GB); Folkert Reck, Waltham, MA (US); Fei Zhou, Waltham, MA (US); Paul Robert Fleming, Waltham, MA (US); Daniel Robert Carcanague, Waltham, MA (US); Marc Michel Girardot, Atlanta, GA (US)

(73) Assignee: AstraZeneca AB, Sodertalje (SE)

( * ) Notice: Subject to any disclaimer, the term of this patent is extended or adjusted under 35 U.S.C. 154(b) by 374 days.

This patent is subject to a terminal disclaimer.

(21) Appl. No.: 10/506,020

(22) PCT Filed: Feb. 25, 2003

(86) PCT No.: PCT/GB03/00785

§ 371 (c)(1),
(2), (4) Date: Aug. 26, 2004

(87) PCT Pub. No.: WO03/072575

PCT Pub. Date: Sep. 4, 2003

(65) Prior Publication Data
US 2005/0119292 A1 Jun. 2, 2005

Related U.S. Application Data

(60) Provisional application No. 60/360,957, filed on Feb. 28, 2002.

(51) Int. Cl.
A61K 31/42 (2006.01)
C07D 263/00 (2006.01)
(52) U.S. Cl. ...................... 514/376; 548/229
(58) Field of Classification Search ........... 514/376; 548/229
See application file for complete search history.

(56) References Cited

U.S. PATENT DOCUMENTS 3,687,965 A * 8/1972 Fauran et al. ............. 548/229
7,199,143 B2 * 4/2007 Gravestock et al. ......... 514/376

FOREIGN PATENT DOCUMENTS

| EP | 0 184 170 A2 | 11/1985 |
| WO | WO-95/07271 A1 | 3/1995 |
| WO | WO-97/14690 A1 | 4/1997 |
| WO | WO-97/27188 A1 | 7/1997 |
| WO | WO-97/30995 A1 | 8/1997 |

(Continued)

OTHER PUBLICATIONS

U.S. Appl. No. 10/505,902.*

(Continued)

*Primary Examiner*—Rei-tsang Shiao
*Assistant Examiner*—Susannah Chung
(74) *Attorney, Agent, or Firm*—Morgan, Lewis & Bockius LLP

(57) ABSTRACT

Compounds of the formula (I), or a pharmaceutically-acceptable salt, or an in-vivo-hydrolysable ester thereof,

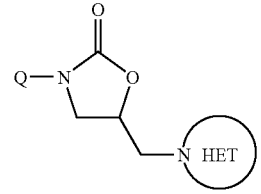

(I)

wherein —N-HET is, for example, (Ic) or (If)

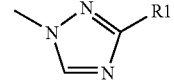

(Ic)

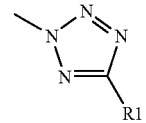

(If)

wherein R1 is (1-4C)alkyl;
Q is selected from, for example, Q1

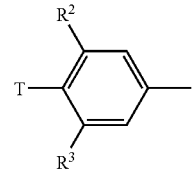

Q1 wherein $R^2$ and $R^3$ are independently hydrogen or fluoro;
T is selected from a range of groups, for example,

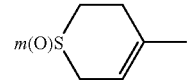

(TC12b)

wherein m is 0, 1 or 2; are useful as antibacterial agents; and processes for their manufacture and pharmaceutical compositions containing them are described.

7 Claims, No Drawings

FOREIGN PATENT DOCUMENTS

| | | | |
|---|---|---|---|
| WO | WO-97/31917 | A1 | 9/1997 |
| WO | WO-97/43280 | A1 | 11/1997 |
| WO | WO-98/01446 | A1 | 1/1998 |
| WO | WO-98/01447 | A1 | 1/1998 |
| WO | WO-99/10342 | A1 | 3/1999 |
| WO | WO-99/10343 | A1 | 3/1999 |
| WO | WO-99/11642 | A1 | 3/1999 |
| WO | WO-99/28317 | A1 | 6/1999 |
| WO | WO-99/64416 | A2 | 12/1999 |
| WO | WO-99/64417 | A2 | 12/1999 |
| WO | WO-00/21960 | A1 | 4/2000 |
| WO | WO-01/40222 | A1 | 6/2001 |
| WO | WO-01/40236 | A2 | 6/2001 |
| WO | WO-01/58885 | A1 | 8/2001 |
| WO | WO-01/81350 | A1 | 11/2001 |
| WO | WO-02/080841 | A2 | 10/2002 |
| WO | WO-02/081468 | A1 | 10/2002 |
| WO | WO-02/081469 | A1 | 10/2002 |
| WO | WO-02/081470 | A1 | 10/2002 |
| WO | WO-02/096890 | A2 | 12/2002 |
| WO | WO-02/096916 | A1 | 12/2002 |
| WO | WO-02/096917 | A1 | 12/2002 |
| WO | WO-02/096918 | A1 | 12/2002 |
| WO | WO-03/022824 | A1 | 3/2003 |
| WO | WO-03/022840 | A1 | 3/2003 |
| WO | WO-03/035073 | A1 | 5/2003 |
| WO | WO-03/035648 | A1 | 5/2003 |
| WO | WO-2004/048350 | A2 | 6/2004 |
| WO | WO-2004/048370 | A1 | 6/2004 |
| WO | WO-2004/048392 | A1 | 6/2004 |
| WO | WO-2004/056816 | A1 | 7/2004 |
| WO | WO-2004/056817 | A1 | 7/2004 |
| WO | WO-2004/056818 | A1 | 7/2004 |
| WO | WO-2004/056819 | A1 | 7/2004 |
| WO | WO-2004/078753 | A1 | 9/2004 |
| WO | WO-2004/083205 | A1 | 9/2004 |
| WO | WO-2004/083206 | A1 | 9/2004 |

OTHER PUBLICATIONS

Bundgaard, H., "Design of prodrugs: Bioreversible derivatives for various functional groups and chemical entities," In Design of Prodrugs, Bundgaard, H., eds. (Elsevier Science Publishers B.V.), pp. 1-92 (1985).

Gregory, W.A., et al., "Antibacterials. Synthesis and Structure-Activity Studies of 3-Aryl-2-oxooxazolidines. 1. The "B" Group," J. Med. Chem., 32:1673-1681 (1989).

Phillips, O.A., et al., "Synthesis and Antibacterial Activity of 5-Substituted Oxazolidinones," Bioorganic & Medicinal Chemistry, 11:35-41 (2003).

Reck, F., et al., "Novel (5R)-1,2,3-Triazolylmethyl Oxazolidinones: 4-Substituted 1,2,3-Triazoles as Antibacterial Agents with Reduced Activity against Monoamine Oxidase A," Poster at ICAAC 2004.

* cited by examiner

3-CYCLYL-5-(NITROGEN-CONTAINING 5-MEMBERED RING)METHYL-OXAZOLIDINONE DERIVATIVES AND THEIR USE AS ANTIBACTERIAL AGENTS

RELATED APPLICATIONS

This application is a national stage filing under 35 U.S.C. 371 of International Application No. PCT/GB03/00785, filed Feb. 25, 2003, which claims the benefit of U.S. Provisional Application No. 60/360,957, filed Feb. 28, 2002, both of which are hereby incorporated by reference in their entirety. International Application PCT/GB03/00785 was published under PCT Article 21(2) in English.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as principally effective against Gram-positive pathogens.

Gram-positive pathogens, for example Staphylococci, Enterococci, and Streptococci are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with various toxicities including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H.influenzae* and *M.catarrhalis*.

Certain antibacterial compounds containing an oxazolidinone ring have been described in the art (for example, Walter A. Gregory et al in J. Med. Chem. 1990, 33, 2569-2578 and Chung-Ho Park et al in J. Med. Chem. 1992, 35, 1156-1165). Such antibacterial oxazolidinone compounds with a 5-acetamidomethyl side-chain may be subject to mammalian peptidase metabolism. Furthermore, bacterial resistance to known antibacterial agents may develop, for example, by (i) the evolution of active binding sites in the bacteria rendering a previously active pharmacophore less effective or redundant, (ii) the evolution of means to chemically deactivate a given pharmacophore and/or (iii) the development and/or up-regulation of efflux mechanisms. Therefore, there remains an ongoing need to find new antibacterial agents with a favourable pharmacological profile, in particular for compounds containing new pharmacophores.

Additionally, certain antibacterial compounds containing an oxazolidinone ring have activity against the enzyme mono-amine oxidase (MAO), for instance compounds with amidomethyl or hydroxymethyl side chains at C-5 of the oxazolidinone ring. This may potentially lead to undesirable properties such as elevation in blood pressure when administered to a patient, or potentially cause drug-drug interactions. Therefore, there remains an ongoing need to find new antibacterial agents of the oxazolidinone class with a more favourable profile against MAO.

We have discovered a new class of antibiotic compounds containing an oxazolidinone ring substituted by a 5-azolylmethyl moiety in which the azole group is linked via a nitrogen atom and is itself further substituted. These compounds have useful activity against Gram-positive pathogens including MRSA and MRCNS and, in particular, against various strains exhibiting resistance to vancomycin and against *E. faecium* strains resistant to both aminoglycosides and clinically used β-lactams, but also to certain fastidious Gram negative strains such as *H.influenzae*, *M.catarrhalis* and chlamydial strains. The compounds of the invention also show a favourable, decreased, MAO potency compared with other oxazolidinone analogues, for example those with an unsubstituted 5-azolylmethyl moiety, from the prior art.

Accordingly the present invention provides a compound of the formula (I), or a pharmaceutically-acceptable salt, or an in-vivo-hydrolysable ester thereof,

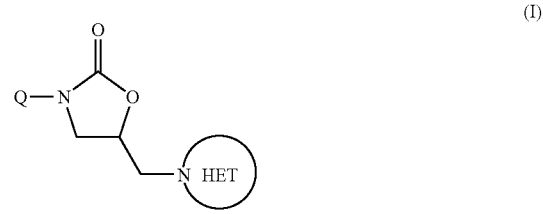

(I)

wherein —N-HET is selected from the structures (Ia) to (If) below:—

(Ia)

(Ib)

(Ic)

(Id)

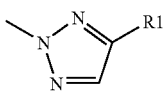
(Ie)

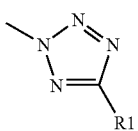
(If)

wherein u and v are independently 0 or 1;
R1 is a (1-4C)alkyl group;
Q is selected from Q1 to Q6:

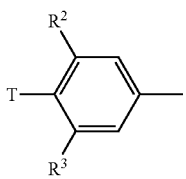
Q1

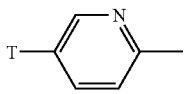
Q2

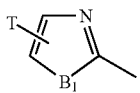
Q3

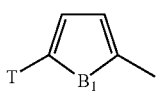
Q4

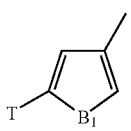
Q5

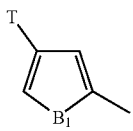
Q6 wherein $R^2$ and $R^3$ are independently selected from H, F, Cl, $CF_3$, OMe, SMe, Me and Et;
wherein $B_1$ is O or S;
wherein T is selected from the groups in (TA) to (TE) below (wherein AR1, AR2, AR2a, AR2b, AR3, AR3a, AR3b, AR4, AR4a, CY1 and CY2 are defined hereinbelow);

(TA) T is selected from the following groups:—
(TAa) AR1 or AR3; or
(TAb) a group of formula (TAb1) to (TAb6):—

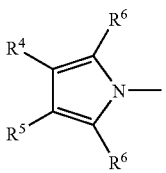
(TAb1)

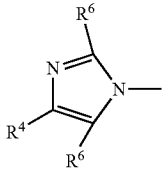
(TAb2)

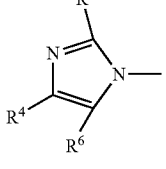
(TAb3)

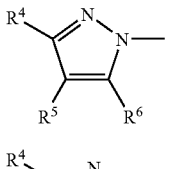
(TAb4)

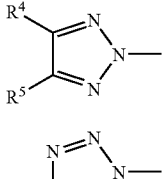
(TAb5)

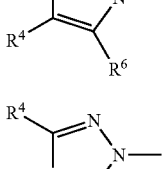
(TAb6)

wherein:
$R^6$ is selected (independently where appropriate) from hydrogen, (1-4C)alkyl, (1-4C)alkoxycarbonyl, (1-4C)alkanoyl, carbamoyl and cyano;
$R^4$ and $R^5$ are independently selected from hydrogen, halo, trifluoromethyl, cyano, azido, nitro, (1-4C)alkoxy, (1-4C)alkylS(O)$_q$— (q is 0, 1 or 2), (1-4C)alkanoyl, (1-4C)alkoxycarbonyl, benzyloxy-(1-4C)alkyl, (2-4C)alkanoylamino, hydroxyimino, (1-4C)alkoxyimino, —CONRcRv and —NRcRv wherein any (1-4C)alkyl group contained in the preceding values for $R^4$ and $R^5$ is optionally substituted by up to three substituents independently selected from hydroxy or azido (neither of such substituents on C1 of an alkoxy group, and excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1 or 2), (1-4C)alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;
$R^4$ and $R^5$ may further be independently selected from (1-4C)alkyl {optionally substituted by up to three substituents independently selected from hydroxy or azido (both of such substituents excluded from geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1 or 2), (1-4C)alkylSO$_2$—NRv-, (1-4C)alkoxycarbonyl, —CONRcRv, and —NRcRv (excluding geminal disubstitution); wherein Rv is hydrogen or (1-4C)alkyl}; Rc is as hereinafter defined; and wherein any (1-4C)alkyl group contained in the immediately preceding optional substituents (when $R^4$ and $R^5$ are independently (1-4C)alkyl) is itself optionally substituted by up to three substituents independently selected from hydroxy (not on C1 of an alkoxy group, and excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1 or 2), (1-4C)alkylSO$_2$—NRv-, (1-4C)alkoxycarbonyl, —CONRcRv, and —NRcRv (not on C1 of an alkoxy group, and excluding geminal disubstitution); wherein Rv is hydrogen or (1-4C)alkyl and Rc is as hereinafter defined;

or $R^4$ is selected from one of the groups in (TAba) to (TAbc) below, or (where appropriate) one of $R^4$ and $R^5$ is selected from the above list of $R^4$ and $R^5$ values, and the other is selected from one of the groups in (TAba) to (TAbc) below:—

(TAba) a group of the formula (TAba1)

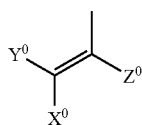

(TAba1)

wherein $Z^0$ is hydrogen or (1-4C)alkyl;

$X^0$ and $Y^0$ are independently selected from hydrogen, (1-4C)alkyl, (1-4C)alkoxycarbonyl, halo, cyano, nitro, (1-4C)alkylS(O)$_q$— (q is 0, 1 or 2), RvRwNSO$_2$—, trifluoromethyl, pentafluoroethyl, (1-4C)alkanoyl and —CONRvRw [wherein Rv is hydrogen or (1-4C)alkyl;

Rw is hydrogen or (1-4C)alkyl]; or one of $X^0$ and $Y^0$ is selected from the above list of $X^0$ and $Y^0$ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAba) may be optionally substituted by up to three substituents independently selected from (1-4C)alkyl, cyano, trifluoromethyl, nitro, halo and (1-4C)alkylsulfonyl;

(TAbb) an acetylene of the formula —≡—H or —≡-(1-4C)alkyl;

(TAbc) —$X^1$—$Y^1$-AR2, —$X^1$—$Y^1$-AR2a, —$X^1$—$Y^1$-AR2b, —$X^1$—$Y^1$-AR3, —$X^1$—$Y^1$-AR3a or —$X^1$—$Y^1$-AR3b;

wherein $X^1$ is a direct bond or —CH(OH)— and $Y^1$ is —(CH$_2$)$_m$—, —(CH$_2$)$_n$—NH—(CH$_2$)$_m$—, —CO—(CH$_2$)$_m$, —CONH—(CH$_2$)$_m$—, —C(=S)NH—(CH$_2$)$_m$— or —C(=O)O—(CH$_2$)$_m$—;

or wherein $X^1$ is —(CH$_2$)$_n$— or —CH(Me)-(CH$_2$)$_m$— and $Y^1$ is —(CH$_2$)$_m$—NH—(CH$_2$)$_m$, —CO—(CH$_2$)$_m$—, —CONH—(CH$_2$)$_m$, —C(=S)NH—(CH$_2$)$_m$—, —C(=O)O—(CH$_2$)$_m$— or —S(O)$_q$—(CH$_2$)$_m$—;

or wherein $X^1$ is —CH$_2$O—, —CH$_2$NH— or —CH$_2$N((1-4C)alkyl)- and $Y^1$ is —CO—(CH$_2$)$_m$, —CONH—(CH$_2$)$_m$— or —C(=S)NH—(CH$_2$)$_m$—; and additionally $Y^1$ is —SO$_2$— when $X^1$ is —CH$_2$NH— or —CH$_2$N((1-4C)alkyl)-, and $Y^1$ is —(CH$_2$)$_m$— when $X^1$ is —CH$_2$O— or —CH$_2$N((1-4C)alkyl)-; wherein n is 1, 2 or 3; m is 0, 1, 2 or 3 and q is 0, 1 or 2; and when $Y^1$ is —(CH$_2$)$_m$—NH—(CH$_2$)$_m$— each m is independently selected from 0, 1, 2 or 3; or (TB) T is selected from halo, formyl or —NRv$^1$Rw$^1$; or is selected from the following groups:

(TBa) $R^{10}$CO—, $R^{10}$S(O)$_q$— (q is 0, 1 or 2) or $R^{10}$CS— wherein $R^{10}$ is selected from the following groups:—

(TBaa) CY1 or CY2;

(TBab) (1-4C)alkoxycarbonyl, trifluoromethyl, —NRvRw, ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl or 2-(AR2)ethenyl; or (TBac) (1-4C)alkyl {optionally substituted by one or more groups each independently selected from hydroxy, (1-4C)alkoxy, (1-4C)alkanoyl, cyano, halo, trifluoromethyl, (1-4C)alkoxycarbonyl, —NRvRw, (1-6C)alkanoylamino, (1-4C)alkoxycarbonylamino, N-(1-4C)alkyl-N-(1-6C)alkanoylamino, (1-4C)alkylS(O)$_q$— (q is 0, 1 or 2), CY1, CY2, AR1, (1-4C)alkylS(O)$_p$NH— or (1-4C)alkylS(O)$_p$-((1-4C)alkyl)N—(p is 1 or 2)}; wherein Rv is hydrogen or (1-4C)alkyl; Rw is hydrogen or (1-4C)alkyl; Rv$^1$ is hydrogen, (1-4C)alkyl or (3-8C)cycloalkyl; Rw$^1$ is hydrogen, (1-4C)alkyl, (3-8C)cycloalkyl, formyl, (1-4C)alkyl-CO— or (1-4C)alkylS(O)$_q$— (q is 1 or 2); or (TC) T is selected from a group of formula (TC1) to (TC4):—

(TC1)

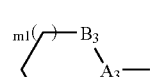

(TC2)

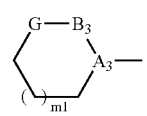

(TC3)

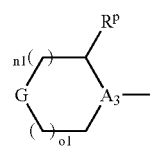

(TC4)

wherein in (TC1): >A$_3$-B$_3$— is >C(Rq)-CH(Rr)- or >N—CH$_2$— and G is —O—, —S—, —SO—, —SO$_2$— or >N(Rc);

wherein in (TC2): m1 is 0, 1 or 2; >A$_3$-B$_3$— is >C=C(Rr)- or > C(Rq)-CH(Rr)- or >N—CH$_2$— and G is —O—, —S—, —SO—, —SO$_2$— or >N(Rc);

wherein in (TC3): m1 is 0, 1 or 2; >A$_3$-B$_3$— is >C(Rq)-CH(Rr)- (other than when Rq and Rr are both together hydrogen) or >N—CH$_2$— and G is —O—, —S—, —SO—, —SO$_2$— or >N(Rc);

wherein in (TC4): n1 is 1 or 2; o1 is 1 or 2 and n1+o1=2 or 3; >A₃-B₃— is >C=C(Rr)- or >C(Rq)-CH(Rr)- or >N—CH₂— and G is —O—, —S—, —SO—, —SO₂— or >N(Rc); Rp is hydrogen, (1-4C)alkyl (other than when such substitution is defined by >A₃-B₃—), hydroxy, (1-4C)alkoxy or (1-4C)alkanoyloxy;

wherein in (TC1), (TC2) and (TC4); m1, n1 and o1 are as defined hereinbefore in (TC): >A₃-B₃— is >N—CH₂— and G is >C(R¹¹)(R¹²), >C=O, >C—OH, >C—(1-4C)alkoxy, >C=N—OH, >C=N-(1-4C)alkoxy, >C=N—NH-(1-4C)alkyl, C=N—N((1-4C)alkyl)₂ (the last two (1-4C)alkyl groups above in G being optionally substituted by hydroxy) or >C=N—N—CO-(1-4C)alkoxy; wherein > represents two single bonds;

Rq is hydrogen, hydroxy, halo, (1-4C)alkyl or (1-4C)alkanoyloxy;

Rr is (independently where appropriate) hydrogen or (1-4C)alkyl;

R¹¹ is hydrogen, (1-4C)alkyl, fluoro(1-4C)alkyl, (1-4C)alkyl-thio-(1-4C)alkyl or hydroxy-(1-4C)alkyl and R¹² is —[C(Rr)(Rr)]ₘ—N(Rr)(Rc) wherein m2 is 0, 1 or 2;

and, other than the ring substitution defined by G, >A₃-B₃— and Rp, each ring system may be optionally further substituted on a carbon atom not adjacent to the link at >A₃- by up to two substituents independently selected from (1-4C)alkyl, fluoro(1-4C)alkyl (including trifluoromethyl), (1-4C)alkyl-thio-(1-4C)alkyl, hydroxy-(1-4C)alkyl, amino, amino-(1-4C)alkyl, (1-4C)alkanoylamino, (1-4C)alkanoylamino-(1-4C)alkyl, carboxy, (1-4C)alkoxycarbonyl, ARc-oxymethyl, ARc-thiomethyl, oxo (=O) (other than when G is >N-Rc and Rc is group (Rc2) defined hereinbefore) or independently selected from Rc (if such substituents are not already defined herein in (TC)); and also hydroxy or halo (the last two optional substituents only when G is —O— or —S—);

wherein ARc is selected from AR1, AR2, AR2a, AR2b, CY1 and CY2 defined hereinafter and Rc is selected from groups (Rc 1) to (Rc5) defined hereinafter; or (TD) T is selected from the following groups:—

(TDa) a bicyclic spiro-ring system of formula (TDa1) to (TDa9):—

(TDa1)

(TDa2)

(TDa3)

(TDa4)

(TDa5)

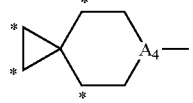
(TDa6)

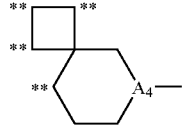
(TDa7)

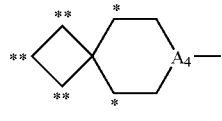
(TDa8)

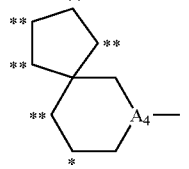
(TDa9)

wherein;

(i) the A₄ linking group is a nitrogen atom or an sp³ or sp² carbon atom (with the double bond, where appropriate, orientated in either direction); and (ii) one of the ring carbon atoms at positions marked * and ** is replaced by one of the following groups —NRc-, >CH—NHRc, >CH—NRc-(1-4C)alkyl, >CH—CH₂—NHRc, >CH—CH₂—NRc-(1-4C)alkyl [wherein a central —CH₂— chain link is optionally mono- or di-substituted by (1-4C)alkyl]; with the provisos that positions marked * are not replaced by —NH— in the ring containing the A₄ link when A₄ is a nitrogen atom or an sp² carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1-4C)alkyl, fluoro(1-4C)alkyl (including trifluoromethyl), (1-4C)alkyl-thio-(1-4C)alkyl, hydroxy-(1-4C)alkyl, amino, amino-(1-4C)alkyl, (1-4C)alkanoylamino, (1-4C)alkanoylamino-(1-4C)alkyl, carboxy, (1-4C)alkoxycarbonyl, AR2-oxymethyl, AR2-thiomethyl, oxo (=O) (other than when the ring contains an >N-Rc and Rc is group (Rc2)) and also hydroxy or halo; and Rc is selected from groups (Rc1) to (Rc5) defined hereinafter; or (TDb) a 7-, 8- or 9-membered bicyclic ring system containing a bridge of 0, 1 or 2 carbon atoms of formula (TDb1) to (TDb14):—

7-membered ring skeletons

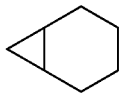

[4, 1, 0]

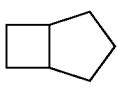

[3, 2, 0]

[3, 1, 1]

[2, 2, 1]

8-membered ring skeletons

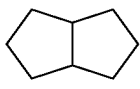

[3, 3, 0]

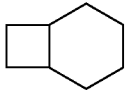

[4, 2, 0]

[4, 1, 1]

[3, 2, 1]

[2, 2, 2]

9-membered ring skeletons (TDb1)
(TDb2)
(TDb3)
(TDb4)
(TDb5)
(TDb6)
(TDb7)
(TDb8)
(TDb9)

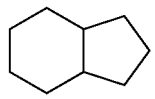

[4, 3, 0]

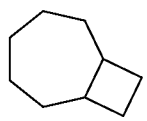

[5, 2, 0]

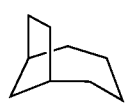

[4, 2, 1]

[3, 3, 1]

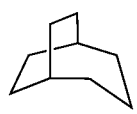

[3, 2, 2]

(TDb10)
(TDb11)
(TDb12)
(TDb13)
(TDb14)

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring sp$^3$ or sp$^2$ carbon atom (with the double bond, where appropriate, orientated in either direction) from any position in either ring [other than from a bridgehead position or from an sp$^2$ carbon atom in the 4-membered ring in (TDb2), (TDb6) and (TDb11)];

(iii) one of the ring carbon atoms at a position not adjacent to the linking position, is replaced (other than when the ring contains an O or S heteroatom) by one of the following groups —NRc-[not at a bridgehead position], >C(H)—NHRc, >C(H)—NRc-(1-4C)alkyl, >C(H)—CH$_2$—NHRc, >C(H)—CH$_2$—NRc-(1-4C)alkyl [wherein the hydrogen atom shown in brackets is not present when the replacement is made at a bridgehead position and wherein a central —CH$_2$— chain link is optionally mono- or di-substituted by (1-4C)alkyl]; with the proviso that when the ring system is linked via a ring nitrogen atom or an sp$^2$ carbon atom any replacement of a ring carbon atom by —NRc-, O or S is at least two carbon atoms away from the linking position; and (iv) the ring system is optionally (further) substituted on an available ring carbon atom as for the bicyclic spiro-ring systems described in (TDa); and Rc is selected from groups (Rc1) to (Rc5) defined hereinafter; or (TE) T is selected from the following groups (TE1) to (TE3):—

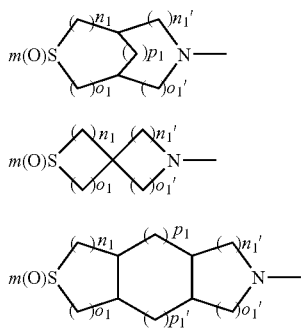

wherein m is 0, 1 or 2; and ( )$n_1$, ( )$o_1$, ( )$n_{1'}$, ( )$o_{1'}$, ( )$p_1$ and ( )$p_{1'}$ represent chains of carbon atoms (optionally substituted as defined for AR1 hereinafter) of length $n_1$, $o_1$, $n_{1'}$, $o_{1'}$, $p_1$ and $p_{1'}$ respectively, and are independently 0-2, with the proviso that in (TE1) and (TE2) the sum of $n_1$, $o_1$, $n_{1'}$ and $o_{1'}$ does not exceed 8 (giving a maximum ring size of 14 in (TE1) and 11 in (TE2)), and in (TE3) the sum of $n_1$, $o_1$, $n_{1'}$, $o_{1'}$, $p_1$ and $p_{1'}$ does not exceed 6 (giving a maximum ring size of 12);

wherein Rc is selected from groups (Rc1) to (Rc5):—

(Rc1) (1-6C)alkyl {optionally substituted by one or more (1-4C)alkanoyl groups (including geminal disubstitution) and/or optionally monosubstituted by cyano, (1-4C)alkoxy, trifluoromethyl, (1-4C)alkoxycarbonyl, phenyl (optionally substituted as for AR1 defined hereinafter), (1-4C)alkylS(O)$_q$— (q is 0, 1 or 2); or, on any but the first carbon atom of the (1-6C)alkyl chain, optionally substituted by one or more groups (including geminal disubstitution) each independently selected from hydroxy and fluoro, and/or optionally monosubstituted by oxo, —NRvRw [wherein Rv is hydrogen or (1-4C)alkyl; Rw is hydrogen or (1-4C)alkyl], (1-6C)alkanoylamino, (1-4C)alkoxycarbonylamino, N-(1-4C)alkyl-N-(1-6C)alkanoylamino, (1-4C)alkylS(O)$_p$NH— or (1-4C)alkylS(O)$_p$—((1-4C)alkyl)N-(p is 1 or 2)};

(Rc2) formyl, $R^{13}$CO—, $R^{13}SO_2$— or $R^{13}$CS— wherein $R^{13}$ is selected from (Rc2a) to (Rc2e):—

(Rc2a) AR1, AR2, AR2a, AR2b, AR3, AR3a, AR3b, AR4, AR4a, CY1, CY2;

(Rc2b) (1-4C)alkoxycarbonyl, trifluoromethyl, —NRvRw [wherein Rv is hydrogen or (1-4C)alkyl; Rw is hydrogen or (1-4C)alkyl], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, 2-(AR2)ethenyl, 2-(AR2a)ethenyl;

(Rc2c) (1-10C)alkyl {optionally substituted by one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkanoyl, carboxy, phosphoryl [—O—P(O)(OH)$_2$, and mono- and di-(1-4C)alkoxy derivatives thereof], phophoryl [—O—P(OH)$_2$ and mono- and di-(1-4C)alkoxy derivatives thereof], and amino; and/or optionally substituted by one group selected from phosphonate [phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$-[the (1-4C)alkyl group of (1-4C)alkylS(O)$_q$— being optionally substituted by one substituent selected from hydroxy, (1-4C)alkoxy, (1-4C)alkanoyl, phosphoryl [—O—P(O)(OH)$_2$, and mono- and di-(1-4C)alkoxy derivatives thereof], phophoryl [—O—P(OH)$_2$ and mono- and di-(1-4C)alkoxy derivatives thereof], amino, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, carboxy, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$—((1-4C)alkyl)N—, (1-4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};

(Rc2d) $R^{14}$C(O)O(1-6C)alkyl wherein $R^{14}$ is AR1, AR2, (1-4C)alkylamino (the (1-4C)alkyl group being optionally substituted by (1-4C)alkoxycarbonyl or by carboxy), benzyloxy-(1-4C)alkyl or (1-10C)alkyl {optionally substituted as defined for (Rc2c)};

(Rc2e) $R^{15}$O— wherein $R^{15}$ is benzyl, (1-6C)alkyl {optionally substituted as defined for (Rc2c)}, CY1, CY2 or AR2b;

(Rc3) hydrogen, cyano, 2-cyanoethenyl, 2-cyano-2-((1-4C)alkyl)ethenyl, 2-((1-4C)alkylaminocarbonyl)ethenyl, 2-((1-4C)alkoxycarbonyl)ethenyl, 2-nitroethenyl, 2-nitro-2-((1-4C)alkyl)ethenyl, 2-(AR1)ethenyl, 2-(AR2)ethenyl, or of the formula (Rc3a)

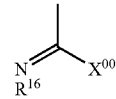

(Rc3a)

wherein $X^{00}$ is —OR$^{17}$, —SR$^{17}$, —NHR$^{17}$ and —N(R$^{17}$)$_2$; wherein $R^{17}$ is hydrogen (when $X^{00}$ is —NHR$^{17}$ and —N(R$^{17}$)$_2$), and $R^{17}$ is (1-4C)alkyl, phenyl or AR2 (when $X^{00}$ is —OR$^{17}$, —SR$^{17}$ and —NHR$^{17}$); and $R^{16}$ is cyano, nitro, (1-4C)alkylsulfonyl, (4-7C)cycloalkylsulfonyl, phenylsulfonyl, (1-4C)alkanoyl and (1-4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or RiNHC(Rj)=CHC(=O)— wherein Rd is (1-6C)alkyl; Re is hydrogen or (1-6C)alkyl, or Rd and Re together form a (3-4C)alkylene chain; Rf is hydrogen, (1-6C)alkyl, hydroxy(1-6C)alkyl, (1-6C)alkoxy(1-6C)alkyl, —NRvRw [wherein Rv is hydrogen or (1-4C)alkyl; Rw is hydrogen or (1-4C)alkyl], (1-6C)alkoxy, (1-6C)alkoxy(1-6C)alkoxy, hydroxy(2-6C)alkoxy, (1-4C)alkylamino(2-6C)alkoxy, di-($^{14}$C)alkylamino(2-6C)

alkoxy; Rg is (1-6C)alkyl, hydroxy or (1-6C)alkoxy; Rh is hydrogen or (1-6C)alkyl; Ri is hydrogen, (1-6C)alkyl, AR1, AR2, AR2a, AR2b and Rj is hydrogen or (1-6C) alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring;

wherein; optional substituents on AR1, AR2, AR2a, AR2b, AR3, AR3a, AR3b, AR4, AR4a, CY1 and CY2 are (on an available carbon atom) up to three substituents independently selected from (1-4C)alkyl {optionally substituted by substituents selected independently from hydroxy, trifluoromethyl, (1-4C)alkyl S(O)$_q$— (q is 0, 1 or 2), (1-4C) alkoxy, (1-4C)alkoxycarbonyl, cyano, nitro, (1-4C)alkanoylamino, —CONRvRw or —NRvRw}, trifluoromethyl, hydroxy, halo, nitro, cyano, thiol, (1-4C) alkoxy, (1-4C)alkanoyloxy, dimethylaminomethyleneaminocarbonyl, di(N-(1-4C)alkyl)aminomethylimino, carboxy, (1-4C)alkoxycarbonyl, (1-4C)alkanoyl, (1-4C) alkylSO$_2$amino, (2-4C)alkenyl {optionally substituted by carboxy or (1-4C)alkoxycarbonyl}, (2-4C)alkynyl, (1-4C) alkanoylamino, oxo (=O), thioxo (=S), (1-4C)alkanoylamino {the (1-4C)alkanoyl group being optionally substituted by hydroxy}, (1-4C)alkyl S(O)$_q$— (q is 0, 1 or 2) {the (1-4C)alkyl group being optionally substituted by one or more groups independently selected from cyano, hydroxy and (1-4C)alkoxy}, —CONRvRw or —NRvRw [wherein Rv is hydrogen or (1-4C)alkyl; Rw is hydrogen or (1-4C) alkyl];

and further optional substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1-4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1-4C) alkyl, (1-4C)alkoxyimino(1-4C)alkyl, halo-(1-4C)alkyl, (1-4C)alkanesulfonamido, —SO$_2$NRvRw [wherein Rv is hydrogen or (1-4C)alkyl;

Rw is hydrogen or (1-4C)alkyl]; and optional substituents on AR2, AR2a, AR2b, AR3, AR3a, AR3b, AR4 and AR4a are (on an available nitrogen atom, where such substitution does not result in quaternization) (1-4C)alkyl, (1-4C)alkanoyl {wherein the (1-4C)alkyl and (1-4C)alkanoyl groups are optionally substituted by (preferably one) substituents independently selected from cyano, hydroxy, nitro, trifluoromethyl, (1-4C)alkyl S(O)$_q$— (q is 0, 1 or 2), (1-4C)alkoxy, (1-4C)alkoxycarbonyl, (1-4C)alkanoylamino, —CONRvRw or —NRvRw [wherein Rv is hydrogen or (1-4C)alkyl; Rw is hydrogen or (1-4C)alkyl]}, (2-4C)alkenyl, (2-4C)alkynyl, (1-4C) alkoxycarbonyl or oxo (to form an N-oxide).

It will be noted that in the groups (Ia) to (If) there is no substituent in the position adjacent to the nitrogen link.

In this specification, where it is stated that a ring may be linked via an sp$^2$ carbon atom it is to be understood that the ring is linked via one of the carbon atoms in a C=C double bond.

In this specification the term 'alkyl' includes straight chained and branched structures. For example, (1-6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1-4C)alkyl includes 1-bromoethyl and 2-bromoethyl.

There follow particular and suitable values for certain substituents and groups which may be referred to in this specification. These values may be used where appropriate with any of the definitions and embodiments disclosed hereinbefore, or hereinafter.

Examples of (1-4C)alkyl and (1-5C)alkyl include methyl, ethyl, propyl, isopropyl and t-butyl; examples of (1-6C)alkyl include methyl, ethyl, propyl, isopropyl, t-butyl, pentyl and hexyl; examples of (1-10C)alkyl include methyl, ethyl, propyl, isopropyl, pentyl, hexyl, heptyl, octyl and nonyl; examples of (1-4C)alkanoylamino-(1-4C)alkyl include formamidomethyl, acetamidomethyl and acetamidoethyl; examples of hydroxy(1-4C)alkyl and hydroxy(1-6C)alkyl include hydroxymethyl, 1-hydroxyethyl, 2-hydroxyethyl and 3-hydroxypropyl; examples of (1-4C)alkoxycarbonyl include methoxycarbonyl, ethoxycarbonyl and propoxycarbonyl; examples of 2-((1-4C)alkoxycarbonyl)ethenyl include 2-(methoxycarbonyl)ethenyl and 2-(ethoxycarbonyl)ethenyl; examples of 2-cyano-2-((1-4C)alkyl)ethenyl include 2-cyano-2-methylethenyl and 2-cyano-2-ethylethenyl; examples of 2-nitro-2-((1-4C)alkyl)ethenyl include 2-nitro-2-methylethenyl and 2-nitro-2-ethylethenyl; examples of 2-((1-4C)alkylaminocarbonyl)ethenyl include 2-(methylaminocarbonyl)ethenyl and 2-(ethylaminocarbonyl)ethenyl; examples of (2-4C)alkenyl include allyl and vinyl; examples of (2-4C)alkynyl include ethynyl and 2-propynyl; examples of (1-4C)alkanoyl include formyl, acetyl and propionyl; examples of (1-4C)alkoxy include methoxy, ethoxy and propoxy; examples of (1-6C)alkoxy and (1-10C)alkoxy include methoxy, ethoxy, propoxy and pentoxy; examples of (1-4C)alkylthio include methylthio and ethylthio; examples of (1-4C)alkylamino include methylamino, ethylamino and propylamino; examples of di-((1-4C)alkyl)amino include dimethylamino, N-ethyl-N-methylamino, diethylamino, N-methyl-N-propylamino and dipropylamino; examples of halo groups include fluoro, chloro and bromo; examples of (1-4C)alkylsulfonyl include methylsulfonyl and ethylsulfonyl; examples of (1-4C)alkoxy-(1-4C)alkoxy and (1-6C)alkoxy-(1-6C)alkoxy include methoxymethoxy, 2-methoxyethoxy, 2-ethoxyethoxy and 3-methoxypropoxy; examples of (1-4C)alkoxy-(1-4C)alkoxy-(1-4C)alkoxy include 2-(methoxymethoxy)ethoxy, 2-(2-methoxyethoxy)ethoxy, 3-(2-methoxyethoxy)propoxy and 2-(2-ethoxyethoxy)ethoxy; examples of (1-4C)alkylS(O)$_2$amino include methylsulfonylamino and ethylsulfonylamino; examples of (1-4C)alkanoylamino and (1-6C)alkanoylamino include formamido, acetamido and propionylamino; examples of (1-4C)alkoxycarbonylamino include methoxycarbonylamino and ethoxycarbonylamino; examples of N-(1-4C)alkyl-N-(1-6C)alkanoylamino include N-methylacetamido, N-ethylacetamido and N-methylpropionamido; examples of (1-4C)alkylS(O)$_p$NH— wherein p is 1 or 2 include methylsulfinylamino, methylsulfonylamino, ethylsulfinylamino and ethylsulfonylamino; examples of (1-4C)alkylS(O)$_p$((1-4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1-4C)alkylS(O)$_p$NH— wherein p is 1 or 2 include trifluoromethylsulfinylamino and trifluoromethylsulfonylamino; examples of fluoro(1-4C)alkylS(O)$_p$((1-4C)alkyl)NH— wherein p is 1 or 2 include trifluoromethylsulfinylmethylamino and trifluoromethylsulfonylmethylamino examples of (1-4C)alkoxy(hydroxy)phosphoryl include methoxy(hydroxy)phosphoryl and ethoxy(hydroxy)phosphoryl; examples of di-(1-4C)alkoxyphosphoryl include di-methoxyphosphoryl, di-ethoxyphosphoryl and ethoxy(methoxy)phosphoryl; examples of (1-4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1-4C)alkyl include benzyloxymethyl and benzyloxyethyl; examples of a (3-4C)alkylene chain are trimethylene or tetramethylene; examples of (1-6C)alkoxy-(1-6C)alkyl include methoxymethyl, ethoxymethyl and 2-methoxyethyl; examples of hydroxy-(2-6C)alkoxy include 2-hydroxyethoxy and 3-hydroxypropoxy; examples of (1-4C)alkylamino-(2-6C)alkoxy include 2-methylaminoethoxy and 2-ethylaminoethoxy; examples of di-(1-4C)alkylamino-(2-6C)alkoxy include 2-dimethylaminoethoxy and 2-diethylaminoethoxy; examples of phenyl(1-4C)alkyl include benzyl and phenethyl; examples of (1-4C)alkylcarbamoyl include methylcarbamoyl and ethylcarbamoyl; examples of di((1-4C)alkyl)carbamoyl include di(methyl)carbamoyl and di(ethyl)carbamoyl; examples of hydroxyimino(1-4C)alkyl include hydroxyiminomethyl, 2-(hydroxyimino)ethyl and 1-(hydroxyimino)ethyl; examples of (1-4C)alkoxyimino include methoxyimino and ehtoxyimino, examples of (1-4C)alkoxyimino-(1-4C)alkyl include methoxyiminomethyl, ethoxyiminomethyl, 1-(methoxyimino)ethyl and 2-(methoxyimino)ethyl; examples of halo(1-4C)alkyl include, halomethyl, 1-haloethyl, 2-haloethyl, and 3-halopropyl; examples of nitro(1-4C)alkyl include nitromethyl, 1-nitroethyl, 2-nitroethyl and 3-nitropropyl; examples of amino(1-4C)alkyl include aminomethyl, 1-aminoethyl, 2-aminoethyl and 3-aminopropyl; examples of cyano(1-4C)alkyl include cyanomethyl, 1-cyanoethyl, 2-cyanoethyl and 3-cyanopropyl; examples of (1-4C)alkanesulfonamido include methanesulfonamido and ethanesulfonamido; examples of (1-4C)alkylaminosulfonyl include methylaminosulfonyl and ethylaminosulfonyl; and examples of di-(1-4C)alkylaminosulfonyl include dimethylaminosulfonyl, diethylaminosulfonyl and N-methyl-N-ethylaminosulfonyl; examples of (1-4C)alkanesulfonyloxy include methylsulfonyloxy, ethylsulfonyloxy and propylsulfonyloxy; examples of (1-4C)alkanoyloxy include acetoxy; examples of (1-4C)alkylaminocarbonyl include methylaminocarbonyl and ethylaminocarbonyl; examples of di((1-4C)alkyl)aminocarbonyl include dimethylaminocarbonyl and diethylaminocarbonyl; examples of (3-8C)cycloalkyl include cyclopropyl, cyclobutyl, cyclopentyl and cyclohexyl; examples of (4-7C)cycloalkyl include cyclobutyl, cyclopentyl and cyclohexyl; examples of di(N-(1-4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1-3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1-3 heteroatoms chosen from oxygen, sulfur and nitrogen. Specific examples of such ring systems include, for example, 3H-pyrrolo[1,2-a]pyrrole, pyrrolo[2,1- b]thiazole, 1H-imidazo[1,2-a]pyrrole, 1H-imidazo[1,2-a] imidazole, 1H,3H-pyrrolo[1,2-c]oxazole, 1H-imidazo[1,5-a] pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1, 2-b]pyridazine, pyrrolo[1,2-c]pyrimidine, pyrrolo[1,2-a] pyrazine, pyrrolo[1,2-a]pyrimidine, pyrido[2,1-c]-s-triazole, s-triazole[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1-c][1,4] oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8, 8a-hexahydrooxazolo[3,4a]pyridin-7-yl, (7aS)[3H,5H]-1, 7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c] oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a] quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo [1,5-a]quinoline and imidazo[5,1-a]isoquinoline.

The nomenclature used is that found in, for example, "Heterocyclic Compounds (Systems with bridgehead nitrogen), W. L. Mosby (Interscience Publishers Inc., New York), 1961, Parts 1 and 2.

Where optional substituents are listed such substitution is preferably not geminal disubstitution unless stated otherwise. If not stated elsewhere, suitable optional substituents for a particular group are those as stated for similar groups herein.

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1-4C)alkyl (including geminal disubstitution), (1-4C)alkoxy, (1-4C)alkylthio, acetamido, (1-4C)alkanoyl, cyano, trifluoromethyl and phenyl].

Preferable optional substituents on CY1 & CY2 are mono- or disubstitution by substituents independently selected from (1-4C)alkyl (including geminal disubstitution), hydroxy, (1-4C)alkoxy, (1-4C)alkylthio, acetamido, (1-4C)alkanoyl, cyano, and trifluoromethyl.

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl) amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol.

Suitable pharmaceutically-acceptable esters for carboxy include (1-6C)alkoxymethyl esters for example methoxymethyl, (1-6C)alkanoyloxymethyl esters for example pivaloyloxymethyl, phthalidyl esters, (3-8C)cycloalkoxycarbonyloxy(1-6C)alkyl esters for example 1-cyclohexylcarbonyloxyethyl; 1,3-dioxolan-2-onylmethyl esters for example 5-methyl-1,3-dioxolan-2-ylmethyl; and (1-6C)alkoxycarbonyloxyethyl esters for example 1-methoxycarbonyloxyethyl and may be formed at any carboxy group in the compounds of this invention.

Suitable pro-drugs for pyridine derivatives include acyloxymethyl pyridinium salts eg halides; for example a prodrug such as:

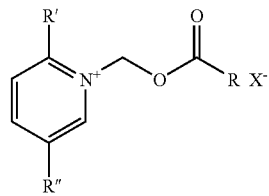

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1-10C)alkanoyl, benzoyl, phenylacetyl and substituted benzoyl and phenylacetyl, (1-10C)alkoxycarbonyl (to give alkyl carbonate esters), di-(1-4C)alkylcarbamoyl and N-(di-(1-4C)alkylaminoethyl)-N-(1-4C)alkylcarbamoyl (to give carbamates), di-(1-4C)alkylaminoacetyl, carboxy(2-5C)alkylcarbonyl and carboxyacetyl. Examples of ring substituents on phenylacetyl and benzoyl include chloromethyl or aminomethyl, (1-4C)alkylaminomethyl and di-((1-4C)alkyl)aminomethyl, and morpholino or piperazino linked from a ring nitrogen atom via a methylene linking group to the 3- or 4-position of the benzoyl ring. Other interesting in-vivo hydrolysable esters include, for example, $R^A C(O)O(1\text{-}6C)\text{alkyl-CO}$— (wherein $R^A$ is for example, optionally substituted benzyloxy-(1-4C)alkyl, or optionally substituted phenyl; suitable substituents on a phenyl group in such esters include, for example, 4-(1-4C)piperazino-(1-4C)alkyl, piperazino-(1-4C)alkyl and morpholino-(1-4C)alkyl.

Suitable in-vivo hydrolysable esters of a compound of the formula (I) are described as follows. For example, a 1,2-diol may be cyclised to form a cyclic ester of formula (PD1) or a pyrophosphate of formula (PD2), and a 1,3-diol may be cyclised to form a cyclic ester of the formula (PD3):

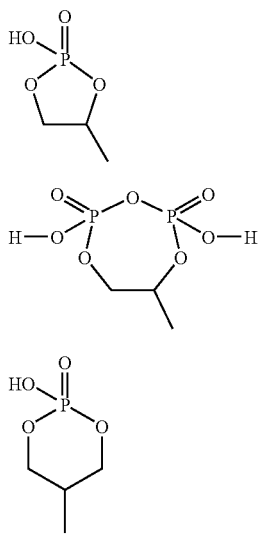

(PD1)

(PD2)

(PD3)

Esters of compounds of formula (I) wherein the HO— function/s in (PD1), (PD2) and (PD3) are protected by (1-4C) alkyl, phenyl or benzyl are useful intermediates for the preparation of such pro-drugs.

Further in-vivo hydrolysable esters include phosphoramidic esters, and also compounds of invention in which any free hydroxy group independently forms a phosphoryl (npd is 1) or phophoryl (npd is 0) ester of the formula (PD4):

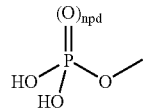

(PD4)

For the avoidance of doubt, phosphono is —P(O)(OH)$_2$; (1-4C)alkoxy(hydroxy)-phosphoryl is a mono-(1-4C)alkoxy derivative of —O—P(O)(OH)$_2$; and di-(1-4C)alkoxyphosphoryl is a di-(1-4C)alkoxy derivative of —O—P(O)(OH)$_2$.

Useful intermediates for the preparation of such esters include compounds containing a group/s of formula (PD4) in which either or both of the —OH groups in (PD1) is independently protected by (1-4C)alkyl (such compounds also being interesting compounds in their own right), phenyl or phenyl-(1-4C)alkyl (such phenyl groups being optionally substituted by 1 or 2 groups independently selected from (1-4C)alkyl, nitro, halo and (1-4C)alkoxy).

Thus, prodrugs containing groups such as (PD1), (PD2), (PD3) and (PD4) may be prepared by reaction of a compound of invention containing suitable hydroxy group/s with a suitably protected phosphorylating agent (for example, containing a chloro or dialkylamino leaving group), followed by oxidation (if necessary) and deprotection.

Other suitable prodrugs include phosphonooxymethyl ethers and their salts, for example a prodrug of R—OH such as:

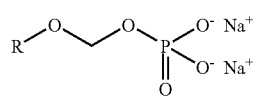

When a compound of invention contains a number of free hydroxy group, those groups not being converted into a pro-drug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2), (PD3) and/or (PD4) may ionise (partially or fully) to form salts with an appropriate number of counter-ions. Thus, by way of example, if an in-vivo hydrolysable ester prodrug of a compound of invention contains two (PD4) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the oxazolidinone ring. The pharmaceutically active enantiomer is of the formula (IA):

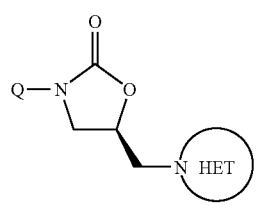

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. The enantiomer depicted above may be the 5(R) or 5(S) enantiomer depending on the nature of the N-HET group (for example, when —N-HET is imidazole it is the 5(S) enantiomer).

Furthermore, some compounds of the formula (I) may have other chiral centres, for example, certain sulfoxide compounds may be chiral at the sulfur atom. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

Furthermore, some compounds of the formula (I), for example certain sulfoxide compounds may exist as cis- and trans-isomers. It is to be understood that the invention encompasses all such isomers, and mixtures thereof, that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens, including organisms known to be resistant to most commonly used antibiotics, and to certain fastidious Gram negative strains such as *H.influenzae* and *M.catarrhalis*. They have good physical and/or pharmacokinetic properties in general, and favourable toxicological and MAO profiles.

Particularly preferred compounds of the invention comprise a compound of formula (I), or a pharmaceutically-acceptable salt or an in-vivo hydrolysable ester thereof, wherein the substituents Q, HET (which may also be described as —N-HET herein), T and other substituents mentioned above have values disclosed hereinbefore, or any of the following values (which may be used where appropriate with any of the definitions and embodiments disclosed hereinbefore or hereinafter):

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TA), (TB) and (TD) (i.e. in this embodiment T is not (TC) or (TE)).

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TC) particularly TC4.

In another embodiment of the invention are provided compounds of formula (I), or a pharmaceutically-acceptable salt or an in-vivo hydrolysable ester thereof, in which Q, HET (which may also be described as —N-HET herein) and other substituents mentioned above have the values disclosed hereinbefore, and T is as defined hereinbefore and hereinafter for (TA).

In another embodiment of the invention are provided compounds of formula (I), or a pharmaceutically-acceptable salt or an in-vivo hydrolysable ester thereof in which Q, HET (which may also be described as —N-HET herein) and other substituents mentioned above have the values disclosed hereinbefore, and T is as defined hereinbefore and hereinafter for (TA) and (TC).

Preferably Q is selected from Q1, Q2, Q4 and Q6; especially Q1 and Q2; and most preferably Q is Q1.

Preferably R1 is methyl;

In (TAb), preferred are (TAb1) to (TAb5), and especially (TAb2), (TAb3) and/or (TAb5), most especially (TAb2) and (TAb5). In another embodiment, in (TAb), preferred are (TAb2), (TAb3), (TAb5) and (TAb6). The above preferred values of (TAb) are particularly preferred when present in Q1 or Q2, especially Q1.

In (TAb) it is to be understood that when a value for —$X^1$— is a two-atom link and is written, for example, as —$CH_2NH$— it is the left hand part (—$CH_2$— here) which is bonded to the group of formula (TAb1) to (TAb6) and the right hand part (—NH— here) which is bonded to —$Y^1$— in the definition in (TAbc). Similarly, when —$Y^1$— is a two-atom link and is written, for example, as —CONH— it is the left hand part of —$Y^1$— (—CO— here) which is bonded to the right hand part of —$X^1$—, and the right hand part of —$Y^1$— (—NH— here) which is bonded to the AR2, AR2a, AR2b, AR3, AR3a or AR3b moiety in the definition in (TAbc).

In (TAb) preferably $R^6$ is hydrogen or (1-4C)alkyl, more preferably hydrogen, and $R^4$ and $R^5$ are independently selected from hydrogen, cyano, formyl, bromo, hydroxymethyl, (1-4C)alkyl, methylthio and hydroxyimino, or one of $R^4$ and $R^5$ is selected from group (Taba1). In (TAb) more preferably $R^4$ and $R^5$ are independently selected from hydrogen, cyano, formyl, bromo, hydroxymethyl, (1-4C)alkyl (particularly methyl), methylthio and hydroxyimino. Most preferable is (TAb2) and/or (TAb5) with such preferable substituents.

In (TC), for the avoidance of doubt, $(\ )_{m1}$, $(\ )_{n1}$ and $(\ )_{o1}$ indicate $(—CH_2—)_{m1}$, $(—CH_2—)_{n1}$ and $(—CH_2—)_{o1}$ respectively (optionally substituted as described above).

In the definition of (TC1) to (TC4), in an alternative embodiment >$A_3$-$B_3$— is not >N—$CH_2$— in (TC1) to (TC3).

In the above definition of (TC1) to (TC4) and of the further optional substituents:—

(i) ARc is preferably AR2, and in one embodiment the further optional substituents are preferably not selected from the values listed for Rc.

(ii) A preferred value for G is >N(Rc) or >C(R$^{11}$)(R$^{12}$). Also preferred is G as O or S, particularly in (TC4) when Rp is hydrogen.

(iii) Preferred is (TC4) as piperazinyl, morpholino or thiomorpholino or as tetrahydropyridin-4-yl.

(iv) >A$_3$-B$_3$— is preferably >C(Rq)-CH(Rr)- in (TC1) to (TC3).

Particularly preferred values for the optional substituents and groups defined in (TC) are rings of formula (TC5) to (TC11), particularly when present in Q1 or Q2, especially Q1:—

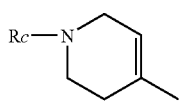 (TC5)

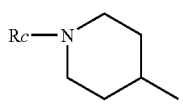 (TC6)

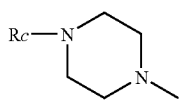 (TC7)

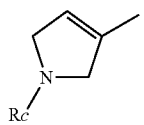 (TC8)

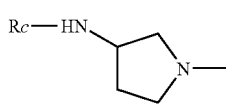 (TC9)

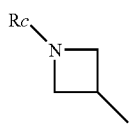 (TC10)

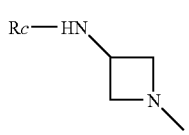 (TC11)

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially R$^{13}$CO— with the preferable R$^{13}$ values given hereinafter). In (TC5) Rc is preferably selected from the group (Rc2), especially R$^{13}$CO— with the preferable R$^{13}$ values given hereinafter. In (TC7) Rc is preferably selected from group (Rc3) or (Rc4).

For (TC), further preferred values for the optional substituents and groups defined in (TC) are rings of formula (TC12) and (TC13), particularly when present in Q1 or Q2, especially Q1:—

 (TC12)

 (TC13)

wherein G is —O—, —S—, —SO—, —SO$_2$— or >N(Rc) and Rc, o1 and n1 have any of the values defined herein.

Preferably (TC12) is (TC12a), (TC12b), (TC12c) or (TC12d) and preferably (TC13) is (TC13a), particularly when present in Q1 or Q2, especially Q1:—

 (TC12a)

 (TC12b)

 (TC12c)

 (TC12d)

 (TC13a)

wherein m is 0, 1 or 2.

In (TDa), particularly preferred values are when present in Q1 or Q2, especially Q1.

In (TDb) it will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an sp$^2$ carbon atom is directed towards a bridgehead position).

In (TDb), particularly preferred values of (TDb) are the following structures of formula (TDb4), (TDb8) and/or (TDb9); wherein Rc has any of the values listed hereinbefore or hereinafter. The values of (TDb) are particularly preferred when present in Q1 or Q2, especially Q1.

 (TDb4a & b)

[2, 2, 1]

-continued

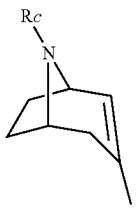

[3, 2, 1]

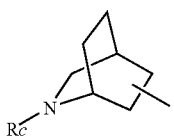

[2, 2, 2]

In (TE1) to (TE3), preferred values for the groups defined in (TE) are defined by formulae (TE1a, b), (TE2a) and (TE3a), particularly when present in Q1 or Q2, especially Q1:

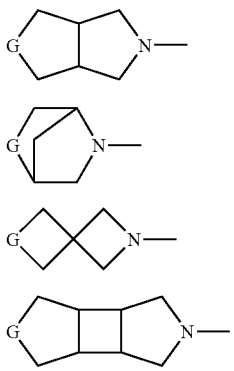

wherein G is —O—, —S—, —SO— or —SO$_2$—.

Preferable values for other substituents (which may be used where appropriate with any of the definitions and embodiments disclosed hereinbefore or hereinafter) are:—

(a) —N-HET is preferably of formula (Ic), (Id) or (If).—N-HET is more preferably of formula (Id) or (If).

(b) In one aspect preferably one of R$^2$ and R$^3$ is hydrogen and the other fluoro. In another aspect both R$^2$ and R$^3$ are fluoro.

(c) In another aspect one of R$^2$ and R$^3$ is hydrogen or fluoro and the other is selected from C$_1$, CF$_3$, Me, Et, OMe and SMe.

(d) In (TC4) preferably >A$_3$-B$_3$— is >C=CH— or >N—CH$_2$—.

(e) Preferably Rc is R$^{13}$CO— and preferably R$^{13}$ is (1-4C)alkoxycarbonyl, hydroxy(1-4C)alkyl, (1-4C)alkyl (optionally substituted by one or two hydroxy groups, or by an (1-4C)alkanoyl group), (1-4C)alkylamino, dimethylamino(1-4C)alkyl, (1-4C)alkoxymethyl, (1-4C)alkanoylmethyl, (1-4C)alkanoyloxy(1-4C)alkyl, (1-5C)alkoxy or 2-cyanoethyl.

(f) More preferably R$^{13}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl.

(g) Particularly preferred as R$^{13}$ is 1,2-dihydroxyethyl, 1,3-dihydroxyprop-2-yl or 1,2,3-trihydroxyprop-1-yl.

(h) In another embodiment, particularly preferred as R$^{13}$ is 1,2-dihydroxyethyl, hydroxymethyl or acetoxymethyl, (i) In another aspect preferably R$^{13}$ is (1-10C)alkyl [optionally substituted by one or more hydroxy] or R$^{14}$C(O)O(1-6C)alkyl. More preferably R$^{13}$ is (1-4C)alkyl [optionally substituted by one or two hydroxy] or R$^{14}$C(O)O(1-6C)alkyl.

For compounds of formula (I) preferred values for Rc are those in group (Rc2) when present in any of the definitions herein containing Rc—for example when present in compounds in which there is a (TC5) or (TC9) ring system.

In the definition of (Rc2c) the AR2a, AR2b, AR3a and AR3b versions of AR2 and AR3 containing groups are preferably excluded.

Where the number of optional substituents on a group is not otherwise preferably defined, the preferable number of optional substituents is one.

Particularly preferred compounds of the present invention are of the formula (IB):

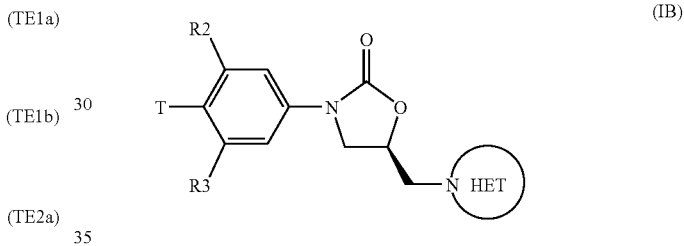

wherein —N-HET is 1,2,3-triazol-1-yl or tetrazol-2-yl;
R1 is methyl;
R$^2$ and R$^3$ are independently hydrogen or fluoro; and
T is selected from (TAb1 to 6), (TC5), (TC7), (TC9), (TC12), (TC13) and (TE1) to (TE3); or in-vivo hydrolysable esters or pharmaceutically-acceptable salts thereof.

Further especially preferred compounds of the invention are of the formula (IB) defined above wherein T is selected from (TAb2 & 5), (TC5), (TC9), (TC12a to d), (TC13a), (TE1a & b), (TE2a) and (TE3a); or in-vivo hydrolysable esters or pharmaceutically-acceptable salts thereof.

Further especially preferred compounds of the invention are of the formula (IB) defined above wherein T is selected from (TAb2, 3, 5 & 6), (TC5), (TC12a, b and d) and (TC13a); or in-vivo hydrolysable esters or pharmaceutically-acceptable salts thereof.

Further especially preferred compounds of the invention are of the formula (IB) defined above wherein T is selected from (TAb2 & 5), (TC5) and (TC9); or in-vivo hydrolysable esters or pharmaceutically-acceptable salts thereof.

In the above aspects and preferred compounds of formula (IB), in (TC5), (TC7), (TC9), preferably Rc is as defined in (Rc2) and especially R$^{13}$CO— wherein R$^{13}$ is preferably (1-4C)alkoxycarbonyl, hydroxy(1-4C)alkyl, (1-4C)alkyl (optionally substituted by one or two hydroxy groups, or by an (1-4C)alkanoyl group), (1-4C)alkylamino, dimethylamino(1-4C)alkyl, (1-4C)alkoxymethyl, (1-4C)alkanoylmethyl, (1-4C)alkanoyloxy(1-4C)alkyl, (1-5C)alkoxy or 2-cyanoethyl. More preferably wherein Rc is as defined in (Rc2) and especially R$^{13}$CO— wherein R$^{13}$ is preferably (1-4C)alkoxycarbonyl, hydroxy(1-4C)alkyl and (1-4C)alkyl (optionally substituted by one or two hydroxy groups, or by an (1-4C)alkanoyl group).

In all of the above aspects and preferred compounds of formula (IB), in-vivo hydrolysable esters are preferred where appropriate, especially phosphoryl esters (as defined by formula (PD4) with npd as 1).

In all of the above definitions the preferred compounds are as shown in formula (IA), i.e. the pharmaceutically active enantiomer.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron triS(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro) phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference:

WO99/02525; WO98/54161; WO97/37980; WO97/30981 (& U.S. Pat. No. 5,736,545); WO97/21708 (& U.S. Pat. No. 5,719,154); WO97/10223; WO97/09328; WO96/35691; WO96/23788; WO96/15130; WO96/13502; WO95/25106 (& U.S. Pat. No. 5,668,286); WO95/14684 (& U.S. Pat. No. 5,652,238); WO95/07271 (& U.S. Pat. No. 5,688,792); WO94/13649; WO94/01110; WO93/23384 (& U.S. Pat. Nos. 5,547,950 & 5,700,799); WO93/09103 (& U.S. Pat. Nos. 5,565,571, 5,654,428, 5,654,435, 5,756,732 & 5,801,246); U.S. Pat. Nos. 5,231,188; 5,247,090; 5,523,403; WO97/27188; WO97/30995; WO97/31917; WO98/01447; WO98/01446; WO99/10342; WO99/10343; WO99/11642; WO99/64416; WO99/64417; WO00/21960; WO01/40222; WO01/81350 and WO01/98297; European Patent Application Nos. 0,359,418 and 0,609,905; 0,693,491 A1 (& U.S. Pat. No. 5,698,574); 0,694,543 A1 (& AU 24985/95); 0,694,544 A1 (& CA 2,154,024); 0,697,412 A1 (& U.S. Pat. No. 5,529,998); 0,738,726 A1 (& AU 50735/96); 0,785,201 A1 (& AU 10123/97); German Patent Application Nos. DE 195 14 313 A1 (& U.S. Pat. No. 5,529,998); DE 196 01 264 A1 (& AU 10098/97); DE 196 01 265 A1 (& AU 10097/97); DE 196 04 223 A1 (& AU 12516/97); DE 196 49 095 A1 (& AU 12517/97).

The following Patent and Application Publications may also provide useful information and the contents of the relevant process sections are hereby incorporated herein by reference:

FR 2458547; FR 2500450(& GB 2094299, GB 2141716 & U.S. Pat. No. 4,476,136); DE 2923295 (& GB 2028306, GB 2054575, U.S. Pat. Nos. 4,287,351, 4,348,393, 4,413,001, 4,435,415 & 4,526,786), DE 3017499 (& GB 2053196, U.S. Pat. No. 4,346,102 & U.S. Pat. No. 4,372,967); U.S. Pat. No. 4,705,799; European Patent Application Nos. 0,312,000; 0,127,902; 0,184,170; 0,352,781; 0,316,594;

The skilled organic chemist will be able to use and adapt the information contained and referenced within the above references, and accompanying Examples therein and also the Examples herein, to obtain necessary starting materials, and products.

Thus, the present invention also provides that the compounds of the formula (I) and pharmaceutically-acceptable salts and in vivo hydrolysable esters thereof, can be prepared by a process (a) to (g) as follows (wherein the variables are as defined above unless otherwise stated):

(wherein the variables are as defined above unless otherwise stated):

(a) by modifying a substituent in, or introducing a new substituent into, the substituent group Q of another compound of formula (I)—for instance by (i) displacement of a functional group from a compound of formula (I) by another functional group, (ii) by oxidation or (iii) reduction of a compound of formula (I), by (iv) addition of a reagent to or (v) elimination of a reagent from a compound of formula (I), by (vi) metathesis of a compound of formula (I) into a modified compound of formula (I), or by (vii) rearrangement of a compound of formula (I) to an isomeric compound of formula (I) (Scheme I shows examples drawn from the range of suitable methods); or (b) by reaction of a compound of formula (II):

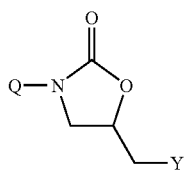

(II)

wherein Y is a displaceable group (which may be preformed, such as chloro or mesylate, or generated in-situ, for example under Mitsunobu conditions) with a compound of the formula (III):

HET (III)

wherein HET (of formula (Ia) to (If), already substituted and optionally protected) is HET-H free-base form or HET-anion formed from the free base form (Scheme II shows examples drawn from the range of suitable methods); or (c) by reaction of a compound of the formula (IV):

Q-Z (IV)

wherein Z is an isocyanate, amine or urethane group with an epoxide of the formula (V) wherein the epoxide group serves as a leaving group at the terminal C-atom and as a protected hydroxy group at the internal C-atom; or with a related compound of formula (VI) where the hydroxy group at the internal C-atom is conventionally protected e.g. with an acetyl group and where the leaving group Y at the terminal C-atom is a conventional leaving group e.g. a chloro- or mesyloxy-group.

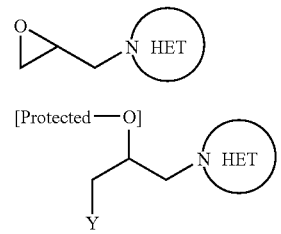

(V)

(VI)

(Scheme III shows examples drawn from the range of suitable methods), or (d) (i) by coupling, using catalysis by transition metals such as palladium(0), of a compound of formula (VII):

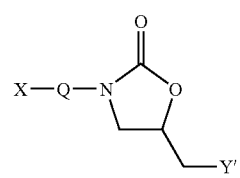

(VII)

wherein Y' is a group HET as hereinbefore defined, X is a replaceable substituent—such as chloride, bromide, iodide, or trifluoromethylsulfonyloxy;

with a compound of the formula (VIII), or an analogue thereof, which is suitable to give a T substituent as defined by (TA)-(TE), in which the link is via an sp² carbon atom (D=CH=C— Lg where Lg is a leaving group such as chloride, bromide, iodide, or trifluoromethylsulfonyloxy; or as in the case of reactions carried out under Heck reaction conditions Lg may also be hydrogen) or in which the link is via an N atom (D=NH)

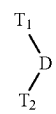

(VIII)

where $T_1$ and $T_2$ may be the same or different or may together with D form a ring of type T as hereinbefore described (Scheme IV shows examples drawn from the range of suitable methods);

(d) (ii) by coupling, using catalysis by transition metals such as palladium(0), of a compound of formula (VIIA):

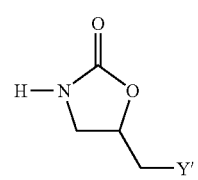

(VIIA)

wherein Y' is a group HET as hereinbefore defined, with a compound

[Aryl]-X where X is a replaceable substituent—such as chloride, bromide, iodide, or trifluoromethylsulfonyloxy, or an analogue thereof (Scheme IV shows an example drawn from the range of suitable methods);

(e) Where N-HET is 1,2,3-triazole there is the additional possibility by cycloaddition via the azide (wherein Y in (II) is azide), with a substituted acetylene or a masked acetylene (such as a vinyl sulfone, a nitroloefin, or an enamine, or a substituted cyclohexa-1,4-diene derivative (Scheme II shows examples drawn from the range of suitable methods);

(f) Where N-HET is 1,2,3-triazole there is the additional possibility of synthesis by reaction of a compound of formula (II) where $Y=NH_2$ (primary amine) with a compound of formula (IX), namely the arenesulfonylhydrazone of a methyl ketone that is further geminally substituted on the methyl group by two substituents (Y' and Y") capable of being eliminated from this initial, and the intermediate, substituted hydrazones as HY' and HY" (or as conjugate bases thereof) (Scheme V shows an example drawn from the range of suitable methods);

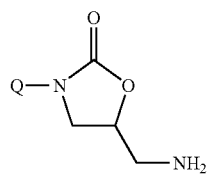

(II: Y = NH2)

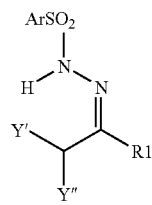

(g) Where N-HET is 1,2,3-triazole there is the additional possibility of regioselective synthesis by cycloaddition via the azide (wherein Y in (II) is azide) with a terminal alkyne using Cu(I) catalysis in e.g. aqueous alcoholic solution at ambient temperatures to give 4-substituted 1,2,3-triazoles

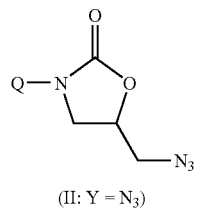

(II: Y = N3)

and thereafter if necessary: (i) removing any protecting groups; (ii) forming a pharmaceutically-acceptable salt; (iii) forming an in-vivo hydrolysable ester.

The main synthetic routes are illustrated in Schemes (I) to (VI) below (with Q as phenyl, and T, R1=(1-4C)alkyl, R2, R3, and A defined with reference to analogous substituents defined elsewhere herein). The compounds of the invention may be prepared by analogous chemistry adapted from these Schemes. Schemes (II) and (VI) also show the preparation of 1,2,3-triazoles via the azide (prepared from the relevant hydroxy compound) and the amine (prepared e.g. from the azide) respectively.

Scheme I

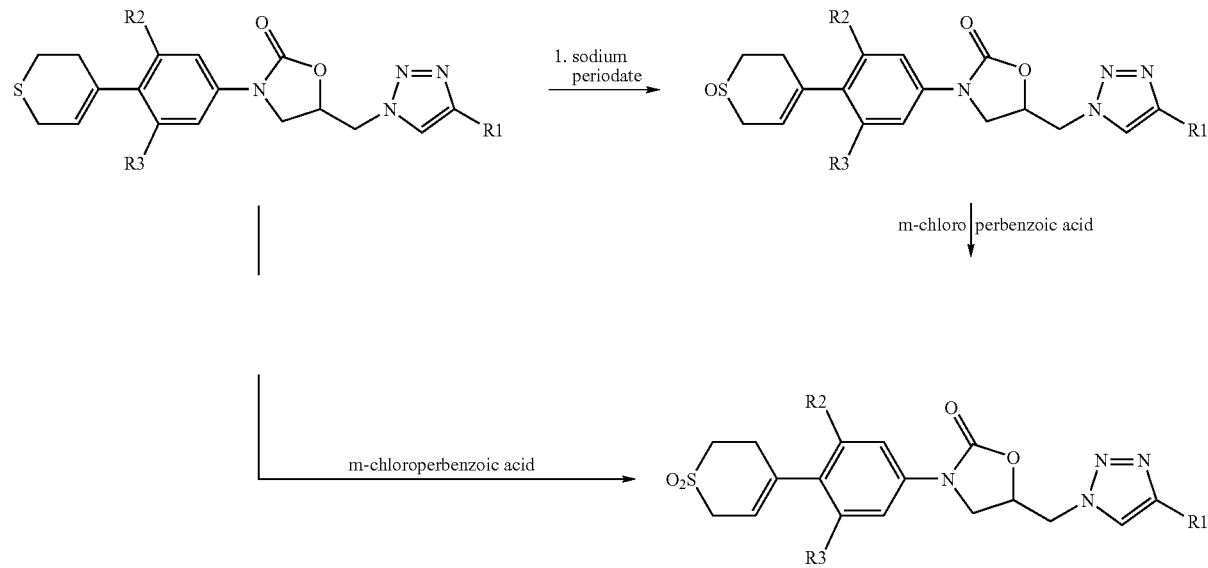

-continued
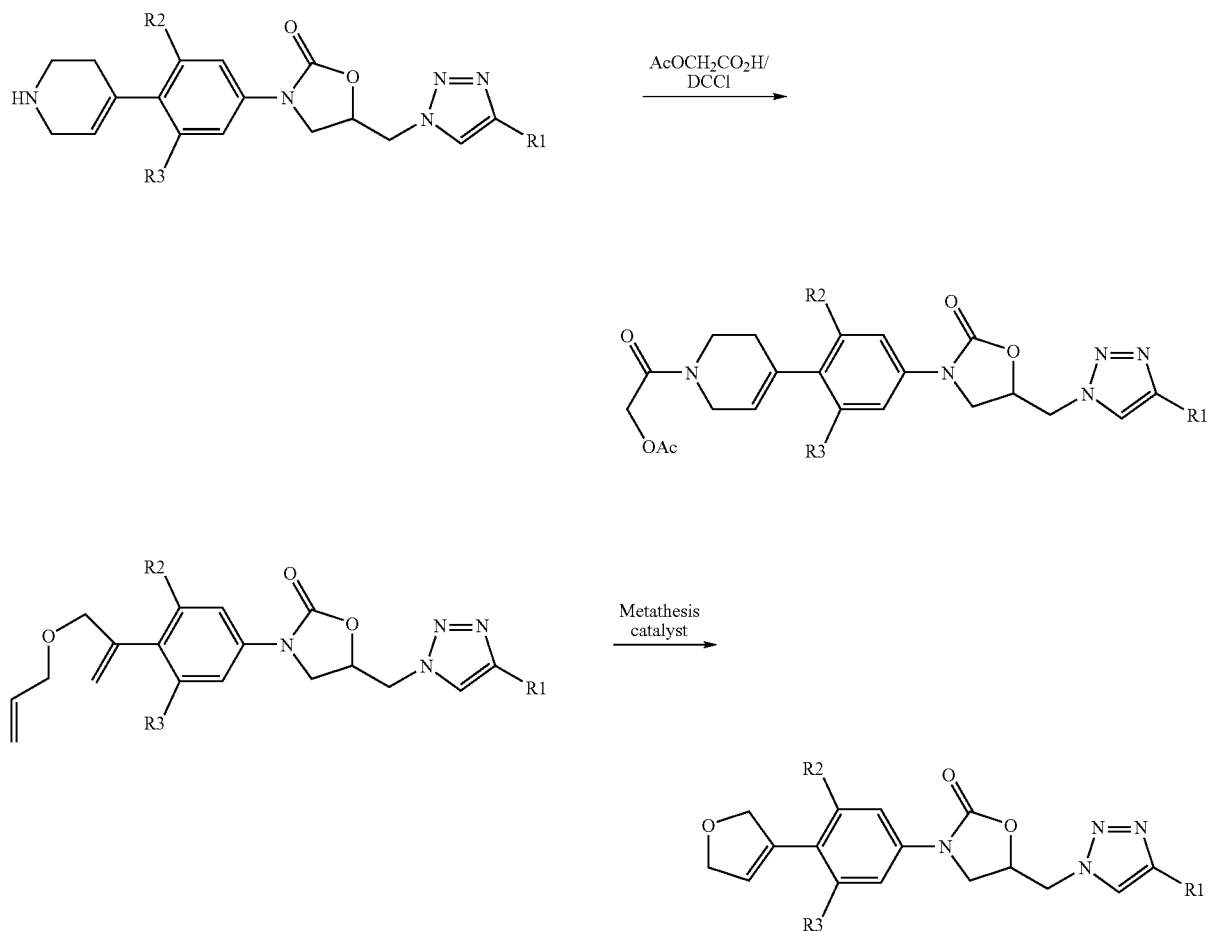
Scheme II
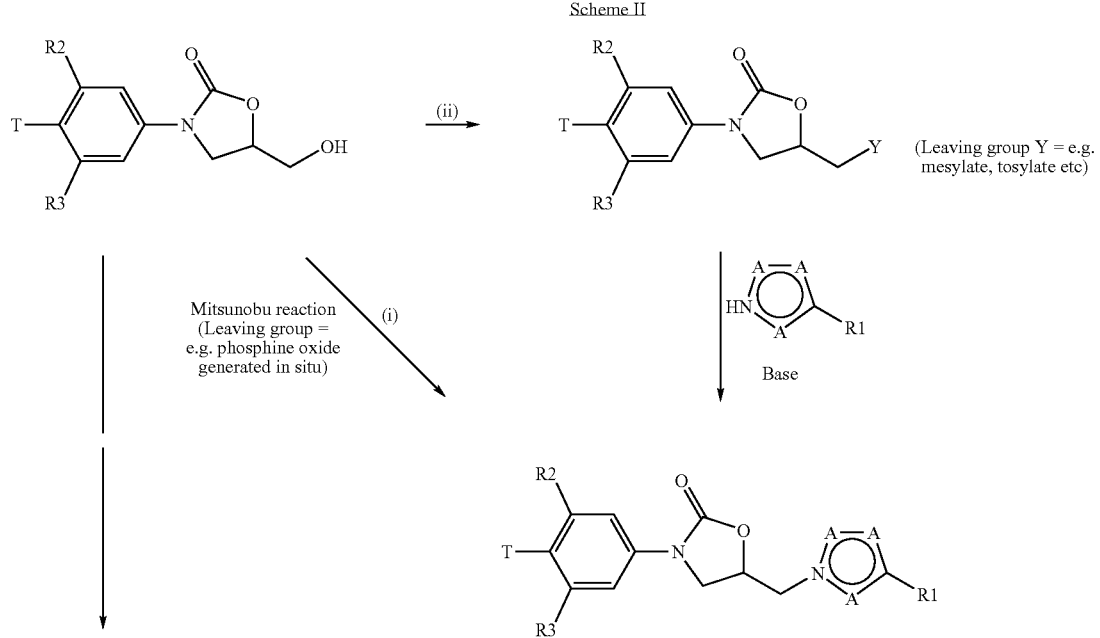

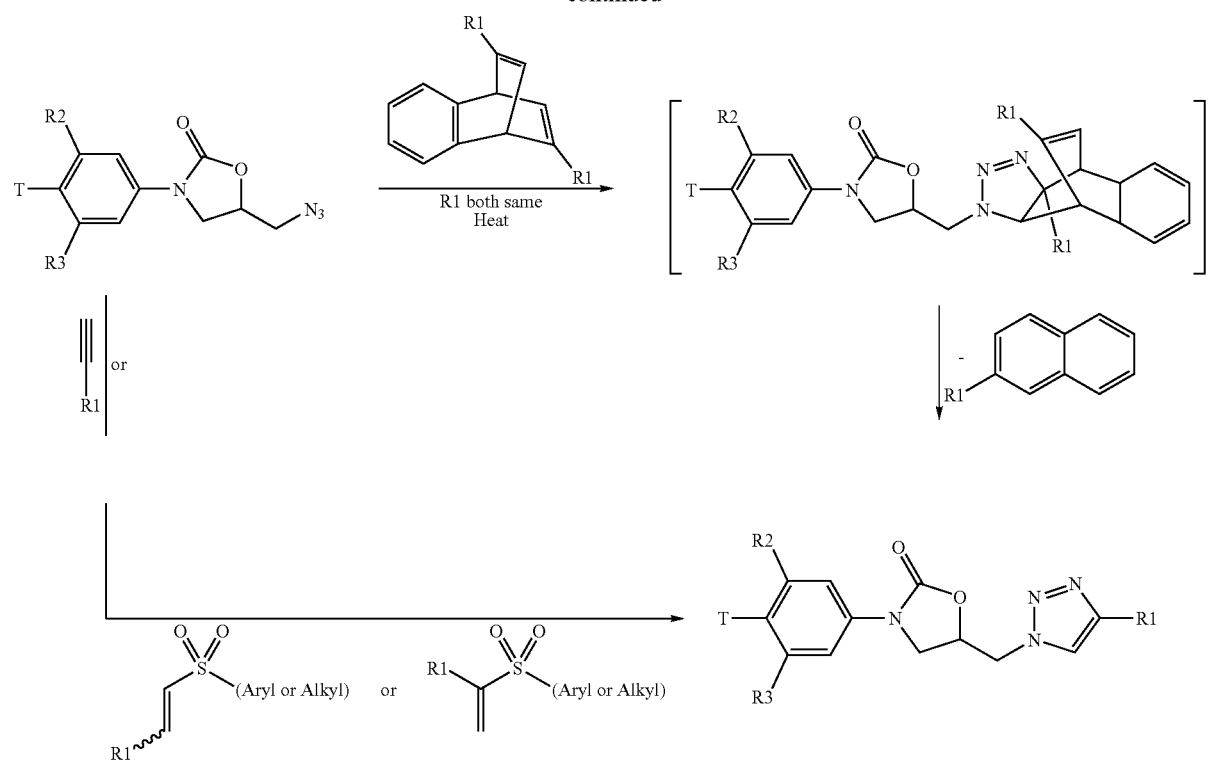
Scheme III
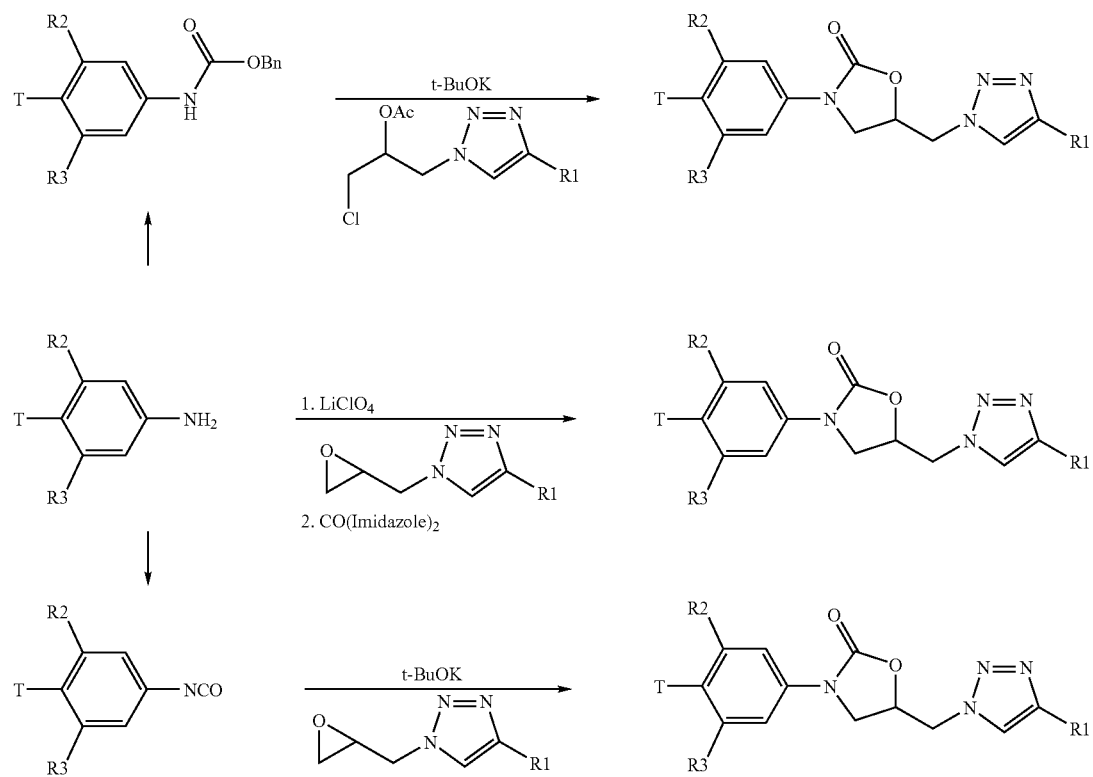

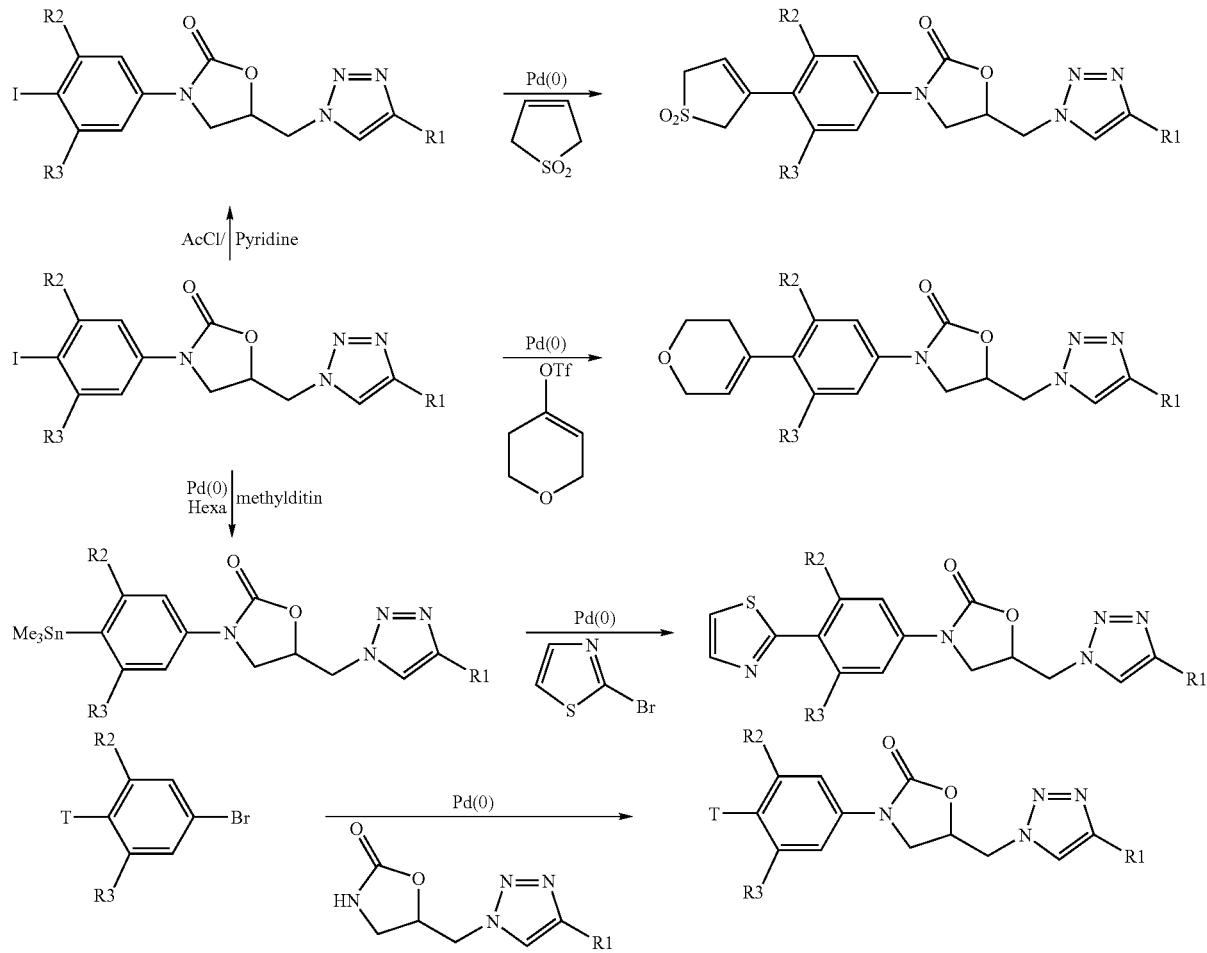
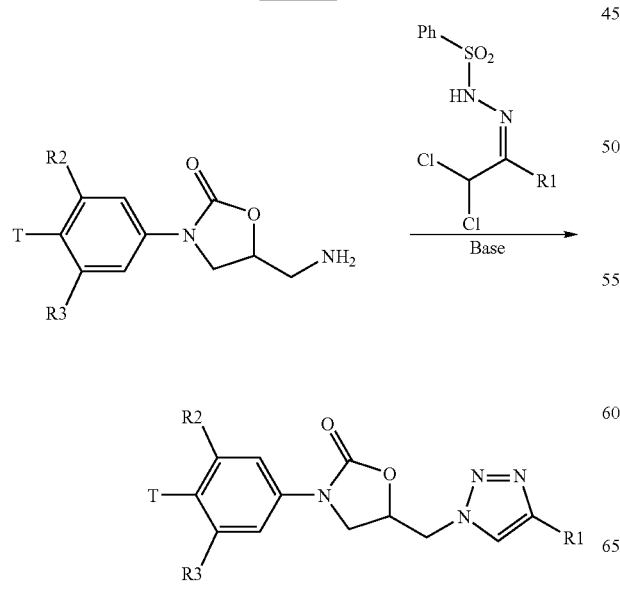
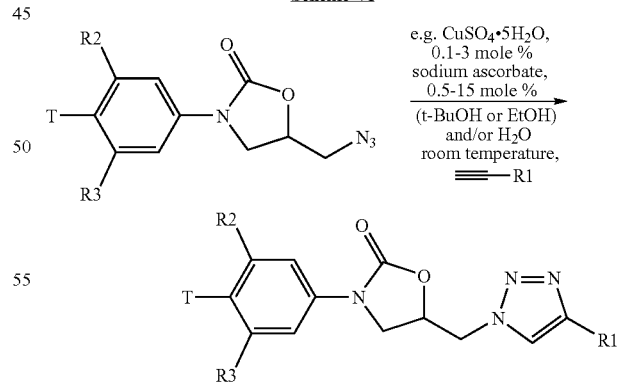
Deprotection, salt formation or in-vivo hydrolysable ester formation may each be provided as a specific final process step.
The N-linked hetereocycle can of course be prepared early in the overall synthesis, and then other functional groups changed.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J.Wiley & Sons), 1992. Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, for example International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I), for example, acylation of a group of formula (TC5) wherein Rc is hydrogen.

(b)(i) Reaction (b)(i) (in which Y is initially hydroxy) is performed under Mitsunobu conditions, for example, in the presence of tri-n-butylphosphine and diethyl azodicarboxylate (DEAD) in an organic solvent such as THF, and in the temperature range 0° C.-60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Compounds of the formula (II) wherein Y is hydroxy may be obtained as described in the references cited herein (particularly in the section proceeding the discussion of protecting groups), for example, by reacting a compound of the formula (X) with a compound of formula (XI):

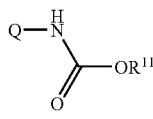

(X)

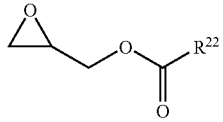

(XI)

wherein R$^{21}$ is (1-6C)alkyl or benzyl and R$^{22}$ is (1-4C)alkyl or —S(O)$_n$(1-4C)alkyl where n is 0, 1 or 2. Preferably R$^{22}$ is (1-4C)alkyl.

In particular, compounds of the formula (II), (X) and (XI) may be prepared by the skilled man, for example as described in International Patent Application Publication Nos. WO95/07271, WO97/27188, WO 97/30995, WO 98/01446 and WO 98/01447, the contents of which are hereby incorporated by reference, and by analogous processes.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt.I (1993), 45-225, B. J. Wakefield.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25-60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux.

When Y is (1-4C)alkanesulfonyloxy or tosylate the compound (II) may be prepared by reacting the hydroxy compound with (1-4C)alkanesulfonyl chloride or tosyl chloride in the presence of a mild base such as triethylamine or pyridine.

When Y is a phosphoryl ester (such as (PhO)$_2$—P(O)—O—) or Ph$_2$—P(O)—O— the compound (II) may be prepared from the hydroxy compound under standard conditions.

(c) Reaction (c) is performed under conditions analogous to those described in the following references which disclose how suitable and analogous starting materials may be obtained.

Reaction (c) is especially suitable for compounds in which HET-H is a weakly acidic heterocycle (such as, for example, triazole or tetrazole).

Compounds of the formula Q-Z wherein Z is an isocyanate may be prepared by the skilled chemist, for example by analogous processes to those described in Walter A. Gregory et al in J. Med. Chem. 1990, 33, 2569-2578 and Chung-Ho Park et al in J. Med. Chem. 1992, 35, 1156-1165. Compounds of the formula Q-Z wherein Z is a urethane may be prepared by the skilled chemist, for example by analogous processes to those described in International Patent Application Publication Nos. WO 97/30995 and WO 97/37980.

A similar reaction to reaction (c) may be performed in which Q-Z wherein Z is a amine group is reacted with the epoxide (optionally in the presence of an organic base), and the product is reacted with, for example, phosgene to form the oxazolidinone ring. Such reactions and the preparation of starting materials is within the skill of the ordinary chemist with reference to the above-cited documents disclosing analogous reactions and preparations.

Epoxides of the formula (V) may be prepared from the corresponding compound of formula (XII):

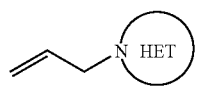

(XII)

Certain such epoxide and alkene intermediates are novel and are provided as a further feature of the invention. Asymmetric epoxidation may be used to give the desired optical isomer. Compounds of formula (VI) may be obtained from epoxides of formula (V); alternatively compounds of formula (VI) may be used as precursors for epoxides of formula (V) according to the relative ease of synthesis in each case. The skilled chemist will appreciate that the epoxides of formula (V) and the compounds of formula (VI) are structurally equivalent and the choice between them will be made on the grounds of availability, convenience, and cost.

(d) The transition metal catalysed coupling reaction to form a C—C or N—C bond from the corresponding aryl derivatives and the arenes, heteroarenes, olefins, alkynes, or amines is performed under conventional conditions (see for instance J. K. Stille, Angew. Chem. Int. Ed. Eng., 1986, 25, 509-524; N. Miyaura and A. Suzuki, Chem. Rev., 1995, 95, 22457-2483; D. Baranano, G. Mann, and J. F. Hartwig, Current Org. Che., 1997, 1, 287-305; S. P. Stanforth, Tetrahedron, 1998, 54, 263-303). The reaction d (ii) may be conveniently carried out under the conditions described in Tetrahedron Letters (2001), 42(22), 3681-3684, or in the analogous conventional conditions described in the above mentioned literature. In such a procedure a preferred variation of X may be bromine.

(e) The cycloaddition reaction to form 1,2,3 triazoles from the corresponding azide is performed under conventional conditions. Compounds of the formula (II) wherein Y is azide may be obtained as described in the references cited herein (particularly in the section proceeding the discussion of protecting groups), for example from the corresponding compounds in which Y is hydroxy or mesylate.

(f) The reaction of amines of formula (II, Y=NH2) with arenesulfonyl hydrazones to form 1,2,3 triazoles may be carried out as described in the literature (Sakai, Kunikazu; Hida, Nobuko; Kondo and Kiyosi: "Reactions of α-polyhalo ketone tosylhydrazones with sulfide ion and primary amines. Cyclization to 1,2,3-thiadiazoles and 1,2,3-triazoles." Bull. Chem. Soc. Jpn. (1986), 59(1), 179-83; Sakai, Kunikazu; Tsunemoto, Daiei; Kobori, Takeo; Kondo, Kiyoshi; Hida and Nobuko: 1,2,3-Trihetero 5-membered heterocyclic compounds, EP 103840 A2 19840328). The leaving groups Y', Y" may be chloro or any other group capable of being eliminated from the arenesulfonyl hydrazone during the reaction with the amine. The skilled chemist will also appreciate that a similar reaction may be used to produce other substituted triazoles suitable for incorporation into related processes such as reaction with compounds of formula (IV) in process (c).

(g) The reaction of azides of formula (II, Y=N₃) with terminal alkynes using Cu(I) catalysis to give regioselectively 4-substituted 1,2,3-triazole compounds of formula (I) may be carried out as described in the literature (for instance V. V. Rostovtsev, L. G. Green, V. V. Fokin, and K. B. Sharpless, Angew. Chem. Int. Ed., 2002, 41, 2596-2599).

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and for use as an anti-bacterial agent; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration as eye-drops, for administration by inhalation (for example as a finely divided powder or a liquid aerosol), for administration by insufflation (for example as a finely divided powder) or for parenteral administration (for example as a sterile aqueous or oily solution for intravenous, subcutaneous, sub-lingual, intramuscular or intramuscular dosing or as a suppository for rectal dosing).

In addition to the compounds of the present invention, the pharmaceutical composition of this invention may also contain (ie through co-formulation) or be co-administered (simultaneously, sequentially or separately) with one or more known drugs selected from other clinically useful antibacterial agents (for example, β-lactams, macrolides, quinolones or aminoglycosides) and/or other anti-infective agents (for example, an antifungal triazole or amphotericin). These may include carbapenems, for example meropenem or imipenem, to broaden the therapeutic effectiveness. Compounds of this invention may also be co-formulated or co-administered with bactericidal/permeability-increasing protein (BPI) products or efflux pump inhibitors to improve activity against gram negative bacteria and bacteria resistant to antimicrobial agents.

The compositions of the invention may be obtained by conventional procedures using conventional pharmaceutical excipients, well known in the art. Thus, compositions intended for oral use may contain, for example, one or more colouring, sweetening, flavouring and/or preservative agents. A pharmaceutical composition to be dosed intravenously may contain advantageously (for example to enhance stability) a suitable bactericide, antioxidant or reducing agent, or a suitable sequestering agent.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol. Solubility enhancing agents, for example cyclodextrins may be used.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 50 mg to 5 g of active agent compounded with an appropriate and convenient amount of excipients which may vary from about 5 to about 98 percent by weight of the total composition. Dosage unit forms will generally contain about 200 mg to about 2 g of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

In the above other, pharmaceutical composition, process, method, use and medicament manufacture features, the alternative and preferred embodiments of the compounds of the invention described herein also apply.

Biological Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S.aureus* and coagulase negative staphylococci, together with *haemophilus* and *moraxella* strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of 10$^4$ CFU/spot. Typically, compounds are active in the range 0.01 to 256 µg/ml.

Staphylococci were tested on agar, using an inoculum of 104 CFU/spot and an incubation temperature of 37° C. for 24 hours—standard test conditions for the expression of methicillin resistance.

Streptococci and enterococci were tested on agar supplemented with 5% defibrinated horse blood, an inoculum of 10$^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of 5×10$^4$ CFU/well.

| | MIC (µg/ml) | |
|---|---|---|
| Organism | Example 1 | Reference Example 1 |
| *Staphylococcus aureus*: | | |
| MSQS | 2 | 2 |
| MRQR | 4 | 2 |
| *Streptococcus pneumoniae* | | |
| | 0.5 | 1 |
| | 0.5 | 1 |
| *Streptococcus pyogenes* | 1 | 1 |
| *Haemophilus influenzae* | 2 | 4 |
| *Moraxella catarrhalis* | 2 | 2 |

MSQS = methicillin sensitive and quinolone sensitive
MRQR = methicillin resistant and quinolone resistant The activity of the compounds of the invention against MAO-A was tested using a standard in-vitro assay based on human liver enzyme expressed in yeast as described in Biochem. Biophys. Res. Commun. 1991, 181, 1084-1088. Ki values were determined using serial two-fold dilutions from 20 mm to 0.04 µM.

The compounds of the invention showed decreased MAO-A potency compared with analogues from the known art with C-5 side chains such as acetamidomethyl or unsubstituted azolylmethyl or hydroxymethyl. The compounds of the invention showed decreased MAO-A potency compared with analogues in which the HET group of formula (Ia) to (If) is unsubstituted.

For comparison, Example 1 was compared with the compounds of Reference Example 1 (see WO 01/81350; Example 82) and Reference Example 2 (see WO 97/09328; Example 63):

REFERENCE EXAMPLE 1

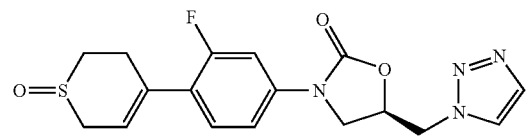

REFERENCE EXAMPLE 2

| Results: | MAO-A Ki (µM) |
|---|---|
| Example 1 | 16 |
| Reference Example 1 | 3.6 |
| Reference Example 2 | 0.5 |

MAO activity in general comprises activity in both MAO-A and MAO-B enzymes. The compounds of the invention in general demonstrate favourable profiles against both enzymes.

Certain intermediates and/or Reference Examples described hereinafter within the scope of the invention may also possess useful activity, and are provided as a further feature of the invention.

The invention is now illustrated but not limited by the following Examples in which unless otherwise stated:—

(i) evaporations were carried out by rotary evaporation in vacuo and work-up procedures were carried out after removal of residual solids by filtration;

(ii) operations were carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected];

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:—

NOE is Nuclear Overhauser Effect; DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; EI is electron impact; CI is chemical ionisation; APCI is atmospheric pressure chemical ionisation; EtOAc is ethyl acetate; MeOH is methanol; LiHMDS is lithium hexamethyldisilazide; THF is tetrahydrofuran; TFA is trifluoroacetic acid.

EXAMPLE 1

(5R)-3-[4-(1(R,S)-Oxo-3,6-dihydro-2H-thiopyran-4-yl)-3-fluorophenyl]-5-[(4-methyl)-1,2,3-triazol-1-ylmethyl]oxazolidin-2-one

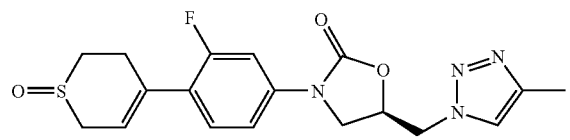

(5R)-3-[4-(1 (R,S)-Oxo-3,6-dihydro-2H-thiopyran-4-yl)-3-fluorophenyl]-5-azidomethyloxazolidin-2-one (0.35 g, 1.0 mmol; Intermediate 1) was mixed with 5,6,7,8-tetrachloro-2,9-dimethyl-1,4-dihydro-1,4-ethenonaphthalene (0.64 g, 2.0 mmol) in dry 1,4-dioxane (4 ml) in a sealed microwave reaction tube. The tube was placed in a Smith microwave reactor at 170° C. for 20 minutes. The reaction mixture was then transferred into a round bottom flask and the solvent was removed under vacuum. The residue was purified by chromatography on silicagel with 5% methanol in dichloromethane to give a mixture of the 4- and 5-methyl regioisomers. This mixture was further separated on a chiral column (chiralcel OD) with isopropanol/hexanes (1:1) to give the title product (74 mg).

MS (ESP): 391.18 ($MH^+$) for $C_{18}H_{19}FN_4O_3S$ $^1$H-NMR (DMSO-$d_6$) δ: 2.24 (s, 3H); 2.85-3.00 (m, 2H); 3.14 (m, 1H); 3.40 (m, 2H) overlapping with DMSOd6; 3.65 (m, 1H); 3.90 (dd, 1H); 4.25 (dd, 1H); 4.76 (d, 2H); 5.15 (m, 1H); 5.84 (m, 1H); 7.29 (dd, 1H); 7.40 (dd, 1H); 7.46 (dd, 1H); 7.89 (s, 1H).

4-methyl substitution on the triazole moiety was confirmed by comparison with the corresponding 5-methyl compound, which was synthesized separately via another synthetic route and had its structure confirmed by NOE experiments. The 5-methyl regioisomer shows H-4 of the triazole moiety at 7.53 ppm.

Note: We found that the 4- and 5-substituted 1,2,3-triazoles reported here can generally be distinguished based on the difference in the chemical shifts for the $^1$H-resonnances of H-5 and H-4 of the triazole moiety: H-5 is for all examples considerably lower than H-4 (G. Alonso, M. T. Garcia-Lopez, G. Garcia-Munoz, R. Madronero and M. Rico, J. Heterocycl. Chem. 1970, 7, 1269-1272).

Intermediate 1: (5R)-3-[4-(1(R,S)-Oxo-3,6-dihydro-2H-thiopyran-4-yl)-3-fluorophenyl]-5-azidomethyloxazolidin-2-one

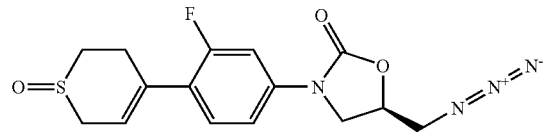

(5R)-3-[4-(3,6-Dihydro-2H-thiopyran-4-yl)-3-fluorophenyl]-5-azidomethyloxazolidin-2-one (2.3 g, 6.5 mmol) (see WO 01/81350) was dissolved in methanol/ethylacetate (1:1, 100 ml) and sodium periodate (1.75 g, 8.2 mmol), dissolved in water (20 ml) was added dropwise over 1 hour. The reaction mixture was stirred for 7 hours at room temperature, filtered to remove most of the salts and the methanol was evaporated under vacuum. The aqueous solution thus obtained was extracted with ethyl acetate, dried over sodium sulfate and it was evaporated to dryness. The residue was subjected to chromatography on silica gel with acetone/hexane (2:1) to give 2.18 g of the product.

MS (ESP): 351.34 (MH$^+$) for $C_{15}H_{15}FN_4O_3S$ $^1$H-NMR (DMSO-d$_6$) δ: 2.58 (m, 1H); 2.85-3.01 (m, 2H); 3.10-3.16 (m, 1H); 3.40 (dd, 1H); 3.64-3.84 (m, 4H); 4.17 (dd, 1H); 4.93 (m, 1H); 5.85 (m, 1H); 7.36 (dd, 1H); 7.41 (dd, 1H); 7.53 (dd, 1H).

EXAMPLE 2

(5R)-3-[4-(1,1-Dioxo-3,6-dihydro-2H-thiopyran-4-yl)-3-fluorophenyl]-5-[(4-isopropyl)-1,2,3-triazol-1-yl)methyl]oxazolidin-2-one

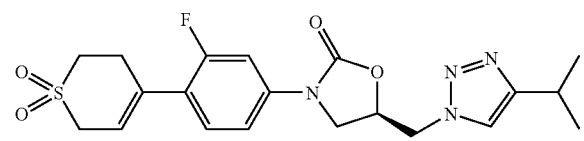

(5R)-3-[4-(1,1-Dioxo-3,6-dihydro-2H-thiopyran-4-yl)-3-fluorophenyl]-5-(azidomethyl) oxazolidin-2-one (Intermediate 2) (0.5 g, 1.36 mmol) and (2-methyl-1-methylenepropyl) phenyl sulfane dioxide (0.72 g, 3.42 mmol) (S. Chodroff and W. F. Whitmore, J. Am. Chem. Soc. 72, 1073-1075, 1950) was heated in a pressure tube to 90° C. for 5 hours. It was diluted with dichloromethane, loaded onto a silica gel column and eluted with hexanes/acetone (1:1). Fractions containing product were pooled, the solvent was evaporated in vacuo and the product was precipitated from dichloromethane/hexanes to give 214 mg (36%) of a colourless solid.

MS (ESP): 435.16 (MH$^+$) for $C_{20}H_{23}FN_4O_4S$ $^1$H-NMR (DMSO-d$_6$) (500 MHz) δ: 1.20 (d, 6H, J 6.9 Hz); 2.93-3.00 (m, 3H); 3.31-3.37 (m, 2H); 3.89-3.94 (m, 3H); 4.26 (dd, 1H, J 9.1, 9.1 Hz); 4.76 (d, 2H, J 4.8 Hz); 5.16 (m, 1H); 5.83 (m, 1H); 7.27 (dd, 1H, J 1.9, 8.6 Hz); 7.40 (dd, 1H, J 8.6, 8.8 Hz); 7.43 (dd, 1H, J 1.9, 13.7 Hz); 7.89 (s, 1H). 4-substitution on the triazole moiety was confirmed by NOE studies.

Intermediate 2: (5R)-3-[4-(1,1-Dioxo-3,6-dihydro-2H-thiopyran-4-yl)-3-fluorophenyl]-5-(azidomethyl) oxazolidin-2-one

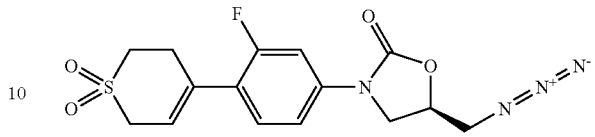

(5R)-3-[4-(3,6-Dihydro-2H-thiopyran-4-yl)-3-fluorophenyl]-5-(azidomethyl)oxazolidin-2-one (WO 01/81350 A1; WO 02/081470 A1) (7 g, 20.9 mmol) was dissolved in dichloromethane (200 ml) and the solution was cooled to 0° C. A solution of 3-chloro perbenzoic acid (15.4 g, 70%, 62.9 mmol) was added drop wise. The reaction mixture was allowed to reach room temperature over 2 hours and it was stirred for an additional 30 minutes at room temperature. It was diluted with ethyl acetate, washed with aqueous sodium thiosulfate solution, then with aqueous sodium hydrogencarbonate solution and with water and dried over sodium sulfate. Chromatography on silica gel with hexanes/acetone (3:2) gave 6.75 g (88%) of the title compound.

MS (ESP): 367.1 (MH$^+$) for $C_{15}H_{15}FN_4O_4S$ $^1$H-NMR (DMSO-d$_6$) (500 MHz) δ: 2.98 (m, 2H); 3.35-3.40 (m, 2H); 3.71 (dd, 1H); 3.79 (dd, 1H); 3.82 (dd, 1H); 3.93 (m, 2H); 4.17 (dd, 1H); 4.93 (m, 1H); 5.84 (m, 1H); 7.37 (dd, 1H); 7.42 (dd, 1H); 7.54 (dd, 1H).

EXAMPLE 3

(5R)-3-[4-(1,1-Dioxo-3,6-dihydro-2H-thiopyran-4-yl)-3,5-difluorophenyl]-5-[(4-methyl)-1,2,3-triazol-1-yl)methyl]oxazolidin-2-one

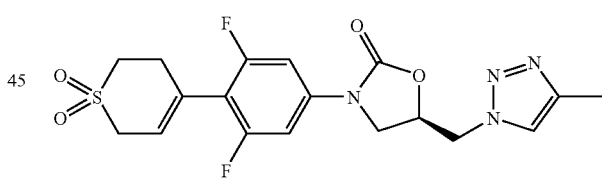

(5S)-3-[4-(1,1-Dioxo-3,6-dihydro-2H-thiopyran-4-yl)-3,5-difluorophenyl]-5-(aminomethyl) oxazolidin-2-one (Intermediate 3) (2.20 g, 6.14 mmol) was dissolved in dry methanol (30 ml). Diisopropylethylamine (1.59 g, 12.28 mmol) was added and the resulting mixture was cooled to 0° C., followed by slow addition of 1,1-dichloroacetone toluenesulfonylhydrazone (2.0 g, 6.75 mmol) [Sakai, Kunikazu; Hida, Nobuko; Kondo, Kiyosi, "Reactions of α-polyhalo ketone tosylhydrazones with sulfide ion and primary amines. Cyclization to 1,2,3-thiadiazoles and 1,2,3-triazoles.", Bulletin of the Chemical Society of Japan (1986), 59(1), p 179-83]. The resulting mixture was stirred at room temperature for 12 hours. Solvent was removed under vacuum and the crude product was purified by flash chromatograph on silica gel with 5% methanol in dichloromethane to give 1.9 g of the title compound.

MS (ESP): 425.12 (MH⁺) for $C_{18}H_{18}F_2N_4O_4S$
¹H-NMR(DMSO-d₆) δ: 2.24 (s, 3H); 2.86 (m, 2H); 3.37 (m, 2H); 3.88 (m, 1H); 3.95 (m, 2H); 4.27 (dd, 1H); 4.76 (d, 2H); 5.15 (m, 1H); 5.78 (s, 1H); 7.33 (d, 2H); 7.89 (s, 1H).

Intermediate 3: (5S)-3-[4-(1,1-Dioxo-3,6-dihydro-2H-thiopyran-4-yl)-3,5-difluorophenyl]-5-(aminomethyl)-oxazolidin-2-one

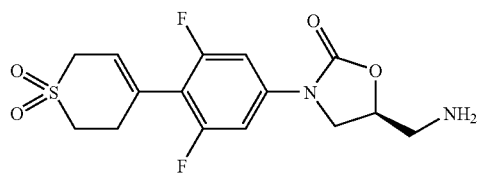

(5S)-5-(Azidomethyl)-3-[4-(1,1-dioxo-3,6-dihydro-2H-thiopyran-4-yl)-3,5-difluorophenyl]-1,3-oxazolidin-2-one (WO 01/81350 A1) (7 g, 18.2 mmol) was dissolved in water (15 ml) and acetonitrile (150 ml). Triphenylphosphine (5.73 g, 21.9 mmol) was added and the resulting mixture was stirred at room temperature for 2 hours. The solvent was evaporated and the residue purified by flash column chromatography on silica gel with 5% methanol in dichloromethane. The fractions containing product were evaporated to near dryness and treated with ethereal HCl to precipitate the hydrochloride salt of the title compound as a white solid (5.03 g, 70%).
MS (ESP): 359 (MH⁺) for $C_{15}H_{16}F_2N_2O_4S$
¹H-NMR(DMSO-d₆) δ: 2.87 (m, 2H); 3.26 (d, 2H); 3.37 (m, 2H); 3.86 (t, 1H); 3.96 (brs, 2H); 4.25 (dd, 1H); 4.98 (m, 1H); 5.78 (m, 1H); 7.38 (d, 2H); 8.26 (brs, 3H).

EXAMPLE 4

(5R)-3-[4-(1,1-Dioxo-3,6-dihydro-2H-thiopyran-4-yl)-3,5-difluorophenyl]-5-[(4-butyl)-1,2,3-triazol-1-yl)methyl]oxazolidin-2-one

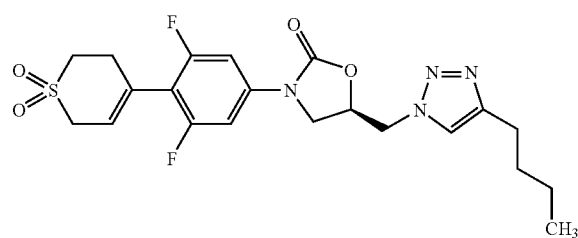

(5S)-3-[4-(1,1-Dioxo-3,6-dihydro-2H-thiopyran-4-yl)-3,5-difluorophenyl]-5-(aminomethyl)-oxazolidin-2-one (Intermediate 3) (20.7 mg, 0.057 mmol), N'-[(1E)-1-(dichloromethyl)pentylidene]-4-methylbenzenesulfonohydrazide (Intermediate 4) (25 mg, 0.074 mmol) and diisopropylethylamine (0.03 ml, 0.171 mmol) were reacted as described for Example 3. Chromatography on silica gel with 5% methanol in dichloromethane gave the title compound (16.6 mg).
MS (APPI): 465.9 (MH⁻) for $C_{21}H_{24}F_2N_4O_4S$
¹H-NMR(DMSO-d₆) δ: 0.87 (m, 3H); 1.26 (m, 2H); 1.53 (m, 2H); 2.60 (t, 2H); 2.85 (s, 2H); 3.36 (m, 2H); 3.89 (m, 1H); 3.95 (s, 2H); 4.24 (dd, 1H); 4.77 (m, 2H); 5.17 (m, 1H); 5.76 (s, 1H); 7.30 (d, 2H); 7.89 (s, 1H).

Intermediate 4: N'-[(1E)-1-(dichloromethyl)pentylidene]-4-methylbenzenesulfonohydrazide

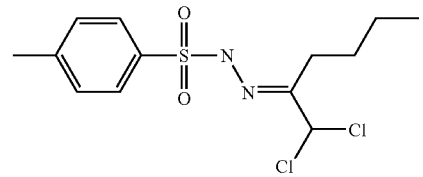

1,1-Dichlorohexan-2-one (Intermediate 5) (45.3 mg, 0.27 mmol) and 4-methylbenzenesulfonohydrazide (50 mg, 0.27 mmol) were added to propionic acid (0.5 ml) and then heated to 60° C. for 4 hours. The reaction mixture was then heated to 100° C. for 5 minutes and allowed to cool to room temperature overnight. Hexanes (20 ml) were added and the precipitate was filtered under nitrogen to yield the title compound (39.5 mg).
¹H-NMR(DMSO-d₆) δ: 0.94 (m, 3H); 1.41 (m, 2H); 1.57 (m, 2H); 1.62 (s, 1H); 2.40 (m, 2H); 2.46 (s, 3H); 6.18 (s, 1H); 7.35 (m, 2H); 7.82 (m, 2H).

Intermediate 5: 1,1-Dichlorohexan-2-one

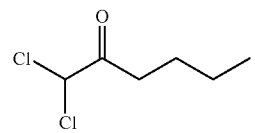

Magnesium (727 mg, 29.9 mmol) was added to anhydrous ether and cooled to 0° C. 1-Bromobutane (3.9 g, 28.5 mmol) was added and the mixture was agitated to form the Grignard reagent. 2,2-Dichloro-N-methoxy-N-methylacetamide (Intermediate 6) (5 g, 27.2 mmol) was then added and the reaction was allowed to stir at room temperature overnight. The ether was removed in vacuo and then the oil was purified by distillation at 90° C. under 3 Torr of vacuum.
¹H-NMR(DMSO-d₆) δ: 0.89 (m, 3H); 1.31 (m, 2H); 1.55 (m, 2H); 2.77 (m, 2H).

Intermediate 6: 2,2-Dichloro-N-methoxy-N-methylacetamide

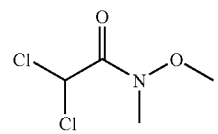

N,O-Dimethylhydroxylamine hydrochloride (7.94 g, 81.4 mmol) and K₂CO₃ (17.2 g, 124.1 mmol) were added to a water (70 ml) and toluene (70 ml) mixture. The mixture was then cooled to 0° C. Dichloroacetyl chloride (10 g, 67.85 mmol) was added drop wise and the reaction was allowed to warm to room temperature overnight. The toluene was collected and then the aqueous layer was extracted with EtOAc

EXAMPLE 5

(5R)-3-[4-(1,1-Dioxo-3,6-dihydro-2H-thiopyran-4-yl)-3-fluorophenyl]-5-[(4-ethyl)-1,2,3-triazol-1-ylmethyl]oxazolidin-2-one

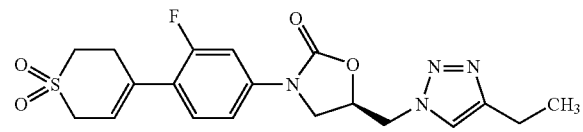

(5S)-3-[4-(1,1-Dioxo-3,6-dihydro-2H-thiopyran-4-yl)-3,5-difluorophenyl]-5-(aminomethyl)-oxazolidin-2-one (Intermediate 7) (85.5 mg, 0.25 mmol), N-[(1E)-1-(dichloromethyl)propylidene]4-methylbenzenesulfonohydrazide (Intermediate 8) (10 mg, 0.32 mmol) and diisopropylethylamine (0.13 ml, 0.7 mmol) were reacted as described for Example 3. Chromatography on silica gel with 5% methanol in dichloromethane gave the title product (71 mg).

MS (APPI): 421.30 (MH$^+$) for $C_{19}H_{20}F_2N_4O_4S$ $^1$H-NMR(DMSO-d$_6$) δ: 1.17 (m, 3H); 2.60 (m, 2H); 2.97 (m, 2H); 3.57 (m, 2H); 3.90 (m, 3H); 4.25 (m, 1H); 4.76 (d, 2H); 5.15 (m, 1H); 5.83 (s, 1H); 7.28 (d, 2H); 7.42 (m, 2H); 7.90 (s, 1H).

Intermediate 7: (5S)-3-[4-(1,1-Dioxo-3,6-dihydro-2H-thiopyran-4-yl)-3-fluorophenyl]-5-(aminomethyl)oxazolidin-2-one

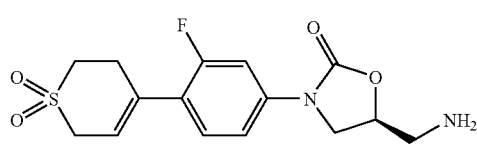

(5R)-3-[4-(1,1-Dioxo-3,6-dihydro-2H-thiopyran-4-yl)-3-fluorophenyl]-5-(azidomethyl) oxazolidin-2-one (Intermediate 2) (3 g, 8.2 mmol) was dissolved in acetonitrile/water (10:1, 50 ml). Triphenylphosphine (2.6 g, 9.9 mmol) was added and the resulting mixture was stirred over night with evolution of nitrogen. The reaction mixture was applied onto a silica gel column and eluted with acetonitrile/water (15:1 to 5:1) to give the title compound (2.67 g).

MS (ESP): 341 (MH$^+$) for $C_{15}H_{17}FN_2O_4S$ $^1$H-NMR (DMSO-d$_6$) (500 MHz) δ: 1.81 (brs, 2H); 2.81 (dd, 1H); 2.87 (dd, 1H); 2.98 (m, 2H); 3.30-3.38 (m, 2H); 3.89 (dd, 1H); 3.93 (m, 2H); 4.09 (dd, 1H); 4.65 (m, 1H); 5.84 (m, 1H); 7.37 (dd, 1H); 7.41 (dd, 1H); 7.54 (dd, 1H).

Intermediate 8: N'-[(1E)-1-(Dichloromethyl)pentylidene]4-methylbenzenesulfonohydrazide

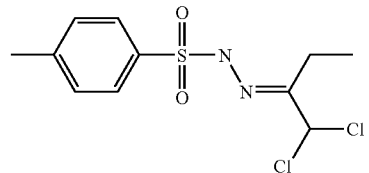

1,1-Dichlorobutan-2-one (CAS Registry Number 2648-56-8) (210 mg, 1.49 mmol) and 4-methylbenzenesulfonohydrazide (268 mg, 1.49 mmol) were added to propionic acid (3 ml), heated to 80° C. for 5 hours and then allowed to cool to room temperature overnight. Hexanes (20 ml) were added and the precipitate was filtered under nitrogen to yield the title compound (100 mg).

$^1$H-NMR(DMSO-d$_6$) δ: 1.21 (m, 3H); 2.46 (m, 5H); 6.19 (s, 1H); 7.36 (m, 2H); 7.83 (m, 3H).

EXAMPLE 6

(5R)-3-[4-(1,1-Dioxo-3,6-dihydro-2H-thiopyran-4-yl)-3-fluorophenyl]-5-[(4-methyl)-1,2,3-triazol-1-ylmethyl]oxazolidin-2-one

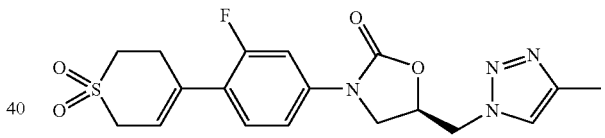

(5S)-3-[4-(1,1-Dioxo-3,6-dihydro-2H-thiopyran-4-yl)-3-fluorophenyl]-5-(aminomethyl) oxazolidin-2-one (Intermediate 7) (2.67 g, 7.8 mmol) was dissolved/suspended in dry methanol (100 ml). Diisopropylethyl amine (5.4 ml, 31 mmol) was added and it was cooled to 0° C. α,α-Dichloroacetone tosylhydrazone (2.9 g, 9.8 mmol) was added and the reaction mixture was stirred over night, whilst slowly to warm to room temperature. The solvent was removed under vacuum and the residue was dissoleved in dichloromethane and purified by chromatography on silica gel with acetone/hexanes (1:1 to 2:1) to give 2.04 g (64%) of the title compound as a colourless solid.

MS (ESP): 407.09 (MH$^+$) for $C_{18}H_{19}FN_4O_4S$ $^1$H-NMR (DMSO-d$_6$) (500 MHz) δ: 2.24 (s, 3H); 2.97 (m, 2H); 3.32-3.38 (m, 2H); 3.89-3.92 (m, 3H); 4.25 (dd, 1H, J 9.1, 9.1 Hz); 4.77 (d, 2H, J 5.2 Hz); 5.13 (m, 1H); 5.84 (m, 1H); 7.30 (dd, 1H, J 1.9, 8.6 Hz); 7.41 (dd, 1H J 8.6, 8.7 Hz); 7.47 (dd, 1H, J 1.9, 13.6 Hz); 7.89 (s, 1H).

EXAMPLE 7

(5R)-3-[3-Fluoro-4-(1-oxo-4-thiomorpholinyl)phenyl]-5-[(4-methyl-1,2,3-triazol-1-ylmethyl]oxazolidin-2-one

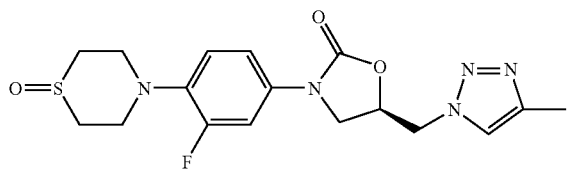

A solution of (5R)-3-[3-Fluoro-4-(1-oxo-4-thiomorpholinyl)phenyl]-5-(azidomethyl)-oxazolidin-2-one [Tokuyama, Ryukou; Takahashi, Yoshiei; Tomita, Yayoi; Tsubouchi, Masatoshi; Yoshida, Toshihiko; Iwasaki, Nobuhiko; Kado, Noriyuki; Okezaki, Eiichi; Nagata, Osamu; Chemical & Pharmaceutical Bulletin (2001), 49(4), 353-360] (1 g, 2.83 mmol) and 5,6,7,8-tetrachloro-1,4-dihydro-2,9-dimethyl-1,4-ethenonaphthalene (2.7 g, 8.49 mmol) in dioxane was heated at 105° C. for 48 hours. The solvent was evaporated in vacuo and the residue purified by chromatography on silica gel with 10% methanol in ethyl acetate to give the title compound (100 mg).

MS (ESP): 394.44 (MH$^+$) for $C_{17}H_{20}FN_5O_3S$ $^1$H-NMR(DMSO-d$_6$) δ: 2.24 (s, 3H); 2.86 (dd, 2H); 3.04 (m, 2H); 3.19 (m, 2H); 3.53 (t, 2H); 3.85 (dd, 1H); 4.21 (t, 1H); 4.76 (d, 2H); 5.09 (m, 1H); 7.15 (dd, 1H); 7.21 (t, 1H); 7.44 (dd, 1H); 7.88 (s, 1H).

EXAMPLE 8

(5R)-3-[4-(1,1-Dioxo-4-thiomorpholinyl)-3-fluorophenyl]-5-[(4-methyl-1,2,3-triazol-1-ylmethyl] oxazolidin-2-one

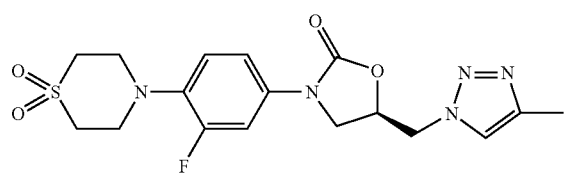

Osmium tetroxide (0.132 ml of a 2.5 wt % solution in 2-methyl-2-propanol) was added dropwise to a mixture of (5R)-3-[3-Fluoro-4-(1-oxo-4-thiomorpholinyl)phenyl]-5-[(4-methyl-1,2,3-triazol-1-ylmethyl]oxazolidin-2-one (Example 9) (1.1 g, 2.9 mmol) and 4-methylmorpholine N-oxide (1.02 g, 8.7 mmol) in a solution of 25% water in acetone (40 ml) at room temperature. The reaction mixture was allowed to stir for 72 hours. It was quenched with saturated sodium bisulfite (50 ml) and the mixture extracted into dichloromethane (5×100 ml). The combined organic layers were washed with saturated sodium bisulfite (100 ml) and with brine (100 ml), dried over sodium sulfate and concentrated. The residue was purified by chromatography on silica gel with 10% methanol in ethyl acetate to give title compound (0.55 g).

MS (ESP): 410.27 (MH$^+$) for $C_{17}H_{20}FN_5O_4S$ $^1$H-NMR (DMSO-d$_6$) δ: 2.24 (s, 3H); 3.27 (m, 4H); 3.47 (m, 4H); 3.85 (dd, 1H); 4.21 (dd, 1H); 4.75 (d, 2H); 5.10 (m, 1H); 7.15 (dd, 1H); 7.22 (t, 1H); 7.45 (dd, 1H); 7.88 (s, 1H).

EXAMPLE 9

(5R)-3-[3,5-Difluoro-4-(1-oxo-4-thiomorpholinyl) phenyl]-5-[4-methyl-1,2,3-triazol-1-ylmethyl]oxazolidin-2-one

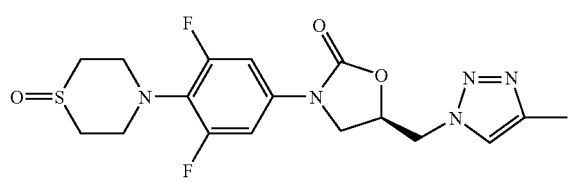

A suspension of (5R)-3-[3,5-difluoro-4-(1-oxo-4-thiomorpholinyl)phenyl]-5-(azidomethyl)-oxazolidin-2-one (Intermediate 9) (3.0 g, 8.1 mmol) and polystyrene triphenylphosphine (16 g, 24.2 mmol) in a mixture of dichloromethane/methanol/water (90:48:6 ml) were stirred at room temperature for 48 hours. After filtration, the polymer was washed with 10% methanol in dichloromethane (3×150 ml). The filtrate and washings were combined and concentrated to dryness to give desired amine (3.2 g), which was used directly for the next step. This amine, (5S)-5-(aminomethyl)-3-[3,5-difluoro-4-(1-oxo-4-thiomorpholinyl)-phenyl]-2-oxazolidinone, (3.0 g, 8.7 mmol) was reacted with diisopropylethylamine (6 ml, 34.8 mmol) and α,α-dichloroacetone tosylhydrazone (5.1 g, 17.4 mmol) as described for Example 3. Chromatography on silica gel eluting with 5% methanol in dichloromethane to give the title compound (2.2 g).

MS (ESP): 412.02 (MH$^+$) for $C_{17}H_{19}F_2N_5O_3S$ $^1$H-NMR (DMSO-d$_6$) δ: 2.23 (s, 3H); 2.89 (dd, 2H); 3.01 (m, 4H); 3.72 (dd, 2H); 3.81 (dd, 1H); 4.19 (dd, 1H); 4.72 (d, 2H); 5.11 (m, 1H); 7.26 (d, 2H); 7.88 (s, 1H).

Intermediate 9: (5R)-5-(Azidomethyl)-3-[3,5-difluoro-4-(1-oxo-4-thiomorpholinyl) phenyl]-2-oxazolidinone

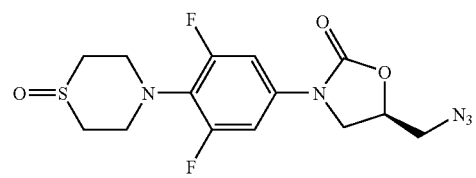

and

Intermediate 10: (5R)-5-(Azidomethyl)-3-[4-(1,1-Dioxo-4-thiomorpholinyl)-3,5-difluorophenyl]-2-oxazolidinone

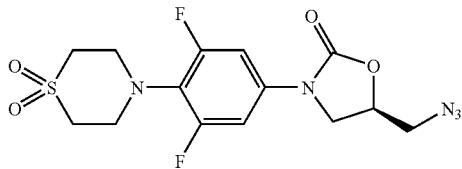

A suspension of (5R)-3-[3,5-difluoro-4-(1,1-dioxo-4-thiomorpholinyl) phenyl]-5-(azidomethyl)-oxazolidin-2-one (0.82 g, 2.11 mmol) and polystyrene triphenylphosphine (5.6 g, 8.5 mmol) in a mixture of dichloromethane/methanol/water (45:24:3 ml) was stirred at room temperature for 15 hours. After filtration, the polymer was washed with 10% methanol in dichloromethane (3×50 ml). The filtrates and washings were combined and concentrated to dryness to give desired amine (0.65 g), which was used directly for the next step.

Osmium tetroxide (3 ml of a 2.5 wt % solution in 2-methyl-2-propanol) was added dropwise to a mixture of (5R)-3-[3,5-difluoro-4-(4-thiomorpholinyl)phenyl]-5-(azidomethyl)-oxazolidin-2-one (Intermediate 11) (8.8 g, 24.8 mmol) and 4-methylmorpholine N-oxide (12.0 g, 102.6 mmol) in a solution of 25% water in acetone (200 ml) at room temperature. The reaction mixture was allowed to stir for 48 hours. Workup and chromatography as described for Example 8 gave the sulfoxide (4.0 g) and sulfone (3.8 g) title compounds.

Analytical data for Intermediate 9:
MS (ESP): 372.10 (MH$^+$) for $C_{14}H_{15}F_2N_5O_3S$
$^1$H-NMR(DMSO-d$_6$) δ: 2.74 (m, 2H); 2.94 (m, 4H); 3.75 (m, 5H); 4.11 (t, 1H); 4.91 (m, 1H); 7.31 (s, 1H); 7.36 (s, 1H).

Analytical data for Intermediate 10:
MS (ESP): 388.37 (MH$^+$) for $C_{14}H_{15}F_2N_5O_3S$
$^1$H-NMR (DMSO-d$_6$)δ: 3.22 (m, 4H); 3.48 (m, 4H); 3.75 (m, 3H); 4.11 (t, 1H); 4.92 (m, 1H); 7.32 (s, 1H); 7.37 (s, 1H).

Intermediate 11: (5R)-3-[3,5-Difluoro-4-(4-thiomorpholinyl)phenyl]-5-(azidomethyl)-oxazolidin-2-one

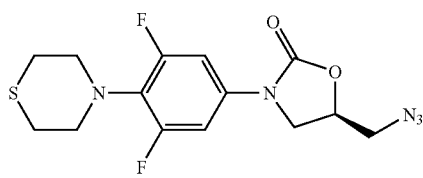

(5R)-3-[3,5-difluoro-4-(4-thiomorpholinyl)phenyl]-5-(hydroxymethyl)-oxazolidin-2-one (Intermediate 12) (15 g, 45.5 mmol) was dissolved in a mixture of triethylamine (9.6 ml, 68 mmol) and dichloromethane (200 ml). The resulting solution was cooled to 0° C. and methane sulfonyl chloride (4.6 ml, 59 mmol) was added. The reaction mixture was stirred at 0° C. for 2 hours then allowed to warm to room temperature. Water (200 ml) was added and then the organic layer separated, dried over magnesium sulfate, filtered and concentrated in vacuo. This intermediate was dissolved in dry DMF (120 ml). Sodium azide (11.8 g, 181 mmol) was added and the reaction mixture stirred at 70° C. overnight. It was diluted with dichloromethane (700 ml), washed with water (200 ml) and brine (200 ml) and dried over magnesium sulfate. Concentration in vacuo gave 16 g of the title compound.

MS (ESP): 356.37 (MH$^+$) for $C_{14}H_{15}F_2N_5O_2S$

Intermediate 12: (5R)-3-[3,5-Difluoro-4-(4-thiomorpholinyl)phenyl]-5-(hydroxymethyl)oxazolidin-2-one

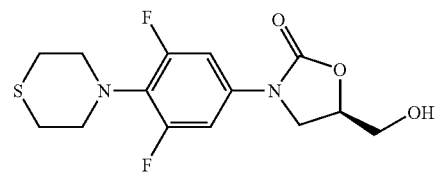

N-(3,5-Difluoro-4-thiomorpholin-4-yl-phenyl)-carbamic acid benzyl ester (WO 0232857 A1; WO 0198297 A2) (31.5 g, 86.4 mmol), lithium biS(trimethylsilyl)amide solution (95 ml, 1 M in THF) and (R)-(−)-glycidyl butyrate (14.5 g, 79.7 mmol) were reacted as described for Intermediate 25 to give the crude title compound (19.4 g).

$^1$H-NMR (DMSO-d$_6$) δ: 2.6-2.8 (m, 4H); 3.2-3.3 (m, 4H); 3.48-3.58 (m, 1H); 3.62-3.70 (m, 1H); 3.79 (dd, 1H); 4.04 (dd, 1H); 4.60-4.80 (m, 1H); 5.22 (t, 1H); 7.25-7.40 (m, 2H).

EXAMPLE 10

(5R)-3-[4-(1,1-Dioxo-4-thiomorpholinyl)-3,5-difluorophenyl]-5-[(4-methyl-1,2,3-triazol-1-yl)methyl]oxazolidin-2-one

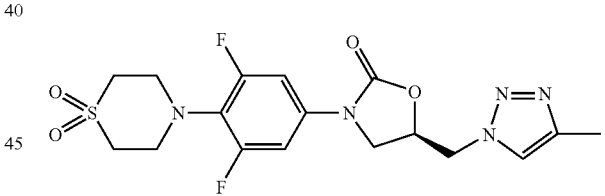

A suspension of (5R) 3-[3,5-difluoro-4-(1,1-dioxo-4-thiomorpholinyl)phenyl]-5-(azidomethyl)-oxazolidin-2-one (Intermediate 10) (0.82 g, 2.11 mmol) and polystyrene triphenylphosphine (5.6 g, 8.5 mmol) was reacted as described for Example 9 to give the intermediate amine, (5R)-3-[4-(1,1-Dioxo-4-thiomorpholinyl)-3,5-difluorophenyl]-5-(aminomethyl)-oxazolidin-2-one (0.65 g), which was used directly for the next step. This amine (0.63 g, 1.75 mmol) was reacted with diisopropylethylamine (0.9 ml, 5.2 mmol) and α,α-dichloroacetone tosylhydrazone (0.77 g, 2.62 mmol) as described for Example 3. Chromatography on silica gel eluting with 5% methanol in dichloromethane gave the title compound (350 mg).

MS (ESP): 428.04 (MH$^+$) for $C_{17}H_{19}F_2N_5O_4S$
$^1$H-NMR (DMSO-d$_6$) δ: 2.24 (s, 3H); 3.20 (m, 4H); 3.46 (m, 4H); 3.85 (dd, 1H); 4.19 (t, 1H); 4.73 (d, 2H); 5.11 (m, 1H); 7.29 (d, 2H); 7.88 (s, 1H).

EXAMPLE 11

(5R)-3-[4-(1,1-Dioxo-tetrahydro-2H-thiopyran-4-yl)-3-fluorophenyl]-5-[4-methyl-1,2,3-triazol-1-ylmethyl]oxazolidin-2-one

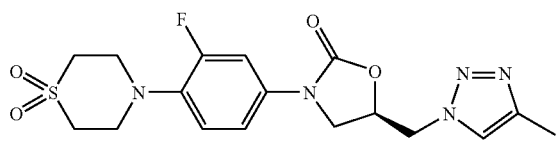

(5S)-3-[4-(1,1-dioxotetrahydro-2H-thiopyran-4-yl)-3-fluorophenyl]-5-(aminomethyl)-oxazolidin-2-one (WO 9854161 A1) (0.723 g, 2.11 mmol) was reacted with diisopropylethylamine (1.47 ml, 8.44 mmol) and α,α-dichloroacetone tosylhydrazone (0.78 g, 2.64 mmol) as described for Example 3. Chromatography on silica gel with 0% to 3% methanol in dichloromethane gave 0.456 g (53%) of the title compound as a white solid.

MS (APCI): 409.10 (MH$^+$) for $C_{18}H_{21}FN_4O_4S$

NMR (DMSO-d$_6$) δ: 2.06 (d, 2H); 2.16 (q, 2H); 2.24 (s, 3H); 3.12 (d, 2H); 3.21 (t, 1H); 3.39 (t, 2H); 3.88 (dd, 1H); 4.23 (t, 1H); 4.76 (d, 2H); 5.12 (m, 1H); 7.24 (dd, 1H); 7.39 (t, 1H); 7.43 (dd, 1H); 7.88 (s, 1H).

EXAMPLE 12

(5R)-3-[4-(1,1-Dioxo-2,5-dihydrothien-3-yl)-3-fluorophenyl]-5-[4-methyl-1,2,3-triazol-1-ylmethyl]oxazolidin-2-one

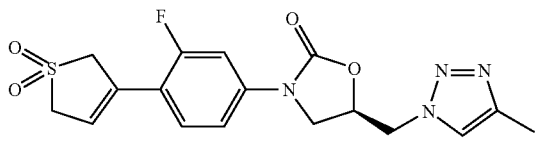

(5R)-3-(3-Fluoro-4-iodophenyl)-5-[4-methyl-1,2,3-triazol-1-ylmethyl]oxazolidin-2-one (Intermediate 13) (200 mg, 0.50 mmol) and copper (I) iodide (39 mg, 0.20 mmol) were dissolved in dry 1-methyl-2-pyrrolidinone (2 ml) and the reaction mixture placed under an atmosphere of argon. TetrakiS(triphenylphosphine)palladium(0) (35 mg, 0.05 mmol) was added, followed by a solution of tributyl(1,1-dioxo-2,5-dihydrothien-3-yl)stannane [Bew, Sean P.; Sweeney, J. B., Synthesis (1994), (7), p698] (263 mg, 0.65 mmol) in 1-methyl-2-pyrrolidinone (2 ml) and the reaction mixture stirred for 5 days at 40° C. Aqueous potassium fluoride 1M (150 ml) and ethyl acetate (150 ml) were added and the insoluble materials filtered off. The ethyl acetate layer was separated, dried over magnesium sulphate, filtered then concentrated in vacuo onto Isolute HM-N (2 g). Purification by chromatography on silica gel with 1.5% methanol in dichloromethane gave 20 mg (10%) of the desired compound.

MS (ESP): (MH)$^+$ 393.0 for $C_{17}H_{17}FN_4O_4S$

NMR (DMSO-d$_6$) δ: 2.24 (s, 3H); 3.92 (dd, 1H); 4.10 (m, 2H); 4.27 (dd, 1H); 4.30 (br s, 2H); 4.77 (d, 2H); 5.15 (m, 1H); 6.53 (t, 1H); 7.32 (dd, 1H); 7.50-7.55 (m, 2H); 7.88 (s, 1H).

Intermediate 13: (5R)-3-(3-Fluoro-4-iodophenyl)-5-[(4-methyl-1H-1,2,3-triazol-1-yl)methyl]-1,3-oxazolidin-2-one

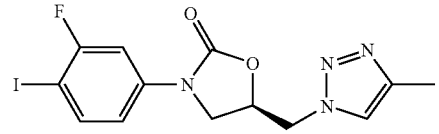

Silver trifluoroacetate (0.52 g, 2.35 mmol) was added to a solution of (5R)-3-(3-fluorophenyl)-5-[(4-methyl-1H-1,2,3-triazol-1-yl)methyl]-1,3-oxazolidin-2-one (Intermediate 14) (0.50 g, 1.81 mmol) in dichloromethane (15 ml). Iodine (0.55 g, 2.17 mmol) was added over 1.5 hours, and it was stirred overnight. After 16 hours, the solids were removed by filtration and additional silver trifluoroacetate (0.38 g, 1.72 mmol) and iodine (0.27 g, 1.06 mmol) were added. After and additional 24 hours, the reaction mixture was filtered. The filter cake was washed with methanol. The methanol filtrate was concentrated under vacuum to give 0.31 g of the title product.

MS (ESP): 403 (MH$^+$) for $C_{13}H_{12}FIN_4O_2$ $^1$H-NMR (DMSO-d$_6$) δ: 2.24 (s, 3H); 3.89 (dd, 1H); 4.23 (dd, 1H); 4.76 (d, 2H); 5.12 (m, 1H); 7.17 (dd, 1H); 7.51 (dd, 1H); 7.84 (dd, 1H); 7.88 (s, 1H).

Intermediate 14: (5R)-3-(3-Fluorophenyl)-5-[(4-methyl-1,2,3-triazol-1-yl)methyl]-oxazolidin-2-one

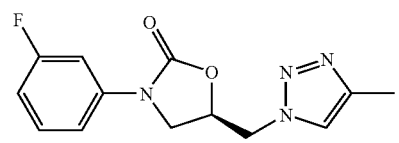

(5S)-5-(Aminomethyl)-3-(3-fluorophenyl)-1,3-oxazolidin-2-one (WO 0194342) (0.77 g, 3.57 mmol), α,α-dichloroacetone tosylhydrazone (1.28 g, 4.58 mmol) and N,N-diisopropylethylamine (3.20 ml, 18.35 mmol) were reacted as described for Example 3. Chromatographed on silica gel with 2% methanol in dichloromethane gave 0.71 g of the title product.

MS (ESP): 277 (MH$^+$) for $C_{13}H_{13}FN_4O_2$ $^1$H-NMR (DMSO-d$_6$) δ: 2.24 (s, 3H); 3.90 (dd, 1H); 4.25 (t, 1H); 4.77 (d, 2H); 5.13 (m, 1H); 6.99 (m, 1H); 7.28 (d, 1H); 7.42-7.48 (m, 2H); 7.89 (s, 1H).

EXAMPLE 13

(5R)-3-[3-Fluoro-4-(4-bromo-1H-imidazol-1-yl)phenyl]-5-[4-methyl-1,2,3-triazol-1-ylmethyl]oxazolidin-2-one

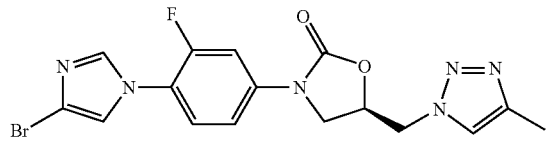

(5S)-5-(Aminomethyl)-3-[4-(4-bromo-1H-imidazol-1-yl)-3-fluorophenyl-oxazolidin-2-one (Intermediate 15) (0.35 g, 0.985 mmol), diisopropylethylamine (0.21 ml, 1.23 mmol) and α,α-dichloroacetone tosylhydrazone (0.33 g, 1.18 mmol) were reacted as described for Example 3. Chromatography on silica gel with 0-10% methanol in methylene chloride gave 0.34 g (83%) of the title compound as a white solid.

MS (APCI): 421.0, 423.0 (MH$^+$) for $C_{16}H_{14}BrFN_6O_2$ $^1$H-NMR(DMSO-d$_6$) δ: 2.21 (s, 3H); 3.92 (dd, 1H); 4.27 (dd, 1H); 4.76 (d, 2H); 5.14 (m, 1H); 7.41 (dd, 1H); 7.66 (dd, 1H); 7.68 (dd, 1H); 7.74 (m, 1H); 7.87 (s, 1H); 8.01 (s, 1H).

Intermediate 15: (5S)-5-(Aminomethyl)-3-[4-(4-bromo-1H-imidazol-1-yl)-3-fluorophenyl-1,3-oxazolidin-2-one

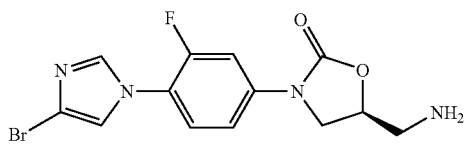

N-({(5S)-3-[4-(4-Bromo-1H-imidazol-1-yl)-3-fluorophenyl]-2-oxo-1,3-oxazolidin-5-yl}methyl)acetamide (WO 9731917 A1) (7.5 g, 18.9 mmol) was dissolved in methanol (25 ml) and aqueous HCl solution (6M, 25 ml). It was refluxed for 14 hours, cooled to room temperature, concentrated in vacuo and basified using solid sodium carbonate. The mixture was extracted with ethyl acetate (4×150 ml), dried over magnesium sulfate, concentrated in vacuo, and dried under high vacuum to give the title product (4.65 g, 13.1 mmol). This product was carried on to the next reaction without further purification.

MS (ESP): 355.24 and 357.25 (MH$^+$) for $C_{13}H_{12}brFN_4O_2$ $^1$H-NMR(DMSO-d$_6$) δ: 1.60 (s, 2H); 2.82 (m, 2H); 3.90 (m, 1H); 4.10 (m, 1H); 4.65 (m, 1H); 7.48 (dd, 1H); 7.67 (m, 1H); 7.74 (m, 1H); 7.77 (m, 1H); 8.01 (m, 1H).

EXAMPLE 14

(5R)-3-[3-Fluoro-4-(4-methyl-1,2,3-triazol-1-yl)phenyl]-5-[(4-methyl-1,2,3triazol-1-yl)methyl]oxazolidin-2-one

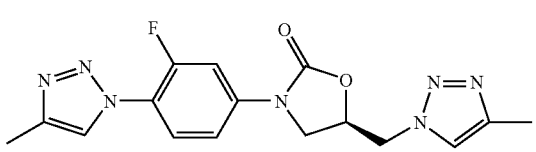

(5S)-5-(Aminomethyl)-3-[3-Fluoro-4-(4-methyl-1,2,3-triazol-1-yl)phenyl]-1,3-oxazolidin-2-one (Intermediate 15) (1 g, 3.4 mmol) was reacted with diisopropyl ethylamine (2.34 ml, 13.6 mmol) and α,α-Dichloroacetone tosylhydrazone (1.2 g, 4.12 mmol) as described for Example 6. Chromatography on silica gel with 1% methanol in dichloromethane gave the title product (0.45 g).

MS (ESP): 358 (MH$^+$) for $C_{16}H_{16}FN_7O_2$ $^1$H-NMR (DMSO-d$_6$) δ: 2.25 (s, 3H); 2.36 (s, 3H); 3.97 (m, 1H); 4.32 (t, 1H); 4.8 (d, 2H); 5.17 (m, 1H); 7.51 (dd, 1H); 7.75 (dd, 1H); 7.83 (t, 1H); 7.90 (s, 1H); 8.31 (s, 1H).

Intermediate 16: (5S)-5-(Aminomethyl)-3-[3-Fluoro-4-(4-methyl-1,2,3-triazol-1-yl)phenyl]-1,3-oxazolidin-2-one

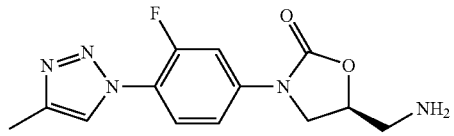

(5R) 3-[3-Fluoro-4-(4-methyl-1,2,3-triazol-1-yl)phenyl]-5-(azidomethyl)-oxazolidin-2-one (Intermediate 17) (2.0 g, 6.30 mmol) was dissolved in methanol/ethyl acetate (50 ml, 1:1) and hydrogenated over palladium on carbon (10%, 0.2 g) at room temperature and normal pressure for 4 hours. The resulting mixture was filtered through the celite and concentrated under reduced pressure to give 1.02 g of the title compound as a solid, which was used without further purification in the next step.

MS (ESP): 292 (MH$^+$) for $C_{13}H_{14}FN_5O_2$

Intermediate 17: (5R)-5-(Azidomethyl)-3-[3-Fluoro-4-(4-methyl-1H-1,2,3-triazol-1-yl)phenyl]-1,3-oxazolidin-2-one

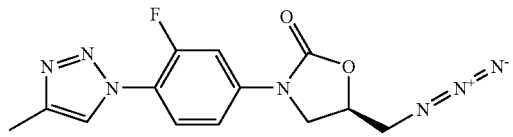

(5R)-3-[3-Fluoro-4-(4-methyl-1,2,3-triazol-1-yl)phenyl]-5-[(methanesulfonyl)methyl]-oxazolidin 2-one (Intermediate 18) (5.0 g, 13.5 mmol) was dissolved in DMF (45 ml). Sodium azide (1.75 g, 27.0 mmol) was added and the reaction mixture was stirred at 70° C. for one hour. It was partitioned between ethyl acetate and saturated sodium bicarbonate, the organic phase was washed with water and brine, dried over magnesium sulfate and concentrated under reduced pressure to give the product as a white solid (4.1 g), which was used without further purification.

MS (ESP): 318 (MH$^+$) for $C_{13}H_{12}FN_7O_2$ $^1$H-NMR (DMSO-d$_6$) δ: 2.36 (s, 3H); 3.82 (m, 2H); 3.89 (dd, 1H); 4.24 (dd, 1H); 4.98 (m, 1H); 7.56 (dd, 1H); 7.84 (m, 2H); 8.30 (s, 1H).

Intermediate 18: (5R)-3-[3-Fluoro-4-(4-methyl-1,2,3-triazol-1-yl)phenyl]-5-[methanesulfonylmethyl]oxazolidin 2-one

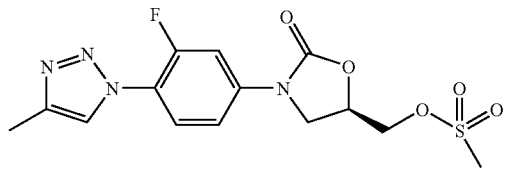

(5R)-3-[3-Fluoro-4-(4-methyl-1H-1,2,3-triazol-1-yl)phenyl]-5-(hydroxymethyl)oxazolidin-2-one (Intermediate 19) (4.0 g, 13.7 mmol) was dissolved in dichloromethane (30 ml) and cooled to 0° C. Triethylamine (3.08 ml, 23.3 mmol) was added, followed by methylsulfonyl chloride (1.27 ml, 16.4 mmol). It was stirred for one hour and poured into saturated aqueous sodium bicarbonate solution and diluted with dichloromethane (200 ml). The organic phase was dried over magnesium sulfate and solvent was removed under reduced pressure to give the title product (5.1 g) as a solid, which was used without further purification.

MS (ESP): 371 (MH$^+$) for $C_{14}H_{15}FN_4O_5S$

Intermediate 19: (5R)-3-[3-Fluoro-4-(4-methyl-1,2,3-triazol-1-yl)phenyl]-5-(hydroxymethyl)oxazolidin-2-one

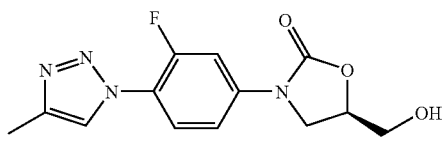

[3-Fluoro-4-(4-methyl-[1,2,3]-triazol-1-yl)-phenyl]-carbamic acid benzyl ester (Intermediate 20) (56 g, 0.17 mol), lithium hexamethyldisilazide (LiHMDS) (1M/THF, 200 ml, 0.20 mol) and R-(−)-glycidyl butyrate (25 ml, 0.18 mol) were reacted following the procedure described for Intermediate 25. Chromatography on silica gel with 0-40% acetone in ethyl acetate, followed by trituration with acetone/ethyl acetate/chloroform/hexanes (300 ml/100 ml/100 ml/500 ml) overnight gave the title compound as an off-white solid (33.9 g), m.p. 190.2-192.0° C.

$^1$H-NMR (DMSO-d$_6$) δ: 8.28 (d, 1H); 7.82 (m, 2H); 7.56 (dd, 1H); 5.25 (brs, 1H); 4.77 (m, 1H); 4.16 (dd, 1H); 3.91 (dd, 1H); 3.66 (m, 2H); 2.34 (s, 3H).

Intermediate 20: [3-Fluoro-4-(4-methyl-[1,2,3]triazol-1-yl)-phenyl]-carbamic acid benzyl ester

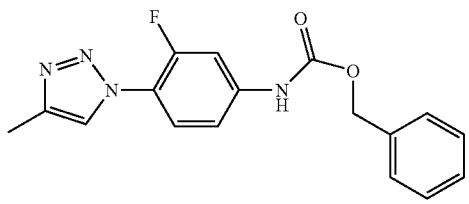

3-Fluoro-4-(4-methyl-[1,2,3]triazol-1-yl)-phenylamine (Intermediate 21) (34.8 g, 0.181 mol) and benzyl chloroformate (34 mL, 0.238 mol) were reacted following the procedure for Intermediate 26. The crude product obtained by filtration was dried in vacuo and triturated with chloroform/hexanes (250 ml/500 ml) to give the title compound as a colourless solid (56 g).

$^1$H-NMR (CDCl$_3$) δ: 7.84 (dd, 1H); 7.77 (dd, 1H); 7.70 (dd, 1H); 7.41 (m, 5H); 7.09 (m, 1H); 6.85 (brs, 1H); 5.23 (s, 2H); 2.44 (d, 3H).

Intermediate 21: 3-Fluoro-4-(4-methyl-[1,2,3]triazol-1-yl)-phenylamine

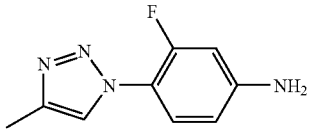

1-(2-Fluoro-4-nitro-phenyl)-4-methyl-[1,2,3]-triazole (Intermediate 22) (38.3 g, 0.173 mol) and SnCl$_2$ 2H$_2$O (200 g, 0.886 mol) were reacted as described for Intermediate 27 to give the crude title compound as a off-white solid (31.9 g), which was used directly for the next reaction.

$^1$H-NMR (CDCl$_3$) δ: 7.65 (dd, 1H); 7.57 (dd 1H); 6.53 (m, 2H); 2.43 (d, 3H).

Intermediate 22: 1-(2-Fluoro-4-nitro-phenyl)-4-methyl-[1,2,3]-triazole

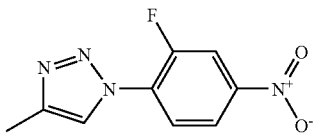

A mixture of 4-methyl-[1,2,3]-triazole (60 g, 0.72 mol), K$_2$HPO$_4$ (250 g, 1.44 mol) and 3,4-difluoronitrobenzene (80 ml, 0.723 mol) in DMF (3.4 litres) was stirred at 85° C. under N$_2$ for 2.5 days. After removal of DMF in vacuo, the residue was chromatographed on silica gel with 0-5% ethyl acetate in dichloromethane to give the title compound as a light yellow solid (38.3 g, 24%). The other two isomers were also isolated.

$^1$H-NMR (CDCl$_3$) δ: δ 8.35 (m, 1H); 8.23 (m, 2H); 7.98 (dd, 1H); 2.48 (d, 3H).

EXAMPLE 15

(5R)-3-[3-Fluoro-4-(3-methyl-1,2,4-triazol-1-yl)phenyl]-5-[(4-methyl-1,2,3-triazol-1-yl)methyl]oxazolidin-2-one

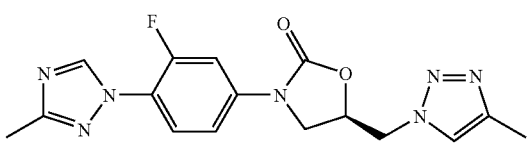

(5S)-5-(Aminomethyl)-3-[3-fluoro-4-(4-methyl-1,2,4-triazol-1-yl)phenyl]oxazolidin-2-one (Intermediate 23) (1.2 g, 4.1 mmol) was reacted with diisopropyl ethylamine (2.8 ml, 16.4 mmol) and α,α-dichloroacetone tosylhydrazone (1.5 g, 4.9 mmol) as described for Example 3. Chromatography on silica gel with 1% methanol in dichloromethane gave the title product (0.41 g).

MS (ESP): 358 (MH$^+$) for $C_{16}H_{16}FN_7O_2$ $^1$H-NMR (DMSO-d$_6$) δ: 2.25 (s, 3H); 2.38 (s, 3H); 3.96 (m, 1H); 4.30 (dd, 1H); 4.79 (d, 2H); 5.16 (m, 1H); 7.48 (dd, 1H); 7.73 (dd, 1H); 7.79 (dd, 1H); 7.90 (s, 1H); 8.84 (d, 1H).

Intermediate 23: (5S) 3-[3-Fluoro-4-(4-methyl-1,2,4-triazol-1-yl)phenyl]-5-(aminomethyl)-oxazolidin-2-one

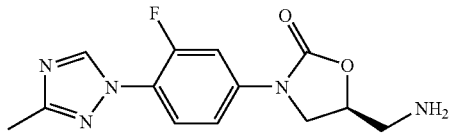

(5R) 3-[3-Fluoro-4-(3-methyl-1,2,4-triazol-1-yl)phenyl]-5-(azidomethyl)oxazolidin-2-one (Intermediate 24) (1.8 g, 5.67 mmol) was hydrogenated as described for Intermediate 16. Chromatography on silica gel with 3-7% methanol in dichloromethane gave the title compound (1.28 g).

MS (ESP): 292 (MH$^+$) for $C_{13}H_{14}FN_5O_2$ $^1$H-NMR (DMSO-d$_6$) δ: 1.63 (brs, 2H); 2.38 (s, 3H); 2.86 (m, 2H); 3.94 (dd, 1H); 4.13 (dd, 1H); 4.68 (m, 1H); 7.54 (dd, 1H); 7.79 (m, 2H); 8.83 (d, 1H).

Intermediate 24: (5R) 3-[3-Fluoro-4-(3-methyl-1,2,4-triazol-1-yl)phenyl]-5-(azidomethyl)-oxazolidin-2-one

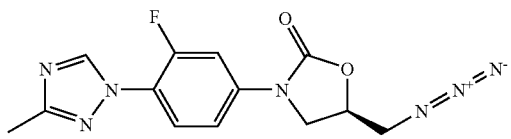

(5R)-3-[3-Fluoro-4-(3-methyl-1,2,4-triazol-1-yl)phenyl]-5-[(methanesulfonyl)methyl]-oxazolidin-2-one (Intermediate 24a) (5.432 g, 14.7 mmol), sodium azide (1.092 g, 16.6 mmol), and 18-crown-6 (0.069 g, 0.26 mmol) in dimethylformamide (15 mL) were heated to 90° C. for 3.75 hours. The reaction mixture was poured into water (200 ml) and extracted with dichloromethane (3×100 ml). The combined organic layers were washed once with brine, dried over MgSO$_4$ and concentrated under vacuum. Chromatography on silica gel with 5% methanol in dichloromethane gave the title compound (3.7 g) as a colourless solid.

MS (ES+): 318.34 (MH$^+$) for $C_{13}H_{12}FN_7O_2$ $^1$H-NMR (DMSO-d$_6$) δ: 2.35 (s, 3H); 3.75 (m, 2H); 3.83 (dd, 1H); 4.19 (dd, 1H); 4.93 (m, 1H); 7.51 (dd, 1H); 7.77 (m, 2H); 8.82 (d, 1H).

Intermediate 24A: (5R)-3-[3-Fluoro-4-(3-methyl-1,2,4-triazol-1-yl)phenyl]-5-[(methanesulfonyl)methyl]-oxazolidin-2-one

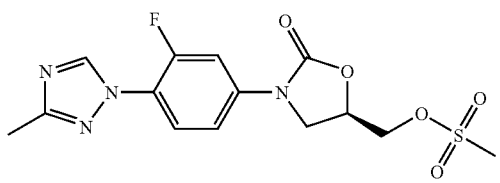

(5R)-3-[3-Fluoro-4-(3-methyl-1,2,4-triazol-1-yl)phenyl]-5-(hydroxymethyl)oxazolidin-2-one (Intermediate 25) (10.08 g, 34.5 mmol) in dichloromethane (100 ml) and triethylamine (6.0 ml, 43 mmol) was cooled to 0° C. and methanesulfonyl chloride (3.2 ml, 41 mmol) was added by syringe. The reaction mixture was allowed to warm to room temperature overnight. More pyridine (50 ml) was added and the reaction mixture was cooled to 0° C. before adding additional methanesulfonyl chloride (3.2 ml, 41 mmol). The reaction was allowed to warm to room temperature and the solid was collected by filtration and washed with ethyl acetate to afford the crude title compound (5.49 g).

MS (ES+): 371.23 (MH$^+$) for $C_{14}H_{15}FN_4O_5S$ $^1$H-NMR (DMSO-d$_6$) δ: 2.35 (s, 3H); 3.26 (s, 3H); 3.88 (dd, 1H); 4.24 (dd, 1H); 4.50 (m, 2H); 5.05 (m, 1H); 7.51 (dd, 1H); 7.76 (m, 2H); 8.82 (d, 1H).

Intermediate 25: (5R)-3-[3-Fluoro-4-(3-methyl-1,2,4-triazol-1-yl)phenyl]-5-(hydroxymethyl)oxazolidin-2-one

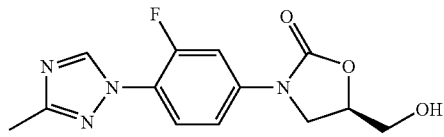

LiHMDS (1M in THF, 250 ml, 0.250 mol) was added drop wise to [3-Fluoro-4-(3-methyl-1,2,4-triazol-1-yl)phenyl]carbamic acid benzyl ester (Intermediate 26) (72.9 g, 0.224 mol) in anhydrous THF (1.35 l) at −78° C. under N$_2$. The resulting mixture was stirred for 30 minutes, R-(−)-glycidyl butyrate (32 ml, 0.226 mol) was then added, the mixture was allowed to warm to room temperature and stirred overnight. It was diluted with ethyl acetate (1 L) and water (250 ml). The organic layer was separated, washed with water (2×250 ml) and brine (2×250 ml), dried over sodium sulfate and concentrated in vacuo to ~400 ml. Hexanes (1 l) were added, the mixture was stirred overnight and the precipitate was collected by filtration, washed with hexanes and dried under vacuum to give the title compound as a colourless solid (52.3 g), m.p. 190.5-192.5° C.

$^1$H-NMR (DMSO-d$_6$) δ: 8.82 (d, 1H); 7.80 (m, 2H); 7.53 (dd, 1H); 5.25 (brs, 1H); 4.76 (m, 1H); 4.14 (dd, 1H); 3.89 (dd, 1H); 3.64 (dd, 2H).

Intermediate 26: [3-Fluoro-4-(3-methyl-1,2,4-triazol-1-yl)phenyl]carbamic acid benzyl ester

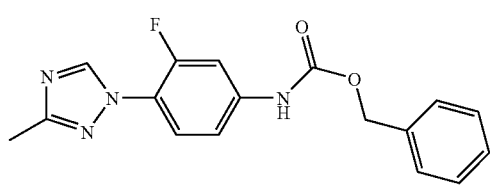

Saturated aqueous sodium hydrogencarbonate solution (375 ml) was added to a solution of 3-fluoro-4-(3-methyl-1,2,4-triazol-1-yl)phenylamine (Intermediate 27) (50.8 g, 0.265 mol) in THF (1 l). The mixture was cooled to −20° C. and benzyl chloroformate (48 ml, 0.336 mol) was added. The reaction mixture was stirred under N₂, allowed to warm to room temperature and stirred for 2 days. The mixture was concentrated to approximately half the volume and diluted with ethyl acetate (1 l). The organic layer was separated and washed with water (2×), brine (2×), dried over sodium sulfate and concentrated in vacuo. Recrystallisation from ethyl acetate/hexanes (300 ml/200 ml) gave the title compound (73.0 g), m.p. 152.6-154.9° C.

¹H-NMR (DMSO-d₆) δ: 10.27 (s, 1H); 8.77 (d, 1H); 7.66 (m, 2H); 7.41 (m, 6H); 5.19 (s, 2H); 2.35 (s, 3H).

Intermediate 27: 3-Fluoro-4-(3-methyl-1,2,4-triazol-1-yl)phenylamine

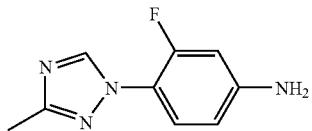

A mixture of 1-(2-Fluoro-4-nitro-phenyl)-3-methyl-1,2,4-triazole (Intermediate 28) (56.6 g, 0.255 mol) and SnCl₂2H₂O (292 g, 1.29 mol) in ethanol (800 ml) was stirred at 70° C. under N₂ for 1 hour. After cooling to room temperature, the reaction mixture was poured onto ice and the pH was made slightly basic by addition of NaHCO₃ (solid) and extracted with ethyl acetate (3×). The combined organic phase was washed with brine (2×), dried over sodium sulfate and concentrated in vacuo to give the title compound as a colourless solid (48.8 g).

¹H-NMR (CDCl₃) δ: 8.32 (d, 1H); 7.47 (dd, 1H); 6.49-6.54 (m, 2H); 3.94 (brs, 2H); 2.48 (s, 3H).

Intermediate 28: 1-(2-Fluoro-4-nitro-phenyl)-3-methyl-1,2,4-triazole

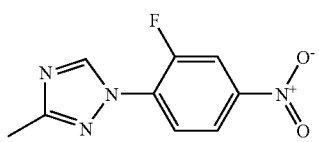

3-Methyl-1,2,4-triazole (34.5 g, 0.416 mol) and 3,4-difluoronitrobenzene (46 ml, 0.416 mol) were reacted as described for Intermediate 22. Chromatography on silica gel with 5-50% ethyl acetate in hexanes and recrystallisation from ethyl acetate/hexanes gave the title compound as light yellow crystals (41.3 g), m.p. 113.8° C.-114.3° C.

The other two isomers were also isolated.

¹H-NMR (CDCl₃) δ: 8.73 (d, 1H); 8.19~8.23 (m, 3H); 2.53 (s, 3H).

EXAMPLE 16

(5R)-3-[3-Fluoro-4-[(4-carbaldehyde oxime)-imidazol-1-yl]phenyl]-5-[(4-methyl-1,2,3-triazol-1-yl)methyl]oxazolidin-2-one

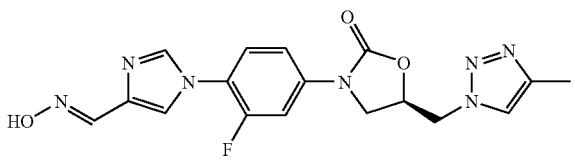

(5S)-3-[3-Fluoro-4-[(4-carbaldehyde oxime)-imidazol-1-yl]phenyl]-5-[aminomethyl]-oxazolidin-2-one (Intermediate 29) (1.18 g, 3.68 mmol) was slurried in 60 ml methanol and cooled with an ice water bath before adding diisopropylethylamine (2.6 ml, 15 mmol). N'-[2,2-dichloro-1-methylethylidene]4-methylbenzenesulfonohydrazide (1.30 g, 4.40 mmol) was added. The reaction was allowed to stir at 0° C. for 5 hours. The solvent was removed under vacuum and the residue was purified by flash chromatography on silica gel with a gradient of 7.5-10% methanol in dichloromethane to afford the title product (1.71 g).

MS (APCI): 386.2 (MH⁺) for C₁₇H₁₆FN₇O₃

¹H-NMR (DMSO-d₆) δ: 2.25 (s, 3H); 3.95 (dd, 1H); 4.31 (t, 1H); 4.79 (d, 2H); 5.17 (m, 1H); 7.45 (dd, 1H); 7.48 (s, 1H); 7.74 (m, 2H); 7.90 (s, 1H); 8.13 (d, 2H). 10.96 and 11.65 (oxime isomers, s, 1H).

Intermediate 29: (5S)-3-[3-Fluoro-4-[(4-carbaldehyde oxime)imidazol-1-yl]phenyl]-5-[aminomethyl]-oxazolidin-2-one

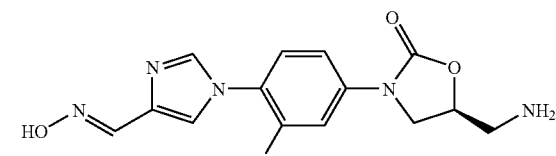

(5R) 3-[3-Fluoro-4-[(4-carboxaldehyde oxime)imidazol-1-yl]phenyl]-5-(azidomethyl)-oxazolidin-2-one (Intermediate 29A) (1.53 g, 4.44 mmol) was reacted with polystyrene triphenylphosphine (6.08 g, 9.2 mmol) like described for the amine under Example 9 to give the crude title compound (1.18 g).

MS (ES+): 320.33 (MH⁺) for C₁₄H₁₄FN₅O₃

¹H-NMR (MeOH-d₄) δ: 1.63 (s, 2H); 2.82 (m, 2H); 3.90 (dd, 1H); 4.09 (dd, 1H); 4.64 (m, 1H); 7.43 (s, 1H); 7.47 (dd, 1H); 7.71 (m, 2H); 8.07 (s, 1H); 8.10 (s, 1); 11.61 (s, 1H).

Intermediate 29A: (5R) 3-[3-Fluoro-4-[(4-carboxaldehyde oxime)imidazol-1-yl]phenyl]-5-(azidomethyl)-oxazolidin-2-one

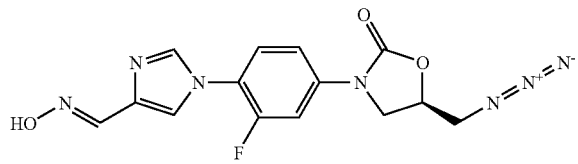

Hydroxylamine hydrochloride (1.23 g, 17.7 mmol) and potassium carbonate (1.47 g, 10.6 mmol) were added to a solution of (5R) 3-[3-Fluoro-4-[(4-carboxaldehyde)imidazol-1-yl]phenyl]-5-(azidomethyl)-oxazolidin-2-one (Intermediate 29B, 3.34 g, 10.1 mmol) in methanol (20 ml) and dichloromethane (20 ml). After 18 hours dichloromethane (200 ml) and water (100 ml) were added, the aqueous layer was extracted twice with dichloromethane and the combined organic layers were washed once with brine, dried over magnesium sulfate and concentrated under vacuum to afford the the title compound (1.53 g) as a solid.

MS (ES+): 346.27 (MH$^+$) for $C_{14}H_{12}FN_7O_3$

Intermediate 29B: (5R) 3-[3-Fluoro-4-[(4-carboxaldehyde)imidazol-1-yl]phenyl]-5-(azidomethyl)-oxazolidin-2-one

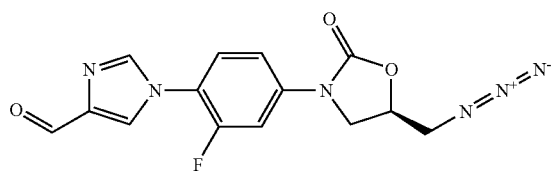

A solution of (5R) 3-[3-Fluoro-4-[(4-carboxaldehyde)imidazol-1-yl]phenyl]-5-[(methanesulfonyl)methyl]-oxazolidin-2-one (Intermediate 29C, 6.601 g, 17.2 mmol), sodium azide (1.37 g, 21 mmol) and 18-crown-6 (0.050 g, 0.19 mmol) were reacted as described for Intermediate 24. Aqueous workup afforded the crude title compound (3.35 g) as a colourless solid.

MS (ES+): 331.30 (MH$^+$) for $C_{14}H_{11}FN_6O_3$

Intermediate 29C: (5R) 3-[3-Fluoro-4-[(4-carboxaldehyde)imidazol-1-yl]phenyl]-5-[(methanesulfonyl)methyl]-oxazolidin-2-one

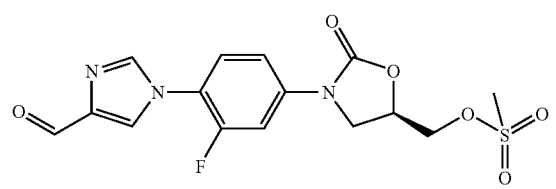

Triethylamine (3.0 ml, 22 mmol) was added to a slurry of (5R) 3-[3-Fluoro-4-[(4-carboxaldehyde)imidazol-1-yl]phenyl]-5-(hydroxymethyl)-oxazolidin-2-one (Intermediate 29D, 5.42 g, 17.8 mmol) in dichloromethane (100 ml). The reaction mixture was cooled to 0° C. before addition of methanesulfonyl chloride (2.45 g, 21.4 mmol) by syringe. The reaction mixture was allowed to warm to room temperature overnight. Dichloromethane was removed under vacuum and the solid remaining was triturated in a mixture of water (100 ml) and diethyl ether (100 ml). Filtration and washing the solid gave the crude title compound (6.62 g) as a tan solid, which was used without further purification.

MS (ES+): 384.23 (MH$^+$) for $C_{15}H_{14}FN_3O_6S$ $^1$H-NMR (DMSO-d$_6$) δ: 3.26 (s, 3H); 3.89 (dd, 1H); 4.25 (dd, 1H); 4.51 (m, 2H); 5.07 (m, 1H); 7.51 (dd, 1H); 7.79 (m, 2H); 8.26 (s, 1H); 8.45 (s, 1H); 9.82 (s, 1H).

Intermediate 29D: (5R) 3-[3-Fluoro-4-[(4-carboxaldehyde)imidazol-1-yl]phenyl]-5-(hydroxymethyl)-oxazolidin-2-one

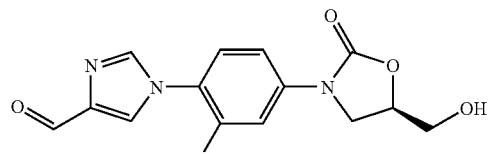

[3-Fluoro-4-[(4-dimethoxymethyl)imidazol-1-yl]phenyl]-carbamic acid benzyl ester (Intermediate 29E) (364.5 g, 0.946 mol) was dissolved in THF (6.4 L) at 44° C. under nitrogen. It was cooled to −78° C. and lithium bis-trimethylsilylamide (1M in THF, 995 ml) was added drop wise at such a rate that the temperature did not exceed −74° C. After addition stirring was continued for 40 minutes and then R-(−) glycidyl butyrate (144 g, 0.933 mol) was added drop wise during 20 minutes and it was stirred for an additional 3 hours and then at room temperature over night. Ethyl acetate (200 ml) was added and it was stirred for 30 minutes. The solvent was removed under reduced pressure, the residue taken up in water (4 L) and it was stirred for 1 hour. The resulting precipitate of the crude intermediate (5R) 3-[3-Fluoro-4-[(4-dimethoxymethyl)imidazol-1-yl]phenyl]-5-(hydroxymethyl)-oxazolidin-2-one was collected by filtration, washed with water and dissolved in THF/water (2.4 L, 5:1). Concentrated HCl (100 ml) was added and it was stirred at room temperature for 4 hours. THF was removed under reduced pressure, water (1.4 L) was added and the mixture was poured into a saturated aqueous solution of sodium hydrogencarbonate (4 L). It was stirred for 1 hour and left to stand over night. The precipitate was collected by filtration, washed with water dried under vacuum and recrystallized from ethyl acetate (3 L) to yield the title compound (148.8 g) as a colorless solid.

MS (ES+): 306.26 (MH$^+$) for $C_{14}H_{12}FN_3O_4$ $^1$H-NMR (DMSO-d$_6$) δ: 3.52-3.60 (m, 1H); 3.65-3.75 (m, 1H); 3.88 (dd, 1H); 4.14 (dd, 1H); 4.75 (m, 1H); 5.26 (m, 1H); 7.52 (m, 1H); 7.75 (dd, 1H); 7.80 (dd, 1H); 8.23 (s, 1H); 8.43 (s, 1H); 9.82 (s, 1H).

Intermediate 29E: [3-Fluoro-4-[(4-dimethoxymethyl) imidazol-1-yl]phenyl]-carbamic acid benzyl ester

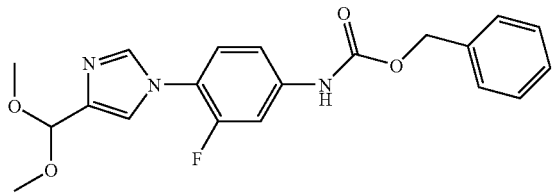

[3-Fluoro-4-[(4-dimethoxymethyl)imidazol-1-yl]phenylamine (Intermediate 29F) (251.7 g, 1.026 mol) was dissolved in THF (2 L) and cooled to −5° C. N-methylmorpholine (156.15 g, 1.544 mol) was added, followed by drop wise addition of benzyl chloroformate (227 g, 1.33 mol) at such a rate that the temperature was kept below 4° C. It was stirred for 2 hours and then allowed to reach room temperature over night. The reaction mixture was poured over water (5 L) and stirred for 1 hour. The precipitate was collected by filtration, washed with water and dried to give the title compound (385.2 g) as a solid.
$^1$H-NMR (DMSO-$d_6$) δ: 3.25 (s, 6H); 5.18 (s, 2H); 5.39 (s, 1H); 7.31-7.48 (m, 7H); 7.52-7.65 (m, 2H); 7.93 (s, 1H); 10.21 (s, 1H).

Intermediate 29F: [3-Fluoro-4-[(4-dimethoxymethyl) imidazol-1-yl]phenylamine

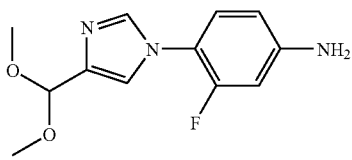

1-(2-Fluoro-4-nitro-phenyl)-4-(dimethoxymethyl)-1H-imidazol (Intermediate 29G) (110 g, 0.391 mol) was dissolved in methanol/water (1.65 L, 10:1), palladium on carbon (10%, 12 g) was added and it was brought to reflux. Hydrazine (50 ml) was added in portions and heating was continued for 1 hour. It was filtered, the solvent removed under vacuum and the residue was resuspended in ice water (800 ml) and stirred for 1 hour. The precipitate was collected by filtration, washed with water and dried to give the title compound (85.2 g) as a solid.
$^1$H-NMR (DMSO-$d_6$) δ: 3.21 (s, 6H); 5.35 (s, 1H); 5.64 (s, 2H); 6.40-6.52 (m, 2H); 7.18 (dd, 1H); 7.20 (s, 1H); 7.72 (s, 1H).

Intermediate 29G: 1-(2-Fluoro-4-nitro-phenyl)-4-(dimethoxymethyl)-1H-imidazol

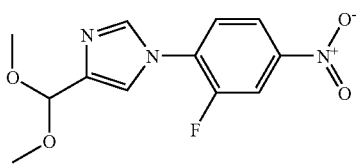

1-(2-Fluoro-4-nitrophenyl)-1H-imidazole-4-carboxaldehyde (Intermediate 30) (361.7 g, 1.538 mol) was suspended in dry methanol (1700 ml). Trimethyl orthoformate (340 g, 2 mol) and sodium hydrogen sulfate (8 g) were added and the mixture was heated to reflux for 3.5 hours. It was cooled to room temperature, a solution of sodium carbonate in water (10%, 200 ml) was added and it was stirred for 1 hour. It was diluted with water (4 L) and left for 2 hours. The precipitate was collected by filtration, washed with water and dried to give the title compound (402.4 g) as a solid.
$^1$H-NMR (DMSO-$d_6$) δ: 3.27 (s, 6H); 5.40 (s, 1H); 7.62 (s, 1H); 8.01 (dd, 1H); 8.18-8.23 (m, 2H); 8.42 (dd, 1H).

Intermediate 30: 1-(2-Fluoro-4-nitrophenyl)-1H-imidazole-4-carboxaldehyde

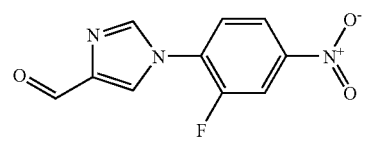

A mixture of 4(5)-H-imidazole-3-carboxaldehyde (153.8 g, 1.6 mol), 3,4-difluoronitrobenzene (267 g, 1.68 mol) and potassium carbonate (442 g, 3.2 mol) in dimethylsulfoxide (700 ml) was stirred under nitrogen at 90° C. for 8 hours. It was cooled to room temperature, diluted with ice water (4 L) and stirred for 30 minutes. The precipitate was collected by filtration, washed with water and dried to give the title compound (369.1 g) as a solid.
MS (ES+): 236.1 (MH$^+$) for $C_{10}H_6FN_3O_3$
$^1$H-NMR (DMSO-$d_6$) δ: 8.18 (m, 1H); 8.56 (m, 1H); 8.80 (m, 1H); 8.49 (m, 1H); 8.69 (m, 1H); 9.72 (s, 1H).

EXAMPLE 17

(5R)-3-[3-Fluoro-4-[(4-carboxaldehyde)-imidazol-1-yl]phenyl]-5-[(4-pentyl-1,2,3-triazol-1-yl)methyl] oxazolidin-2-one

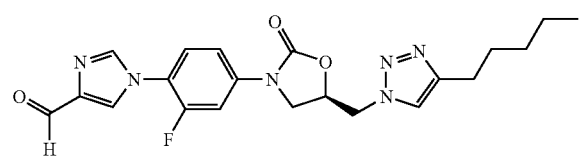

(5R)-3-[3-Fluoro-4-[(4-carboxaldehyde)-imidazol-1-yl] phenyl]-5-[azidomethyl]oxazolidin-2-one (Intermediate 29B) (0.507 g, 1.54 mmol) and 1-heptyne (0.82 ml, 6.1 mmol) were placed in a Radley's Carousel tube. Anhydrous 1,4-dioxane (5 ml) was added and the reaction mixture was heated to 110° C. under nitrogen for 20 hours. The solvent was removed under vacuum and the residue was purified by reverse phase HPLC to afford 10 mg of product.
MS (APCI): 427.2 (MH$^+$) for $C_{21}H_{23}FN_6O_3$
$^1$H-NMR (DMSO-$d_6$) δ: 0.86 (t, 3H); 1.28 (m, 4H); 1.56 (m, 2H); 2.61 (dd, 2H); 3.96 (dd, 1H); 4.31 (dd, 1H); 4.79 (d, 2H); 5.19 (m, 1H); 7.45 (dd, 1H); 7.73 (dd, 1H); 7.77 (dd, 1H); 7.91 (s, 1H); 8.26 (s, 1H); 8.46 (s, 1H); 9.85 (s, 1H).

EXAMPLE 18

(5R)-3-{3-Fluoro-4-[4-(hydroxymethyl)-1H-imidazol-1-yl]phenyl}-5-[(4-methyl-1,2,3-triazol-1-yl)methyl]oxazolidin-2-one

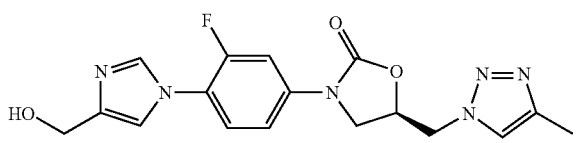

(5R)-3-{4-[4-(tert-Butyl(dimethyl)silyloxymethyl)-1H-imidazol-1-yl]-3-fluorophenyl}-5-[(4-methyl-1,2,3-triazol-1-yl)methyl]oxazolidin-2-one (Intermediate 31) (1.4 g, 2.88 mmol) was dissolved in tetrahydrofuran (15 ml), and tetrabutylammonium fluoride (3.2 ml, 1.0 M solution in THF) was added. The solution was stirred for 2 hours at room temperature and water (50 ml) was added. The precipitate was collected by filtration and purified by chromatography on silica gel with 3-6% methanol in dichloromethane to give the title compound (0.36 g).

MS (ESP): 373 (MH$^+$) for $C_{17}H_{17}FN_6O_3$ $^1$H-NMR (DMSO-d$_6$) δ: 2.25 (s, 3H); 3.95 (dd, 1H); 4.29 (dd, 1H); 4.43 (d, 2H); 4.79 (d, 2H); 5.00 (t, 1H); 5.16 (m, 1H); 7.37 (s, 1H); 7.43 (dd, 1H); 7.68 (m, 2H); 7.90 (s, 1H); 7.94 (d, 1H).

Intermediate 31: (5R)-3-[4-[4-(tert-Butyl(dimethyl)silyloxymethyl)-1H-imidazol-1-yl]-3-fluorophenyl]-5-[(4-methyl-1,2,3-triazol-1-yl)methyl]oxazolidin-2-one

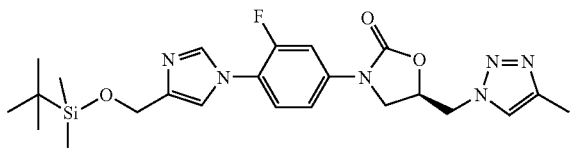

(5S)-3-{4-[4-(tert-Butyl(dimethyl)silyloxymethyl)-1H-imidazol-1-yl]-3-fluorophenyl}-5-(aminomethyl)oxazolidin-2-one (Intermediate 32) (1.78 g, 4.23 mmol) was reacted with diisopropylethylamine (2.9 ml, 17 mmol) and α,α-dichloroacetone tosylhydrazone (1.5 g, 5 mmol) as described for Example 3. Chromatography on silica gel with 1% methanol in dichloromethane gave the title product (1.41 g).

MS (ESP): 487 (MH$^+$) for $C_{23}H_{31}FN_6O_3Si$ $^1$H-NMR (DMSO-d$_6$) δ: 0.10 (s, 6H); 0.90 (s, 9H); 2.25 (s, 3H); 3.94 (dd, 1H); 4.29 (dd, 1H); 4.63 (s, 2H); 4.79 (d, 2H); 5.17 (m, 1H); 7.40 (s, 1H); 7.42 (dd, 1H); 7.67 (dd, 1H); 7.70 (dd, 1H); 7.90 (s, 1H); 7.96 (s, 1H).

Intermediate 32: (5S)-3-{4-[4-(tert-Butyl(dimethyl)silyloxymethyl)-1H-imidazol-1-yl]-3-fluorophenyl}-5-(aminomethyl)oxazolidin-2-one

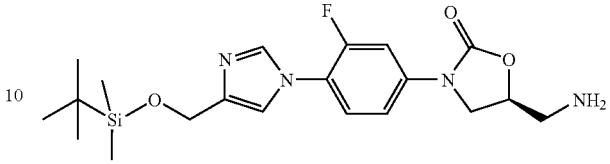

(5R)-3-{4-[4-(tert-Butyl(dimethyl)silyloxymethyl)-1H-imidazol-1-yl]-3-fluorophenyl}-5-(azidomethyl)oxazolidin-2-one (WO 9928317, WO 9910343, WO 9731917) (2.0 g, 4.17 mmol) was reacted as described for Intermediate 16 to give the title compound (1.8 g) as a solid, which was taken to the next step without further purification.

MS (ESP): 421 (MH$^+$) for $C_{20}H_{29}FN_4O_3Si$.

EXAMPLE 19

(5R)-3-[3-Fluoro-4-(4-methyl-1H-imidazol-1-yl)phenyl]-5-[(4-methyl-1,2,3-triazol-1-yl)methyl]oxazolidin-2-one

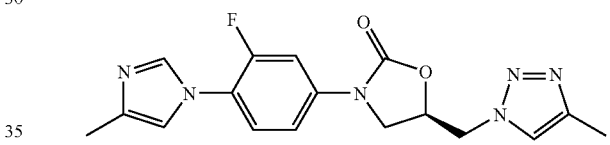

(5S)-3-[3-Fluoro-4-(4-methyl-1H-imidazol-1-yl)phenyl]-5-(aminomethyl)-oxazolidin-2-one (Intermediate 33) (0.67 g, 2.30 mmol) was reacted with diisopropylethylamine (1.61 ml, 2.77 mmol), and and α,α-dichloroacetone tosylhydrazone (0.75 g, 2.5 mmol) as described for Example 3. Chromatography on silica gel with 0-5% methanol in dichloromethane gave the title compound (0.24 g).

MS (ESP): 357.37 (MH$^+$) for $C_{17}H_{17}FN_6O_2$ $^1$H-NMR(DMSO-d$_6$) δ: 2.15 (s, 3H); 2.22 (s, 3H); 3.14 (dd, 1H); 4.26 (dd, 1H); 4.76 (d, 2H); 5.13 (m, 1H); 7.21 (s, 1H); 7.38 (dd, 1H); 7.61 (dd, 1H); 7.65 (dd, 1H); 7.85 (s, 1H); 7.86 (s, 1H).

Intermediate 33: (5S-3-[3-Fluoro-4-(4-methyl-1H-imidazol-1-yl)phenyl]-5-(aminomethyl)oxazolidin-2-one

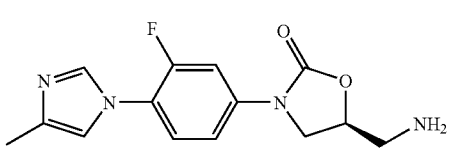

(5R)-3-[3-Fluoro-4-(4-methyl-1H-imidazol-1-yl)phenyl]-5-(azidomethyl)oxazolidin-2-one (Intermediate 34) (1.02 g, 3.21 mmol) was reacted with polystyrene-bound triphenylphosphine (8.5 g, 12.8 mmol) as described for the intermediate amine in Example 9 to give the crude title compound (0.67 g, 2.30 mmol). This product was carried on to the next reaction without further purification.

MS (APCI): 291.2 (MH$^+$) for $C_{14}H_{15}FN_4O_2$

Intermediate 34: (5R)-3-[3-Fluoro-4-(4-methyl-1H-imidazol-1-yl)phenyl]-5-(azidomethyl)oxazolidin-2-one

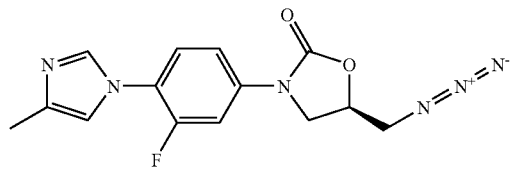

Sodium azide (0.596 g, 9.08 mmol) and 18-crown-6 (0.025 g, 0.095 mmol) were added to a solution of {(5R)-3-[3-fluoro-4-(4-methyl-1H-imidazol-1-yl)phenyl]-2-oxo-1,3-oxazolidin-5-yl}methyl methanesulfonate (WO 01/81350 A1) (3.161 g, 8.56 mmol) in DMF (8.5 ml). The reaction mixture was heated to 90° C. under an atmosphere of nitrogen for 19 hours. It was poured into a mixture of ethyl acetate and water and was extracted three times with ethyl acetate. The combined organic layers were washed with brine, dried over sodium sulfate, filtered and the solvent was removed under vacuum to afford the title compound (1.94 g) as a solid.

MS (ESP): 317.13 (MH$^+$) for $C_{14}H_{13}FN_6O_2$ $^1$H-NMR (DMSO-d$_6$) δ: 2.16 (s, 3H); 3.70 (dd, 1H); 3.78 (dd, 1H); 3.82 (dd, 1H); 4.18 (dd, 1H); 4.92 (m, 1H); 7.21 (s, 1H); 4.75 (dd, 1H); 7.62 (dd, 1H); 7.73 (dd, 1H); 7.85 (s, 1H).

EXAMPLE 20

(5R)-3-[3-Fluoro-4-(1H-imidazol-1-yl)phenyl]-5-[(4-methyl-1,2,3-triazol-1-yl)methyl]oxazolidin-2-one

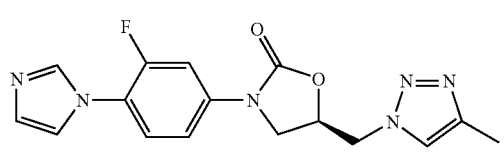

(5S)-5-(Aminomethyl)-3-[3-Fluoro-4-(1H-imidazol-1-yl) phenyl]oxazolidin-2-one (5.5 g, 19.9 mmol) [Tokuyama, Ryukou; Takahashi, Yoshiei; Tomita, Yayoi; Tsubouchi, Masatoshi; Iwasaki, Nobuhiko; Kado, Noriyuki; Okezaki, Eiichi; Nagata, Osamu, Chemical & Pharmaceutical Bulletin (2001), 49(4), 361-367] was reacted with triethylamine (11.1 ml, 79.6 mmol) and α,α-dichloroacetone tosylhydrazone (6.6 g, 22 mmol) as described for Example 3. Chromatography on silica gel with 0-5% methanol in dichloromethane gave the title compound (4.2 g).

MS (ESP): 343.38 (MH$^+$) for $C_{16}H_{15}FN_6O_2$ $^1$H-NMR(DMSO-d$_6$) δ: 2.22 (s, 3H); 3.92 (dd, 1H); 4.27 (dd, 1H); 4.76 (d, 2H); 5.14 (m, 1H); 7.11 (s, 1H); 7.41 (dd, 1H); 7.53 (d, 1H); 7.65 (dd, 1H); 7.67 (dd, 1H); 7.87 (s, 1H); 7.99 (s, 1H).

EXAMPLE 21

(5R)-3-[3-Fluoro-4-(4-carbonitrile-1H-pyrazol-1-yl) phenyl]-5-[(4-methyl-1,2,3-triazol-1-yl)methyl]oxazolidin-2-one

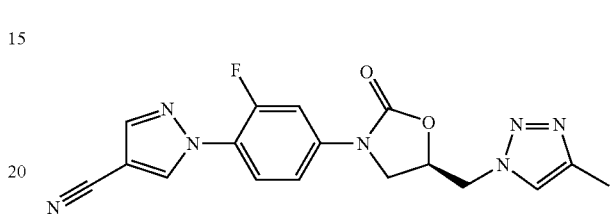

(5S)-3-[3-Fluoro-4-(4-carbonitrile-1H-pyrazol-1-yl)phenyl]-5-(aminomethyl)-oxazolidin-2-one (Intermediate 35) (0.45 g, 1.49 mmol) was reacted with diisopropylethylamine (1.04 ml, 5.96 mmol) and α,α-dichloroacetone tosylhydrazone (0.55 g, 1.87 mmol) as described for Example 3. Chromatography on silica gel with 1% to 3% methanol in dichloromethane gave the title product (0.45 g).

MS (ESP): 368 (MH$^+$) for $C_{17}H_{14}FN_7O_2$ $^1$H-NMR(DMSO-d$_6$) δ: 2.25 (s, 3H); 3.96 (dd, 1H); 4.30 (dd, 1H); 4.85 (d, 2H); 5.18 (m, 1H); 7.50 (dd, 1H); 7.74 (dd, 1H); 7.82 (dd, 1H); 7.90 (s, 1H); 8.41 (s, 1H); 9.07 (s, 1H).

Intermediate 35: (5S)-3-[3-Fluoro-4-(4-carbonitrile-1H-pyrazol-1-yl)phenyl]-5-(aminomethyl)-oxazolidin-2-one

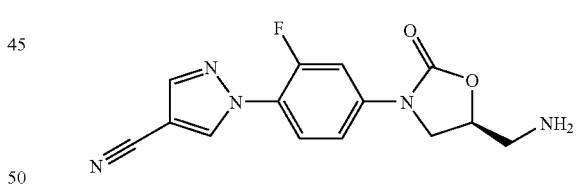

(5R)-3-[3-Fluoro-4-(4-carbonitrile-1H-pyrazol-1-yl)phenyl]-5-(azidomethyl)-oxazolidin-2-one (Intermediate 36) (0.88 g, 2.7 mmol) was hydrogenated as described for Intermediate 16. Chromatography on silica gel with 3-5% methanol in dichloromethane gave the title compound (0.46 g).

MS (ESP): 302 (MH$^+$) for $C_{14}H_{12}FN_5O_2$ $^1$H-NMR (DMSO-d$_6$) δ: 1.95 (brs, 1H); 2.86 (m, 2H); 3.94 (dd, 1H); 4.15 (dd, 1H); 4.65 (m, 1H); 7.56 (dd, 1H); 7.80 (m, 2H); 8.41 (s, 1H); 9.07 (s, 1H).

Intermediate 36: (5R)-3-[3-Fluoro-4-(4-carbonitrile-1H-pyrazol-1-yl)phenyl]-5-(azidomethyl)-oxazolidin-2-one

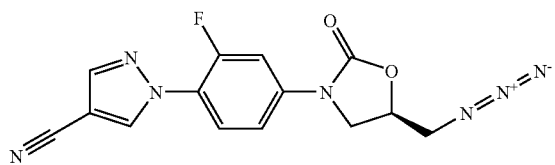

{(5R)-3-[3-Fluoro-4-(4-carbonitrile-1H-pyrazol-1-yl)phenyl]-5-[methylsulfonyloxymethyl]-oxazolidin 2-one (Intermediate 37) (1.1 g, 2.89 mmol) was dissolved in DMF (12 ml), sodium azide (0.38 g, 5.18 mmol) was added and it was stirred at 70° C. for 3 hours. It was partitioned between ethyl acetate and saturated aqueous sodium bicarbonate solution. The organic phase was washed with water followed by brine, dried over magnesium sulfate and concentrated under vacuum to give the title product (1 g).

MS (ESP): 328 (MH$^+$) for $C_{14}H_{10}FN_7O_2$ $^1$H-NMR (DMSO-d$_6$) δ: 3.92 (dd, 1H); 4.29 (dd, 1H); 4.54 (m, 2H); 5.08 (m, 1H); 7.56 (dd, 1H); 7.83 (m, 2H); 8.41 (s, 1H); 9.07 (s, 1H).

Intermediate 37: {(5R)-3-[3-Fluoro-4-(4-carbonitrile-1H-pyrazol-1-yl)phenyl]-5-[((methylsulfonyl)oxy)methyl]-1,3-oxazolidin 2-one

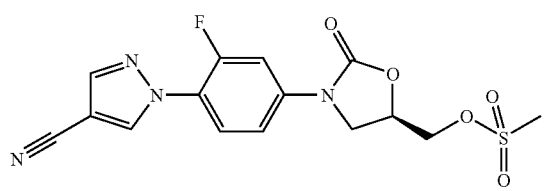

A slurry of (5R)-3-[3-Fluoro-4-(4-carbonitrile-1H-pyrazol-1-yl)phenyl]-5-(hydroxymethyl)-oxazolidin-2-one (Intermediate 38) (0.44 g, 1.45 mmol) in dichloromethane (7 ml) was cooled to 0° C. and triethylamine (0.27 ml, 1.95 mmol) was added, followed by methanesulfonyl chloride (0.21 g, 2.18 mmol). After 2 hours, the solution was poured into a saturated aqueous sodium bicarbonate solution and layers separated. It was extracted with dichloromethane, dried over magnesium sulfate and solvent removed under vacuum. Chromatography on silica gel with ethyl acetate gave the title product (0.40 g).

MS (APCI): 381 (MH$^+$) for $C_{15}H_{13}FN_4O_5S$ $^1$H-NMR (DMSO-d$_6$) δ: 3.28 (s, 3H); 3.92 (dd, 1H); 4.27 (dd, 1H); 4.54 (m, 2H); 5.08 (m, 1H); 7.56 (dd, 1H); 7.83 (m, 2H); 8.41 (s, 1H); 9.07 (s, 1H).

Intermediate 38: (5R)-3-[3-Fluoro-4-(4-carbonitrile-1H-pyrazol-1-yl)phenyl]-5-(hydroxymethyl)oxazolidin-2-one

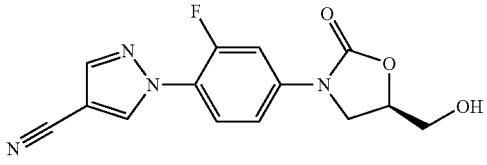

A solution of benzyl 3-fluoro-4-(4-cyano-1H-pyrazol-1-yl)phenylcarbamate (Intermediate 39) (0.71 g, 2.11 mmol) in tetrahydrofuran (10 ml) was cooled to −78° C. and n-butyllithium (1.37 ml, 1.6 M in hexane) was added drop wise under nitrogen. After stirring for 30 minutes, (R)-glycidylbutyrate (0.30 ml, 2.11 mmol, in 1 ml tetrahydrofurane) was added drop wise. The temperature was allowed to rise gradually to room temperature and the reaction was stirred overnight. It was quenched with aqueous ammonium chloride solution (4M), extracted with ethyl acetate and dried over magnesium sulfate. Chromatography on silica gel with hexanes/ethyl acetate (1:1 to pure ethylacetate) gave the title compound (0.45 g).

MS (ESP): 303 (MH$^+$) for $C_{14}H_{11}FN_4O_3$ $^1$H-NMR(DMSO-d$_6$) δ: 3.60 (m, 1H); 3.71 (m, 1H); 3.92 (m, 1H); 4.16 (dd, 1H); 4.78 (m, 1H); 5.27 (t, 1H); 7.56 (dd, 1H); 7.82 (m, 2H); 8.41 (s, 1H); 9.07 (s, 1H).

Intermediate 39: Benzyl 3-Fluoro-4-(4-cyano-1H-pyrazol-1-yl)phenylcarbamate

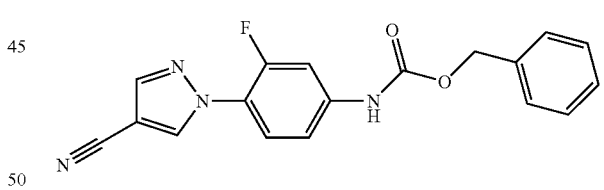

Thionyl chloride (0.23 ml) was added to a stirred solution of benzyl 4-[4-(aminocarbonyl)-1H-pyrazol-1-yl]-3-fluorophenylcarbamate (Intermediate 40) (0.76 g, 2.14 mmol) in DMF (20 ml) at 0° C. The resulting mixture was warmed to room temperature and stirred for 1 hour. It was quenched with aqueous saturated sodium bicarbonate solution, extracted with ethyl acetate, dried over sodium sulfate and solvent was removed under vacuum to give the title product (0.71 g).

MS (ESP): 337 (MH$^+$) for $C_{18}H_{13}FN_4O_2$ $^1$H-NMR (DMSO-d$_6$) δ: 5.21 (s, 2H); 7.43 (m, 6H); 7.71 (m, 2H); 8.40 (s, 1H); 9.23 (s, 1H); 10.32 (s, 1H).

Intermediate 40: Benzyl 4-[4-(aminocarbonyl)-1H-pyrazol-1-yl]-3-fluorophenylcarbamate

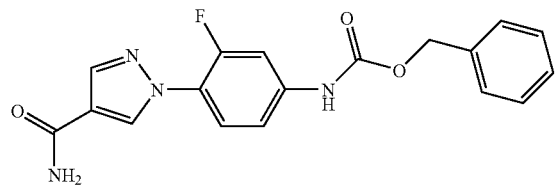

1-(4-{[Benzyloxycarbonyl]amino}-2-fluorophenyl)-1H-pyrazole-4-carboxylic acid (1.1 g, 3.1 mmol) (Intermediate 41) and benzotriazole-1-yl-oxy-trispyrrolidinophosphonium hexafluorophosphate (PyBob) (1.61 g, 3.1 mmol) were slurried in dichloromethane (25 ml), and triethylamine (0.43 ml, 3.1 mmol) was added. Excess ammonia solution in ethanol (2M) was added and the resulting mixture was stirred for 1 hour. The solvent removed under reduced pressure and the residue was taken up in water. It was basified by adding 1M sodium hydroxide solution, and then extracted with ethyl acetate, dried over magnesium sulfate and concentrated under vacuum. Chromatography on silica gel with 0-1% methanol in ethyl acetate gave the title compound (0.82 g).

MS (ESP): 355 (MH$^+$) for $C_{18}H_{15}FN_4O_3$ $^1$H-NMR (DMSO-d$_6$) δ: 5.21 (s, 2H); 7.19 (brs, 1H); 7.45 (m, 6H); 7.65 (d, 1H); 7.73 (m, 2H); 8.11 (s, 1H); 8.56 (s, 1H); 10.26 (s, 1H).

Intermediate 41: 1-(4-{[Benzyloxycarbonyl]amino}-2-fluorophenyl)-1H-pyrazole-4-carboxylic acid

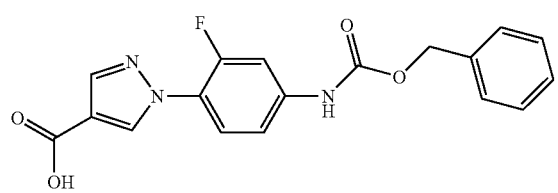

Ethyl 1-(4-{[benzyloxycarbonyl]amino}-2-fluorophenyl)-1H-pyrazole-4-carboxylate (*J. Med. Chem*, 2000, 43, 5, p 953) (1.33 g, 3.45 mmol) was taken up in ethanol/water (1/1, 80 ml), tetrahydrofuran (10 ml) was added, followed by aqueous sodium hydroxide solution (1M, 155 ml) and it was stirred at room temperature for 5 hours. The organic solvents were removed and the aqueous solution was acidified with 1M aqueous hydrochloric acid. The acidic solution was extracted with ethyl acetate, dried over magnesium sulfate and the solvent removed under reduced pressure to give the title product (1.1 g).

MS (ESP): 356 (MH$^+$) for $C_{18}H_{14}FN_3O_4$ $^1$H-NMR (DMSO-d$_6$) δ: 5.21 (s, 2H); 7.44 (m, 6H); 7.65 (d, 1H), 7.71 (dd, 1H); 8.10 (s, 1H); 8.59 (s, 1H); 10.28 (s, 1H); 12.65 (s, 1H).

EXAMPLE 22

(5R)-3-[3-Fluoro-4-(1-oxo-tetrahydro-2H-thiopyran-4-yl)phenyl]-5-[(4-methyl-1,2,3-triazol-1-yl)methyl]oxazolidin-2-one, E-Isomer

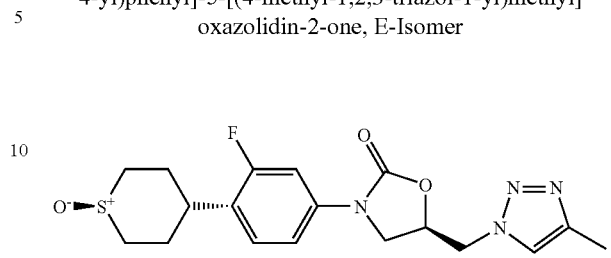

(5R)-3-[3-Fluoro-4-(1-oxo-tetrahydro-2H-thiopyran-4-yl)phenyl]-5-(azidomethyl)-oxazolidin-2-one, E-isomer (Intermediate 43) (1.00 g, 2.84 mmol) and 5,6,7,8-tetrachloro-2,9-dimethyl-1,4-dihydro-1,4-ethenonaphthalene (1.82 g, 5.67 mmol) was suspended in dry 1,4-dioxane (4 ml). The reaction mixture was heated in a sealed tube in a Smith microwave reactor (Personal Chemistry) at 180° C. for 30 minutes. The solvent was removed in vacuo. Chromatography on silica gel with 0-10% methanol in dichloromethane gave the title compound together with the corresponding 5-methyl triazole regioisomer. This mixture was purified by chromatography on Chirocel AD, eluting with 20% 2-propanol in hexanes to give 0.342 g (31%) of the title compound as a white solid.

MS (APCI): 393.14 (MH$^+$) for $C_{18}H_{21}FN_4O_3S$

NMR (DMSO-d$_6$) δ: 1.89 (q, 2H); 2.00 (d, 2H); 2.24 (s, 3H); 2.07 (t, 2H); 3.07 (t, 1H); 3.41 (m, 2H); 3.87 (dd, 1H); 4.22 (dd, 1H); 4.75 (d, 2H); 5.11 (m, 1H); 7.21 (dd, 1H); 7.36 (dd, 1H); 7.40 (dd, 1H); 7.88 (s, 1H).

EXAMPLE 23

(5R)-3-[3-Fluoro-4-(1-oxo-tetrahydro-2H-thiopyran-4-yl)phenyl]-5-[(4-methyl-1,2,3-triazol-1-yl)methyl]-1,3-oxazolidin-2-one, Z-Isomer

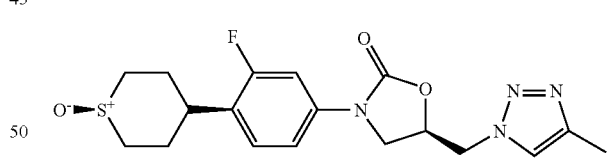

(5R)-3-[3-Fluoro-4-(1-oxotetrahydro-2H-thiopyran-4-yl)phenyl]-5-(azidomethyl)-oxazolidin-2-one, Z-isomer (Intermediate 42) (1.00 g, 2.84 mmol) and 5,6,7,8-tetrachloro-2,9-dimethyl-1,4-dihydro-1,4-ethenonaphthalene (1.82 g, 5.67 mmol) were reacted as described for Example 22 to give 0.370 g (33%) of the title compound as a white solid.

MS (APCI): 393.14 (MH$^+$) for $C_{18}H_{21}FN_4O_3S$

NMR (DMSO-d$_6$) δ: 1.69 (d, 2H); 2.24 (s, 3H); 2.36 (q, 2H); 2.84 (m, 2H); 2.97 (d, 2H); 3.07 (dd, 1H); 3.88 (dd, 1H); 4.24 (dd, 1H); 4.76 (d, 2H); 5.12 (m, 1H); 7.25 (dd, 1H); 7.39 (dd, 1H); 7.43 (dd, 1H); 7.89 (s, 1H).

Intermediate 42: (5R)-3-[3-Fluoro-4-(1-oxo-tetrahydro-2H-thiopyran-4-yl)phenyl]-5-(azidomethyl)oxazolidin-2-one, Z-Isomer

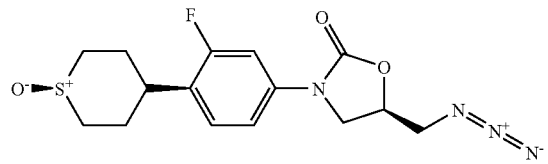

and

Intermediate 43: (5R)-3-[3-Fluoro-4-(1-oxo-tetrahydro-2H-thiopyran-4-yl)phenyl]-5-(azidomethyl)oxazolidin-2-one, E-Isomer

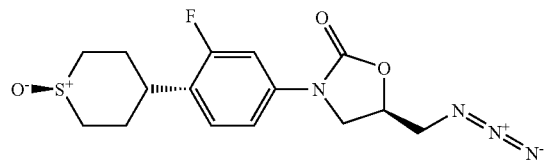

(5R)-3-(3-Fluoro-4-tetrahydro-2H-thiopyran-4-ylphenyl)-5-(hydroxymethyl)oxazolidin-2-one (WO 0281468 A1) (0.987 g, 3.0 mmol) was dissolved in dry dichloromethane (40 ml) and cooled to 0° C. Triethylamine (0.50 ml, 3.60 mmol) and methanesulphonyl chloride (0.26 ml 3.30 mmol) were added. The reaction mixture was stirred at 0° C. for 45 minutes then allowed to warm to room temperature. It was stirred at for a further 70 minutes then water (40 ml) was added. The dichloromethane layer was separated, dried over magnesium sulphate, filtered and concentrated in vacuo to yield a white solid. This intermediate mesylate was dissolved in anhydrous DMF (10 ml). Sodium azide (0.292 g, 4.50 mmol) was added and it was stirred at 85° C. for 60 minutes. It was cooled to room temperature and concentrated in vacuo. Water (100 ml) was added and the product extracted into ethyl acetate (200 ml). The ethyl acetate layer was separated, dried over magnesium sulphate, filtered, then concentrated in vacuo to yield a pale yellow oil of the intermediate azide. This oil was dissolved in a mixture of ethyl acetate (15 ml), methanol (20 ml) and water (20 ml) and cooled to 5° C. Sodium periodate (0.642 g, 3.00 mmol) was added and the reaction mixture left to stir at room temperature for 14 hours. It was filtered and organic solvents removed in vacuo. The resulting aqueous solution was extracted with ethyl acetate (80 ml), washed with sodium thiosulfate solution, dried over magnesium sulphate, filtered, then concentrated in vacuo to yield 0.983 mg (93%) of the title products as a mixture of the E- and Z-isomers. This mixture (11.4 g) was subjected to chromatography on Chirocel OD with 50% 2-propanol in hexanes. The first product which eluted was the Z-Isomer (6.212 g), the second one the E-Isomer (2.714 g).

MS (APCI): (Z-Isomer) 353.07 (MH$^+$) for $C_{15}H_{17}FN_4O_3S$

NMR (DMSO-d$_6$) (Z-Isomer) δ: 1.70 (d, 2H); 2.36 (q, 2H); 2.85 (m, 2H); 2.97 (d, 2H); 3.07 (t, 1H); 3.70 (dd, 1H); 3.80 (m, 2H); 4.16 (dd, 1H); 4.91 (m, 1H); 7.32 (dd, 1H); 7.40 (dd, 1H); 7.51 (dd, 1H).

MS (APCI): (E-Isomer) 353.07 (MH$^+$) for $C_{15}H_{17}FN_4O_3S$

NMR (DMSO-d$_6$) (E-Isomer) δ: 1.90 (q, 2H); 2.03 (d, 2H); 2.83 (dd, 2H); 3.08 (t, 1H); 3.39 (d, 2H); 3.71 (dd, 1H); 3.79 (m, 2H); 4.14 (dd, 1H); 4.92 (m, 1H); 7.29 (dd, 1H); 7.38 (dd, 1H); 7.49 (dd, 1H).

EXAMPLE 24

(5R)-3-[4-(Tetrahydro-2H-thiopyran-4-yl)-3,5-difluorophenyl]-5-[(4-methyl-1,2,3-triazol-1-yl)methyl]oxazolidin-2-one

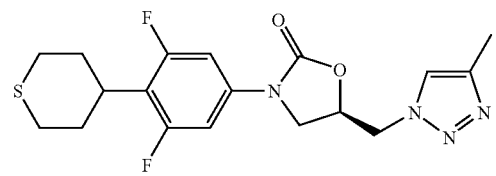

(5S)-5-(Aminomethyl)-3-[tetrahydro-2H-thiopyran-4-yl)-3,5-difluorophenyl]-oxazolidin-2-one (Intermediate 44) (1.98 g, 6 mmol) was reacted with diisopropylethyl amine (4.2 ml, 24 mmol) and α,α-dichloroacetone tosylhydrazone (2.1 g, 7.1 mmol) as described for Example 3. Chromatography on silica gel with 0-5% methanol in dichloromethane gave 2.13 g of the title compound.

MS(ESP): 395.2 (MH$^+$) $C_{18}H_{20}F_2N_4O_2S$ $^1$H-NMR(DMSO-d$_6$)δ: 7.88 (s, 1H); 7.25 (d, 2H); 5.14 (m, 1H); 4.75 (d, 2H); 4.21 (dd, 1H); 3.87 (dd, 1H); 2.98 (m, 1H); 2.81 (m, 2H); 2.67 (m, 2H); 2.24 (s, 3H); 2.0 (m, 4H).

Intermediate 44: (5S)-5-(Aminomethyl)-3-[tetrahydro-2H-thiopyran-4-yl)-3,5-difluorophenyl]oxazolidin-2-one

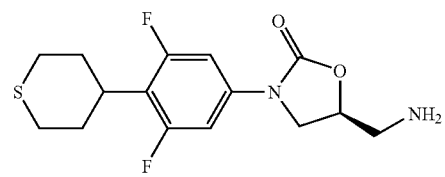

(5R)-3-[4-(Tetrahydro-2H-thiopyran-4-yl)-3,5-(difluorophenyl)-5-(azidomethyl)-oxazolidin-2-one (6.5 g, 18.3 mmol) and triphenyl phosphine (5.8 g, 22.0 mmol) were reacted as described for Intermediate 3. Chromatography on silica gel with 0-10% methanol in dichloromethane and trituration in hexanes gave the title compound (1.98 g) as a colourless solid.

MS(ESP): 329.37 (MH$^+$) for $C_{15}H_{18}F_2N_2O_2S$ $^1$H-NMR(DMSO-d$_6$) δ: 7.30 (d, 2H); 4.63 (m, 1H); 4.05 (dd, 1H); 3.86 (m, 1H); 2.98 (m, 1H); 2.81 (m, 4H); 2.67 (m, 2H); 2.00 (m, 4H); 1.59 (s, 2H).

Intermediate 45: (5R)-3-[4-(tetrahydro-2H-thiopyran-4-yl)-3,5-(difluorophenyl)-5-(azidomethyl)-oxazolidin-2-one

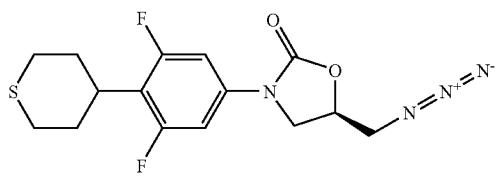

(5R)-3-[4-(Tetrahydro-2H-thiopyran-4-yl)-3,5-(difluorophenyl)-5-[(methanesulfonyl)methyl]oxazolidin-2-one (13 g, 30.4 mmol) was dissolved in DMF (150 ml), sodium azide (5.9 g, 91.2 mmol) was added and the mixture was heated to 80° C. for 3 hours. It was diluted with ethyl acetate and washed with water, brine and dried over sodium sulfate. Chromatography on silica gel with 0-5% methanol in dichloromethane gave the title compound as an oil (10.0 g).

$^1$H-NMR(DMSO-$d_6$) δ: 7.31 (d, 2H); 4.92 (m, 1H); 4.13 (dd, 1H); 3.79 (m, 2H); 3.70 (m, 1H); 2.98 (dd, 1H); 2.80 (m 2H); 2.67 (m, 2H); 2.04 (m, 4H).

Intermediate 46: (5R)-3-[4-(Tetrahydro-2H-thiopyran-4-yl)-3,5-(difluorophenyl)-5-[(methanesulfonyl)methyl]oxazolidin-2-one

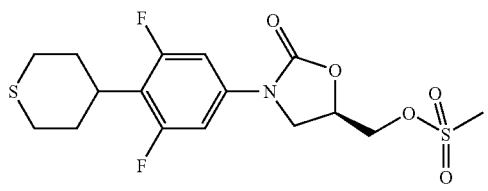

(5R)-3-[4-(Tetrahydro-2H-thiopyran-4-yl)-3,5-(difluorophenyl)-5-[(hydroxymethyl)methyl]oxazolidin-2-one (10 g, 30.4 mmol) was dissolved in dichloromethane (300 ml) and triethylamine (8.9 ml, 63.8 mmol) was added. It was cooled to 0° C. and methanesulfonyl chloride (2.9 ml, 36.4 mmol) was added drop wise. The reaction was stirred under nitrogen for 2 hours, and allowed to warm to room temperature. It was diluted with dichloromethane, washed with saturated aqueous sodium bicarbonate solution, brine, and dried over sodium sulfate to give the title compound (13 g) as a solid, which was used without further purification.

MS(ESP): 408.0 (MH$^+$) for $C_{16}H_{19}F_2NO_5S_2$ $^1$H-NMR(DMSO-$d_6$) δ: 7.31 (d, 2H); 5.03 (m, 1H); 4.49 (m, 2H); 4.18 (dd, 1H); 3.83 (m, 1H); 3.27 (s, 3H); 2.98 (m 1H); 2.78 (m, 2H); 2.66 (d, 2H); 2.05 (m, 4H).

Intermediate 47: (5R)-3-[4-(Tetrahydro-2H-thiopyran-4-yl)-3,5-(difluorophenyl)-5-[(hydroxymethyl)methyl]oxazolidin-2-one

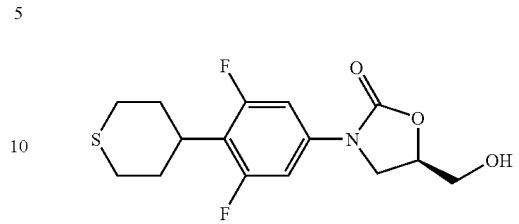

[3,5-(Difluoro-4-(tetrahydro-2H-thiopyran-4-yl)-phenyl] carbamic acid benzyl ester (Intermediate 47A) (281 g, 0.773 mol) was dissolved in THF (2800 ml). The solution was cooled to −78° C. and "BuLi (1.47 M, 526 ml) was added dropwise over 1 hour under nitrogen, keeping the temperature below −60° C. The dark red solution was left to stir for 10 minutes and a solution of glycidyl butyrate (109 ml) in THF (200 ml) was added drop wise over 40 minutes and the reaction left to warm to ambient temperature overnight. Methanol (480 ml) was added and the yellow precipitate stirred for 10 minutes. Saturated aqueous sodium hydrogen carbonate (1500 ml) was added, the organic layer was washed with saturated aqueous sodium chloride (1200 ml), dried (MgSO$_4$) and evaporated. The product was taken up in dichloromethane (2500 ml) evaporated to a low volume and isohexane was added (2000 ml). The product was filtered, washed with isohexane (500 ml) and dried in the vacuum oven overnight to provide the title compound as a cream solid (226 g).

$^1$H-NMR(DMSO-$d_6$) (300 MHz) δ: 1.9-2.1 (m, 4H); 2.6 (d, 2H); 2.7-2.85 (m, 2H); 2.9-3.05 (m, 1H); 3.5-3.6 (m, 1H); 3.6-3.7 (m, 1H); 3.8 (dd, 1H); 4.05 (t, 1H); 4.65-4.75 (m, 1H); 5.2 (t, 1H); 7.25 (d, 2H).

Intermediate 47A: [3,5-(Difluoro-4-(tetrahydro-2H-thiopyran-4-yl)-phenyl]carbamic acid benzyl ester

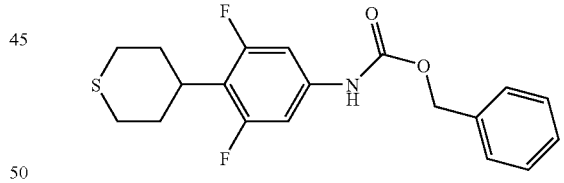

3,5-(Difluoro-4-(tetrahydro-2H-thiopyran-4-yl)-phenylamine (Intermediate 47B) (200 g, 0.872 mol) was dissolved in dichloromethane (3600 ml) and pyridine (120 ml). The solution was cooled to −20° C., a solution of benzyl chloroformate (149 ml) in dichloromethane (400 ml) was added drop wise over 1 hour and the reaction left stirring at room temperature overnight. The brown solution was washed with HCl (1M, 2250 ml), saturated aqueous sodium chloride (2250 ml) and dried (MgSO$_4$). The organic solution was evaporated to a low volume and isohexane was added (2000 ml) and the solid was filtered and dried in the vacuum oven overnight to provide the title compound as a yellow solid (281 g).

$^1$H-NMR(DMSO-$d_6$) (300 MHz) δ: 1.9-2.1 (m, 4H); 2.6 (d, 2H); 2.7-2.8 (m, 2H); 2.85-3.0 (m, 1H); 5.15 (s, 2H); 7.1 (d, 2H) 7.3-7.45 (m, 5H); 10.10 (s, 1H).

Intermediate 47B: 3,5-(Difluoro-4-(tetrahydro-2H-thiopyran-4-yl)-phenylamine

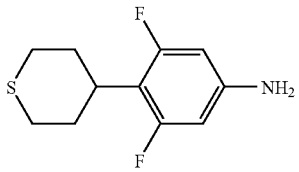

4-(4-Amino-2,6-difluorophenyl)tetrahydro-2H-thiopyran-4-ol (Intermediate 47C) (175 g, 0.713 mol) was dissolved in dichloromethane (880 ml). Triethylsilane (433 ml, 2.71 mol) was added, the reaction mixture cooled to 0° C. and TFA (960 ml) was added drop wise over 2 hours and it was left to stir at room temperature overnight. Water (6895 ml) was added and the biphasic solution stirred for 30 minutes. It was made basic with 880 ammonia (800 ml, pH>11). Diethyl ether (6000 ml) was added and the organic layer was washed with water (2400 ml), saturated aqueous sodium chloride (1200 ml), dried (MgSO$_4$) and evaporated. The product was diluted with isohexane (1000 ml) and the solid filtered and dried in the vacuum oven at 40° C. overnight to provide the title compound as a yellow solid (157 g).

$^1$H-NMR(CDCl$_3$) (300 MHz) δ: 1.9 (dd, 2H); 2.20 (m, 2H); 2.70 (d, 2H); 2.85 (m, 3H); 3.70 (brs, 2H); 6.10 (d, 2H).

Intermediate 47C: 4-(4-Amino-2,6-difluorophenyl)tetrahydro-2H-thiopyran-4-ol

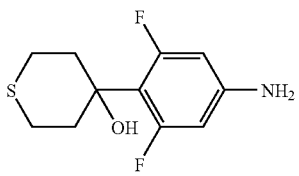

3,5-Difluoroaniline (250 g, 1.94 mol) was dissolved in THF (3800 ml) and cooled to −78° C. ″BuLi (1.59 M, 2560 ml) was added drop wise over 5 hours keeping the temperature below −70° C. and the resulting white slurry was stirred for 1 hour. Chlorotrimethylsilane (502 ml, 4.07 mol) in THF (2000 ml) was added drop wise over 2.5 hours keeping the temperature below −70° C. and the resulting yellow slurry was allowed to warm to room temperature overnight. The brown solution was recooled to −78° C., ″BuLi (1340 ml) was charged drop wise over 1.5 hours keeping the temperature below −70° C. and the reaction mixture was stirred for 5 hours. Tetrahydrothiopyran-4-one (241 g, 2.07 mol) in THF (1500 ml) was added drop wise over 2 hours keeping the temperature below −70° C. during the addition and then the reaction allowed to warm to room temperature overnight. The reaction was acidified to pH<1 using 5M HCl (approx 2000 ml) and it was extracted with diethyl ether (2500 ml). The organic layer was washed with 5M HCl (1000 ml) and the combined aqueous layers were basified using 880 ammonia to pH 11 (1500 ml), then extracted with diethyl ether (2500 ml×2), washed with saturated aqueous sodium chloride (1000 ml), dried over MgSO$_4$ and evaporated. The residue was taken up in dichloromethane (800 ml) evaporated to a low volume, isohexane (1000 ml) was added and it was cooled under ice. The yellow solid was filtered and dried in a vacuum oven at 40° C. overnight to provide 287 g of the title compound.

$^1$H-NMR(CDCl$_3$) (300 MHz) δ: 2.26 (d, 2H); 2.39 (t, 4H); 2.65 (t, 1H); 3.27 (t, 2H); 3.82 (br s, 2H); 6.17 (m, 2H).

EXAMPLE 25

(5R)-3-[4-(1,1-Dioxo-tetrahydro-2H-thiopyran-4-yl)-3,5-difluorophenyl]-5-[(4-methyl-1,2,3-triazol-1-yl)methyl]oxazolidin-2-one

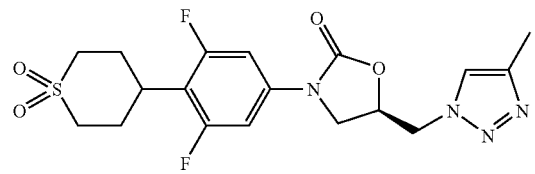

(5R)-3-[4-(Tetrahydro-2H-thiopyran-4-yl)-3,5-difluorophenyl]-5 [(4-methyl-1,2,3-triazol-1-yl)methyl]oxazolidin-2-one (Example 24) (0.5 g, 1.27 mmol) was oxidized with 3-chloro perbenzoic acid (0.94 g, 3.8 mmol) as described for Intermediate 2. Chromatography on silica gel with 0-10% methanol in dichloromethane gave the title compound as as colourless solid (0.54 g).

MS(ESP): 427.27 (MH$^+$) C$_{18}$H$_{20}$F$_2$N$_4$O$_4$S $^1$H-NMR(DMSO-d$_6$) δ: 7.88 (s, 1H); 7.28 (d, 2H); 5.14 (m, 1H); 4.76 (m, 2H); 4.22 (m, 1H); 3.88 (m, 1H); 3.37 (m, 4H); 3.10 (d, 2H); 2.43 (m, 2H); 2.24 (s, 2H); 2.03 (d, 2H).

EXAMPLE 26

(5R)-3-[3,5-Difluoro-4-(1-oxo-tetrahydro-2H-thiopyran-4-yl)phenyl]-5-[(4-methyl-1,2,3-triazol-1-yl)methyl]-oxazolidin-2-one, E-Isomer

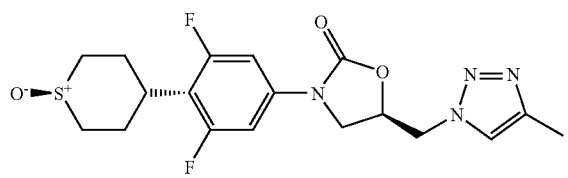

and

EXAMPLE 27

(5R)-3-[3,5-Difluoro-4-(1-oxo-tetrahydro-2H-thiopyran-4-yl)phenyl]-5-[(4-methyl-1,2,3-triazol-1-yl)methyl]oxazolidin-2-one, Z-Isomer

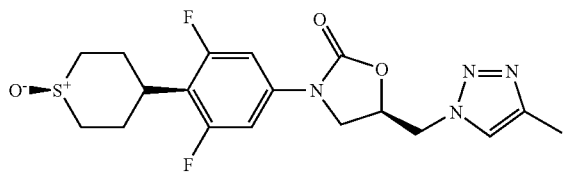

(5R)-3-[4-(Tetrahydro-2H-thiopyran-4-yl)-3,5-difluorophenyl]-5[(4-methyl-1,2,3-triazol-1-yl)methyl]oxazolidin-2-one (Example 24) (1.0 g, 2.5 mmol) was oxidized with sodium periodate (0.6 g, 2.8 mmol) as described for Intermediates 42 and 43. Reverse Phase chromatography with 10-25% acetonitrile in water containing 0.1% trifluoroacetic acid gave the Z-isomer as the first eluting product (105 mg), followed by elution of the E-isomer (60 mg) of the title compound.

MS(ESP) (for E- and Z-isomer): 411 (MH$^+$) $C_{18}H_{20}F_2N_4O_3S$ $^1$H-NMR(DMSO-d$_6$) (Z-isomer) δ: 7.87 (d, 1H); 7.25 (d, 2H); 5.14 (m, 1H); 4.75 (m, 2H); 4.21 (m, 1H); 3.87 (m, 1H); 3.35 (d, 1H); 3.20 (m, 1H); 2.85 (m, 5H); 2.24 (s, 3H); 2.05 (m, 1H); 1.65 (d, 1H).

(E-isomer) δ: 7.86 (s, 1H); 7.24 (d, 2H); 5.11 (m, 1H); 4.74 (m, 2H); 4.19 (m, 1H); 3.84 (m, 1H); 3.37 (m, 1H); 0.17 (m, 1H); 2.81 (m, 2H); 2.22 (s, 3H); 2.02 (m, 5H).

EXAMPLE 28

(5R)-3-[4-(1,1-Dioxo-3,6-dihydro-2H-thiopyran-4-yl)-3,5-difluorophenyl]-5-[(5-methyl-2H-tetrazol-2-yl)methyl]oxazolidin-2-one

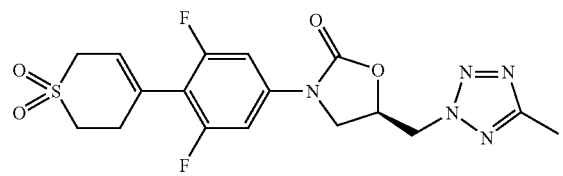

(5R)-3-[4-(1,1-Dioxo-3,6-dihydro-2H-thiopyran-4-yl)-3,5-difluorophenyl]-5-(hydroxymethyl)-oxazolidin-2-one (WO 01/81350 A1) (0.50 g, 1.39 mmol), triphenylphosphine (0.55 g, 2.1 mmol), and 5-methyl-1H-tetrazole (0.18 g, 2.14 mmol) were dissolved in dry tetrahydrofuran (5 ml), and cooled on an ice-water bath. Diisopropylazodicarboxylate (0.41 ml, 2.58 mmol) was added dropwise and the mixture was stirred at 0° C. for 4 hours. Methanol (3 ml) was added, followed by evaporation of the solvent under reduced pressure and purification by flash column chromatography on silica gel with 10% acetonitrile in dichloromethane. The material obtained after chromatography was precipitated from dichloromethane with diethyl ether to give the title compound (0.335 g).

MS (ESP): 851.02 (2 MH$^+$) for $C_{17}H_{17}F_2N_5O_4S$ $^1$H-NMR(CDCl$_3$) δ: 2.57 (s, 3H); 3.05 (m, 2H); 3.26 (dd, 2H); 3.85 (m, 2H); 4.01 (dd, 1H); 4.81 (dd, 1H); 4.91 (dd, 1H); 5.02 (dd, 1H); 5.21 (m, 1H); 5.78 (m, 1H); 7.17 (m, 2H).

EXAMPLE 29

(5R)-3-[4-(1,1-Dioxo-3,6-dihydro-2H-thiopyran-4-yl)-3,5-difluorophenyl]-5-[(5-Ethyl-2H-tetrazol-2-yl)methyl]oxazolidin-2-one

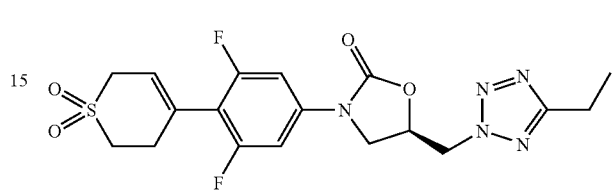

5-Ethyl-1H-tetrazole (0.164 g, 1.67 mmol), (5R)-3-[4-(1,1-dioxo-3,6-dihydro-2H-thiopyran-4-yl)-3,5-difluorophenyl]-5-(hydroxymethyl)oxazolidin-2-one (WO 01/81350 A1) (0.30 g, 0.84 mmol), and polystyrene-triphenylphosphine (1.73 mmol/g loading: Argonaut Technologies, Inc. Foster City, Calif. USA, 1.46 g, 2.53 mmol) were dissolved in dry dichloromethane (30 ml). Diisopropylazodicarboxylate (0.33 ml, 1.68 mmol) was added and the mixture was stirred at room temperature for 16 hours. The resin was filtered off and rinsed with dichloromethane. The filtrate was evaporated to dryness and purified by chromatography on silica gel with 10% acetonitrile in dichloromethane. The material obtained after chromatography was precipitated from dichloromethane with diethyl ether to yield the title compound as a white powder (0.26 g, 71%).

MS (ESP): 440.0 (MH$^+$) for $C_{18}H_{19}F_2N_5O_4S$ $^1$H-NMR(DMSO-d$_6$) δ: 1.11 (t, 3H); 2.82 (m, 4H); 3.37 (m, 2H); 3.92 (m, 3H); 4.29 (dd, 1H); 5.08 (dd, 1H); 5.15 (dd, 1H); 5.30 (m, 1H); 5.77 (m, 1H); 7.30 (d, 2H).

EXAMPLE 30

(5R)-3-[3-Fluoro-4-(4-carbonitrile-1H-pyrazol-1-yl)phenyl]-5-[(5-methyl-2H-tetrazol-2-yl)methyl]oxazolidin-2-one

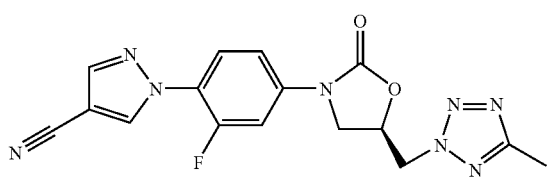

(5R)-3-[3-Fluoro-4-(4-carbonitrile-1H-pyrazol-1-yl)phenyl]-5-(hydroxymethyl)oxazolidin-2-one (Intermediate 38) (0.3 g, 0.99 mmol), 5-methy-1H-tetrazole (0.17 g, 2.08 mmol) and polystyrene-triphenylphosphine (1.73 mmol/g loading, 2.03 g) were reacted as described for Example 29. Chromatography on silica gel with hexanes/ethyl acetate (2:1 to pure ethyl acetate) gave the title compound (0.17 g).

MS (ESP): 369 (MH$^+$) for $C_{16}H_{13}FN_8O_2$ $^1$H-NMR(DMSO-d$_6$) δ: 2.46 (s, 3H); 3.99 (dd, 1H); 4.36 (dd, 1H); 5.10 (dd, 1H); 5.18 (dd, 1H); 5.31 (m, 1H); 7.49 (dd, 1H); 7.74 (dd, 1H); 7.83 (dd, 1H); 8.41 (s, 1H); 9.07 (s, 1H).

EXAMPLE 31

(5R)-3-[4-(1,1-Dioxo-3,6-dihydro-2H-thiopyran-4-yl)-3,5-difluorophenyl]-5-[(5-propyl-2H-tetrazol-2-yl)methyl]oxazolidin-2-one

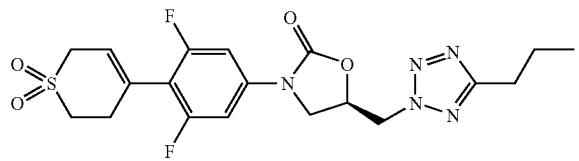

This compound was prepared from 5-propyl-1H-tetrazole (0.187 g, 1.67 mmol) and (5R)-3-[4-(1,1-dioxo-3,6-dihydro-2H-thiopyran-4-yl)-3,5-difluorophenyl]-5-(hydroxymethyl)oxazolidin-2-one (WO 01/81350 A1) (0.30 g, 0.84 mmol) as described for Example 29. The title compound was obtained as a colourless solid (0.25 g).

MS (ESP): 454.0 (MH$^+$) for $C_{19}H_{21}F_2N_5O_4S$ $^1$H-NMR(DMSO-$d_6$) δ: 0.86 (t, 3H); 1.64 (m, 2H); 2.78 (t, 2H); 2.85 (m, 2H); 3.37 (t, 2H); 3.92 (m, 3H); 4.29 (dd, 1H); 5.09 (dd, 1H); 5.15 (dd, 1H); 5.30 (m, 1H); 5.77 (m, 1H); 7.30 (d, 2H).

EXAMPLE 32

(5R)-3-[3-Fluoro-4-(4-methyl-1H-1,2,3-triazol-1-yl)phenyl]-5-[(5-methyl-2H-tetrazol-2-yl)methyl]oxazolidin-2-one

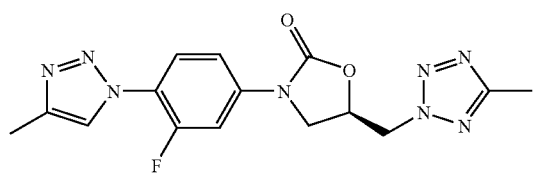

This compound was prepared from (5R)-3-[3-Fluoro-4-(4-methyl-1H-1,2,3-triazol-1-yl)phenyl]-5-(hydroxymethyl)oxazolidin-2-one (Intermediate 19) (1.054 g, 3.61 mmol) and 5-methyl-2H-tetrazole (0.608 g, 7.23 mmol), as described for Example 29. Chromatography on silica gel with 5% methanol in dichloromethane gave the crude product (0.72 g) which was purified further by trituration with dichloromethane and diethyl ether to afford the title product (0.571 g). The regioisomeric product (5R)-3-[3-fluoro-4-(4-methyl-1H-1,2,3-triazol-1-yl)phenyl]-5-[(5-methyl-1H-tetrazol-1-yl)methyl]-1,3-oxazolidin-2-one was also isolated (0.228 g).

MS (ESP): 359.31 (MH$^+$) for $C_{15}H_{15}FN_8O_2$ $^1$H-NMR (DMSO-$d_6$) δ: 2.36 (s, 3H); 2.47 (s, 3H); 4.00 (dd, 1H); 4.37 (dd, 1H); 5.11 (dd, 1H); 5.19 (dd, 1H); 5.31 (m, 1H); 7.50 (dd, 1H); 7.76 (dd, 1H); 7.85 (dd, 1H); 8.32 (s, 1H).

EXAMPLE 33

(5R)-3-[3-Fluoro-4-[4-(methylthio)-1H-1,2,3-triazol-1-yl]phenyl}-5-[(5-methyl-2H-tetrazol-2-yl)methyl]oxazolidin-2-one

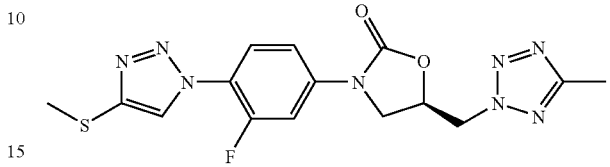

(5R)-3-{3-Fluoro-4-[4-(methylthio)-1H-1,2,3-triazol-1-yl]phenyl}-5-(hydroxymethyl)-oxazolidin-2-one (Intermediate 48) (1.10 g, 3.39 mmol), 5-methyl-2H-tetrazole (0.347 g, 4.09 mmol), polystyrene-triphenylphosphine (phosphine loading 1.51 mmol/g, 3.79 g, 5.72 mmol) and diisopropyl azodicarboxylate (0.856 g, 4.11 mmol) were reacted as described for Example 29 to afford the title product (0.632 g) after chromatography on silica gel with 5% methanol in dichloromethane. The regioisomeric product (5R)-3-{3-Fluoro-4-[4-(methylthio)-1H-1,2,3-triazol-1-yl]phenyl}-5-[(5-methyl-1H-tetrazol-1-yl)methyl]-1,3-oxazolidin-2-one was also isolated (0.369 g).

MS (APCI): 391.0 (MH$^+$) for $C_{15}H_{15}FN_8O_2S$ $^1$H-NMR (DMSO-$d_6$) δ: 2.47 (s, 3H); 2.56 (s, 3H); 4.00 (dd, 1H); 4.37 (t, 1H); 4.79 (m, 1H); 5.11 (dd, 1H); 5.19 (dd, 1H); 5.33 (m, 1H); 7.52 (dd, 1H); 7.78 (dd, 1H); 7.86 (t, 1H); 8.65 (d, 1H); 8.90 (s, 1H).

Intermediate 48: (5R)-3-[3-Fluoro-4-[4-(methylthio)-1H-1,2,3-triazol-1-yl]phenyl}-5-(hydroxymethyl)oxazolidin-2-one

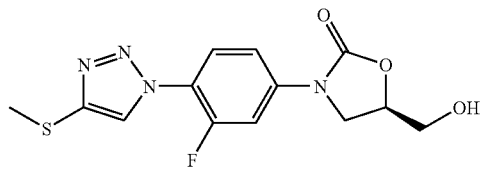

[3-Fluoro-4-[4-(methylthio)-1H-1,2,3-triazol-1-yl]phenyl]carbamic acid benzyl ester (Intermediate 49) (27.4 g, 76.5 mmol), LiHMDS (1M in THF, 91 ml) and R-(−)-glycidyl butyrate (11.5 g, 79.7 mmol) were reacted following the procedure for Intermediate 25 to give the crude title compound (19.4 g), which was used without further purification.

$^1$H-NMR (DMSO-$d_6$) δ: 2.53 (s, 3H); 3.50-3.78 (m, 2H); 3.91 (dd, 1H); 4.16 (dd, 1H); 4.72-4.83 (m, 1H); 5.26 (t, 1H); 7.58 (dd, 1H); 7.78-7.90 (m, 2H); 8.62 (d, 1H).

Intermediate 49: [3-Fluoro-4-[4-(methylthio)-1H-1,2,3-triazol-1-yl]phenyl]carbamic acid benzyl ester

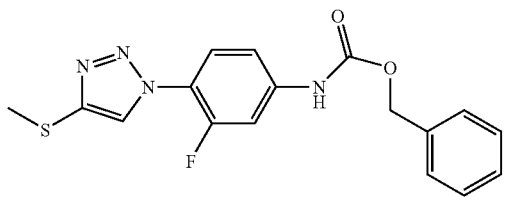

3-Fluoro-4-(3-(methylthio)-[1H-1,2,3]triazol-1-yl)-phenylamine (Intermediate 50) (4.65 g, 20 mmol) and benzyl chloroformate (4.25 g, 25 mmol) were reacted following the procedure for Intermediate 26. Chromatography on silica gel with 5% ethyl acetate in hexanes afforded the title compound (5.86 g) as a colourless solid.

$^1$H-NMR (CDCl$_3$) δ: 2.57 (s, 3H); 5.22 (s, 2H); 7.15 (m, 1H); 7.31-7.43 (m, 5H); 7.72 (dd, 1H); 7.80 (dd, 1H); 7.94 (d, 1H).

Intermediate 50: 3-Fluoro-4-(3-(methylthio)-1H-1,2,3]triazol-1-yl)-phenylamine

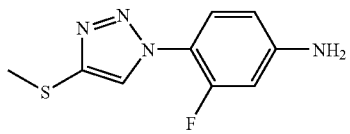

To 14.0 g (0.055 mol) of 1-(2-Fluoro-4-nitro-phenyl)-3-(methylthio)-1H-[1,2,3]triazole (Intermediate 51) was added concentrated HCl (260 ml), followed by addition of 62.1 g of SnCl$_2$.2H$_2$O (62.1 g, 0.275 mol). The mixture was heated to 90° C. for 1 hour with stirring. It was cooled to room temperature, neutralized with sodium hydrogencarbonate, extracted with ethyl acetate, dried over sodium sulfate, and solvent was removed under reduced pressure. Crystallization from ethyl acetate/hexanes gave the title compound (6.96 g) as a solid. The mother liquor was purified by chromatography on silica gel with 2040% ethyl acetate in hexanes, which provided further 4.65 g of product.

$^1$H-NMR (CDCl$_3$) δ: 2.57 (s, 3H); 3.69 (m); 6.40-6.60 (m, 2H); 7.57 (dd, 1H); 7.83 (d, 1H).

Intermediate 51: 1-(2-Fluoro-4-nitro-phenyl)-3-(methylthio)-1H-[1,2,3]triazole

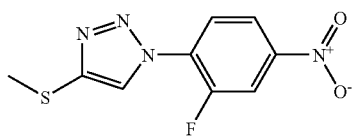

4-Methylthio-1,2,3-triazole (1.15 g, 10 mmol) and 3,4-difluoro-1-nitrobenzene (1.59 g, 10 mmol) were reacted as described for Intermediate 27, at 60° C. for 18 hours. Chromatography on silica gel with 3-5% ethyl acetate in hexane afforded the title compound (1.28 g), together with the corresponding 2H-[1,2,3]triazole (0.66 g). The structures were confirmed by x-ray analysis.

$^1$H-NMR (CDCl$_3$) δ: 2.65 (s, 3H); 7.78 (s, 1H); 8.14-8.21 (m, 3H).

EXAMPLE 34

(5R)-3-[4-(Tetrahydro-2H-thiopyran-4-yl)-3,5-difluorophenyl]-5-[(5-methyl-2H-tetrazol-2-yl)methyl]oxazolidin-2-one

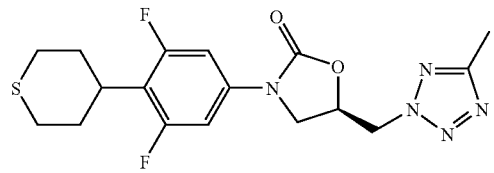

(5R)-3-[4-(Tetrahydro-2H-thiopyran-4-yl)-3,5-difluorophenyl]-5-[(hydroxymethyl)methyl]oxazolidin-2-one (Intermediate 47) (0.66 g, 2 mmol), triphenylphosphine (0.786 g, 3 mmol), 5-methyl tetrazole (0.303 g, 3.6 mmol) and diisopropylazodicarboxylate (0.59 ml, 3 mmol) were reacted as described for Example 28. Chromatography on silica gel with 0.2-0.5% methanol in dichloromethane followed by 40% ethyl acetate in hexanes gave the title product (0.412 g).

MS(ESP): 396.20 (MH$^+$) for C$_{17}$H$_{19}$F$_2$N$_5$O$_2$S $^1$H-NMR (DMSO-d$_6$) δ: 7.24 (d, 2H); 5.27 (m, 1H); 5.13 (m, 1H); 5.07 (m, 1H); 4.26 (m, 1H); 3.90 (m, 1H); 2.98 (dd, 1H); 2.80 (dd, 2H); 2.67 (m, 2H); 2.45 (s, 3H); 2.0 (m, 4H).

EXAMPLE 35

(5R)-3-[4-(1,1-dioxo-tetrahydro-2H-thiopyran-4-yl)-3,5-difluorophenyl]-5-[(5-methyl-2H-tetrazol-2-yl)methyl]oxazolidin-2-one

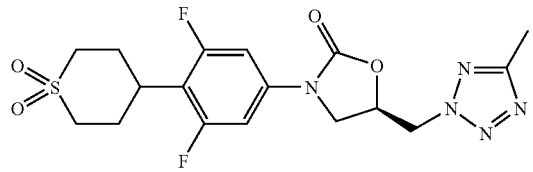

(5R)-3-[4-(Tetrahydro-2H-thiopyran-4-yl)-3,5-difluorophenyl]-5-[(5-methyl-2H-tetrazol-2-yl)methyl]oxazolidin-2-one (Example 34) (0.5 g, 1.26 mmol) and 3-chloro perbenzoic acid (0.98 g, 3.8 mmol) were reacted as described for Intermediate 2. Chromatography on silica gel with 1% methanol in dichloromethane gave the title compound (0.405 g).

MS(ESP): 428.0 (MH$^+$) for C$_{17}$H$_{19}$F$_2$N$_5$O$_4$S $^1$H-NMR(DMSO-d$_6$) δ: 7.27 (d, 2H); 5.28 (m, 1H); 5.14 (m, 1H); 5.07 (m, 1H); 4.27 (dd, 1H); 3.91 (m, 1H); 3.36 (m, 3H); 3.10 (d, 2H); 2.45 (s, 3H); 2.43 (m, 2H); 2.03 (d, 2H).

EXAMPLE 36

(5R)-3-[4-(1-Oxo-tetrahydro-2H-thiopyran-4-yl)-3,5-difluorophenyl]-5-[(5-methyl-2H-tetrazol-2-yl)methyl]oxazolidin-2-one, Z isomer

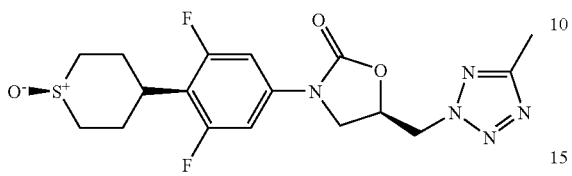

(5R)-3-[4-(Tetrahydro-2H-thiopyran-4-yl)-3,5-difluorophenyl]-5-[(5-methyl-2H-tetrazol-2-yl)methyl]oxazolidin-2-one (Example 34) (0.53 g, 1.34 mmol) was oxidized with sodium periodate (0.314 g, 1.47 mmol) as described for Intermediates 42 and 43. Chromatography on silica gel with 0-5% methanol in dichloromethane gave a mixture together with the corresponding E-isomer, which was separated on a Chiracel OD chiral chromatography column using hexanes/isopropanol (1:1) as eluant to give the title compound (50 mg) as a colourless solid.

MS(ESP): 412.02 (MH$^+$) for $C_{17}H_{19}F_2N_5O_3S$ $^1$H-NMR(DMSO-d$_6$) δ: 7.25 (d, 2H); 5.26 (m, 1H); 5.11 (m, 3H); 4.25 (dd, 1H); 3.88 (m, 1H); 3.18 (m, 1H); 2.95 (m, 2H); 2.85 (m, 1H); 2.68 (m, 2H); 2.44 (s, 3H); 1.62 (d, 2H).

EXAMPLE 37

(5R)-3-[3-Fluoro-4-(4-methyl-1H-imidazol-1-yl)phenyl]-5-[(5-methyl-2H-tetrazol-2-yl)methyl]oxazolidin-2-one

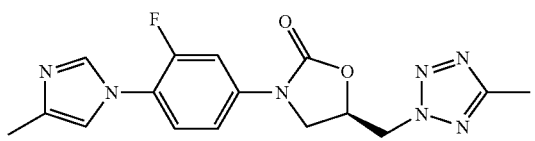

A solution of 5-methyltetrazole (0.18 g, 2.18 mmol) in anhydrous N,N-dimethylformamide (10 ml) was cooled to 0° C., sodium hydride (0.088 g, 2.18 mmol) was added and it was stirred for 25 minutes. {(5R)-3-[3-fluoro-4-(4-methyl-1H-imidazol-1-yl)phenyl]-2-oxo-1,3-oxazolidin-5-yl}methyl methanesulfonate (WO 01/81350 A1) (0.70 g, 1.90 mmol) was added and the reaction was stirred overnight, allowing the temperature to reach room temperature slowly. The reaction was diluted with ethyl acetate (150 ml), washed with a saturated aqueous solution of sodium hydrogen carbonate (50 ml), then with brine (50 ml), and dried over anhydrous magnesium sulfate. Ethyl acetate was removed in vacuo, and the crude product was chromatographed on silica gel column with 0-4% methanol in dichloromethane to give the title compound (0.205 g) as a colourless solid.

MS (ESP): 358.32 (MH$^+$) for $C_{16}H_{16}FN_7O_2$ $^1$H-NMR(DMSO-d$_6$) δ: 2.15 (s, 3H); 2.43 (s, 3H); 3.94 (dd, 1H); 4.31 (dd, 1H); 5.10 (m, 2H); 5.27 (m, 1H); 7.22 (s, 1H); 7.37 (dd, 1H); 7.61 (dd, 1H); 7.65 (dd, 1H); 7.86 (s, 1H).

EXAMPLE 38

(5R)-3-[3,5-Difluoro-4-(1-glycoloyl-1,2,3,6-tetrahydropyridin-4-yl)phenyl]-5-[(4-methyl-1,2,3-triazol-1-yl)methyl]oxazolidin-2-one

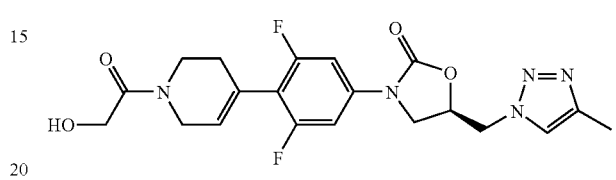

(5R)-3-[4-(1-Acetoxyacetyl-1,2,3,6-tetrahydropyridin-4-yl)-3,5-difluorophenyl]-5-[(4-methyl-1,2,3-triazol-1-yl)methyl]oxazolidin-2-one (Intermediate 52) (1.00 g, 2.10 mmol) was suspended in anhydrous methanol (20 ml). A solution of ammonia in methanol (2 M, 10 ml) was added and the mixture was heated at 65° C. After 5 minutes heating was removed and the reaction was stirred at room temperature for 4 hours. The product was collected by filtration, washed with methanol followed by diethyl ether, and dried under vacuum to give the title compound (750 mg) as a colourless solid.

MS (ESP): 434 (MH$^+$) for $C_{20}H_{21}F_2N_5O_4$ $^1$H-NMR(500 MHz, DMSO-d$_6$) δ: 2.24 (s, 3H); 2.33 (brs, 1H); 2.40 (s, 1H); 3.55 (dd, 1H); 3.70 (dd, 1H); 3.89 (dd, 1H); 4.08 (br s, 1H); 4.13-4.14 (m, 2H); 4.18 (d, 1H); 4.24 (dd, 1H); 4.64 (m, 1H); 4.76 (d, 2H); 5.15 (m, 1H); 5.89 (m, 1H); 7.31 (d, 2H); 7.89 (s, 1H).

Intermediate 52: (5R)-3-[4-(1-Acetoxyacetyl-1,2,3,6-tetrahydropyridin-4-yl)-3,5-difluorophenyl]-5-[(4-methyl-1,2,3-triazol-1-yl)methyl]oxazolidin-2-one

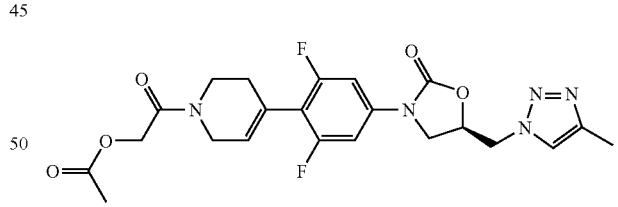

(5R)-3-[3,5-difluoro-4-(1,2,3,6-tetrahydropyridin-4-yl)phenyl]-5-[(4-methyl-1,2,3-triazol-1-yl)methyl]oxazolidin-2-one hydrochloride (Intermediate 53) (1.54 g, 3.74 mmol) was suspended in dichloromethane (10 ml). Pyridine (20 ml) was added and the mixture was cooled to 0° C. Acetoxyacetyl chloride (0.80 ml, 7.48 mmol) was added and the reaction mixture was stirred at room temperature. After 16 hours, additional acetoxyacetyl chloride (0.80 ml, 7.48 mmol) was added. After stirring for 3 days, the mixture was poured into dichloromethane, the organic phase was washed with water, dried over magnesium sulfate and concentrated under vacuum. Chromatography on silica gel with ethyl acetate gave 1.09 g of the title product.

MS (ESP): 476 (MH$^+$) for $C_{22}H_{23}F_2N_5O_5$ $^1$H-NMR(500 MHz, DMSO-d$_6$) δ: 2.11 (s, 3H); 2.24 (s, 3H); 2.33 (brs, 1H); 2.43 (brs, 1H); 3.58 (dd, 1H); 3.66 (dd, 1H); 3.89 (dd, 1H); 4.09 (s, 1H); 4.13 (s, 1H); 4.24 (dd, 1H); 4.77 (d, 2H); 4.84 (s, 1H); 4.88 (s, 1H); 5.14 (m, 1H); 5.89 (m, 1H); 7.31 (d, 2H); 7.89 (s, 1H).

Intermediate 53: (5R)-3-[3,5-Difluoro-4-(1,2,3,6-tetrahydropyridin-4-yl)phenyl]-5-[(4-methyl-1,2,3-triazol-1-yl)methyl]oxazolidin-2-one

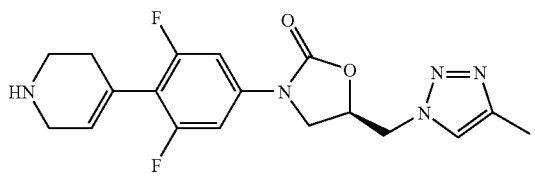

(5R)-3-[4-(1-Benzyl-1,2,3,6-tetrahydropyridin-4-yl)-3,5-difluorophenyl]-5-[(4-methyl-1,2,3-triazol-1-yl)methyl]oxazolidin-2-one (Example 39) (1.74 g, 3.74 mmol) was dissolved in dichloromethane (20 ml) and cooled to 0° C. Diisopropylethylamine (0.13 ml, 0.75 mmol) was added, followed by addition of 1-chloroethylchloroformate (0.48 ml, 4.48 mmol). It was stirred for 30 minutes, then allowed to warm to room temperature. After 16 hours, the reaction mixture was concentrated under vacuum. The intermediate chloroethylcarbamate was dissolved in methanol (20 ml) and heated to reflux. After 30 min, the reaction mixture was cooled to room temperature and concentrated under vacuum to give the title compound as the hydrochloride salt (1.5 g), which was used without further purification.

MS (ESP): 376 (MH$^+$) for $C_{18}H_{19}F_2N_5O_2$

EXAMPLE 39

(5R)-3-[4-(1-Benzyl-1,2,3,6-tetrahydropyridin-4-yl)-3,5-difluorophenyl]-5-[(4-methyl-1,2,3-triazol-1-yl)methyl]oxazolidin-2-one

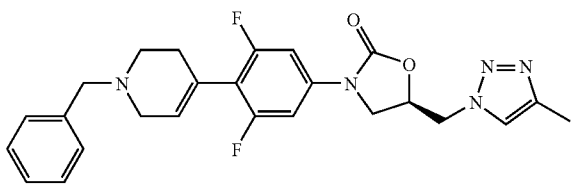

(5S)-5-(Aminomethyl)-3-[4-(1-benzyl-1,2,3,6-tetrahydropyridin-4-yl)-3,5-diflurophenyl]-1,3-oxazolidin-2-one (Intermediate 54) (3.20 g, 8.01 mmol) was reacted with diisopropylethylamine (5.60 ml, 32.04 mmol) and 1,1-dichloroacetone toluenesulfonylhydrazone (2.8 g, 9.6 mmol) as described for Example 3. Chromatography on silica gel with ethyl acetate gave 1.74 g of the title product.

$^1$H-NMR(500 MHz, DMSO-d$_6$) δ: 2.24 (s, 3H); 2.33 (brs, 2H); 2.64 (dd, 2H); 3.05-3.10 (m, 2H); 3.61 (s, 2H); 3.88 (dd, 1H); 4.23 (dd, 1H); 4.76 (2H); 5.14 (m, 1H); 5.81 (brs, 1H); 7.27-7.36 (m, 7H); 7.88 (s, 1H).

Intermediate 54: (5S)-5-(Aminomethyl)-3-[4-(1-benzyl-1,2,3,6-tetrahydropyridin-4-yl)-3,5-difluorophenyl]oxazolidin-2-one

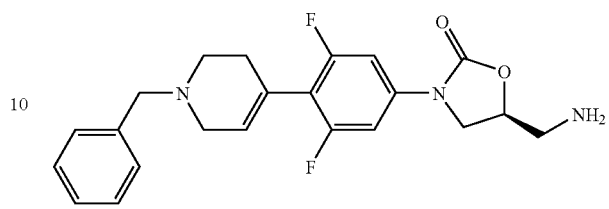

(5R)-5-(Azidomethyl)-3-[4-(1-benzyl-1,2,3,6-tetrahydropyridin-4-yl)-3,5-difluorophenyl]-1,3-oxazolidin-2-one (WO 0181350) (10.60 g, 24.97 mmol) was dissolved in acetonitrile (250 ml) and water (25 ml). Triphenylphosphine (7.86 g, 29.96 mmol) was added and the suspension was stirred at room temperature for approximately 16 h. The reaction mixture was concentrated under vacuum. The crude material was purified by chromatography on silica gel using 2.5-5% methanol in dichloromethane to give 7.03 g of the title product.

MS (ESP): 400 (MH$^+$) for $C_{22}H_{23}F_2N_3O_2$ $^1$H-NMR(500 MHz, DMSO-d$_6$) δ: 1.84 (s, 2H); 1.93 (s, 2H); 2.33 (brs, 2H); 2.63 (dd, 2H); 3.04-3.07 (m, 2H); 3.36 (brs, 1H); 3.47 (brs, 1H); 3.84 (dd, 1H); 4.16 (dd, 1H); 4.95 (m, 1H); 5.80 (m, 1H); 7.27-7.36 (m, 7H).

EXAMPLE 40

(5R)-3-(4-{1-[(2S)-2,3-Dihydroxypropanoyl]-1,2,3,6-tetrahydropyridin-4-yl}-3,5-difluorophenyl)-5-[(4-methyl-1,2,3-triazol-1-yl)methyl]oxazolidin-2-one

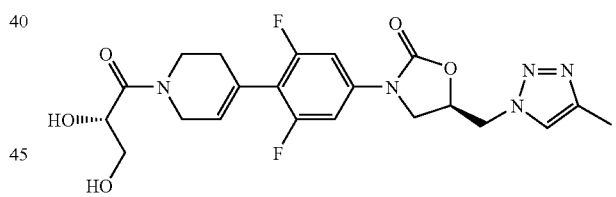

(5R)-3-[4-(1-{[(4S)-2,2-Dimethyl-1,3-dioxolan-4-yl]carbonyl}-1,2,3,6-tetrahydropyridin-4-yl)-3,5-difluorophenyl]-5-[(4-methyl-1,2,3-triazol-1-yl)methyl]oxazolidin-2-one (Intermediate 55) (542 mg, 1.08 mmol) was dissolved in tetrahydrofuran (20 ml). A solution of hydrochloric acid (1N, 10 ml) was added and the reaction mixture was stirred at room temperature. After 64 hours, the solution was poured into ethyl acetate the aqueous was extracted with ethyl acetate. The aqueous was basified with a solution of 10% aqueous sodium acetate and re-extracted with ethyl acetate. The combined organics were dried over magnesium sulfate and concentrated under vacuum. Chromatography on silica gel with 10% methanol in ethyl acetate gave 254 mg of the title product.

MS (ESP): 464 (MH$^+$) for $C_{21}H_{23}F_2N_5O_5$ $^1$H-NMR (500 MHz, DMSO-d$_6$) δ: 2.24 (s, 3H); 2.32-2.41 (m, 2H); 3.50 (m, 1H); 3.57 (m, 1H); 3.70-3.87 (m, 2H); 3.89 (dd, 1H); 4.12-4.40 (m, 4H); 4.73-4.77 (m, 3H); 5.04 (m, 1H); 5.15 (m, 1H); 5.90 (m, 1H); 7.30 (d, 2H); 7.89 (s, 1H).

Intermediate 55: (5R)-3-[4-(1-{[(4S)-2,2-Dimethyl-1,3-dioxolan-4-yl]carbonyl}-1,2,3,6-tetrahydropyridin-4-yl)-3,5-difluorophenyl]-5-[(4-methyl-1,2,3-triazol-1-yl)methyl]oxazolidin-2-one

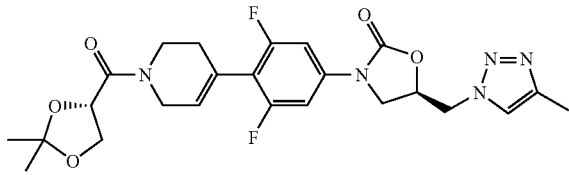

(5R)-3-[3,5-Difluoro-4-(1,2,3,6-tetrahydropyridin-4-yl)phenyl]-5-[(4-methyl-1,2,3-triazol-1-yl)methyl]oxazolidin-2-one hydrochloride (Intermediate 53) (1.13 g, 2.75 mmol) was suspended in dichloromethane (20 ml). Pyridine (2.22 ml, 27.50 mmol) was added and the solution was cooled to 0° C. A solution of (4S)-2,2-dimethyl-1,3-dioxolane-4-carbonyl chloride (WO 01/81350, 0.89 g, 5.43 mmol) in dichloromethane (10 ml) was added. After 2 hours, the solution was poured into water, the organic phase was washed with brine, dried over magnesium sulfate and concentrated under vacuum. Chromatography on silica gel with ethyl acetate gave 542 mg of the title product.

MS (ESP): 504 (MH$^+$) for $C_{24}H_{27}F_2N_5O_5$ $^1$H-NMR(500 MHz, DMSO-d$_6$) δ: 1.33 (s, 3H); 1.36 (s, 3H); 2.24 (s, 3H); 2.30-2.48 (m, 2H); 3.70 (m, 1H); 3.78 (m, 1H); 3.89 (dd, 1H); 4.09-4.26 (m, 5H); 4.76 (d, 2H); 4.92 (m, 1H); 5.14 (m, 1H); 5.92 (m, 1H); 7.31 (d, 2H); 7.89 (s, 1H).

EXAMPLE 41

(5R)-3-[3-Fluoro-4-(1-glycoloyl-1,2,3,6-tetrahydropyridin-4-yl)phenyl]-5-[(4-methyl-1,2,3-triazol-1-yl)methyl]oxazolidin-2-one

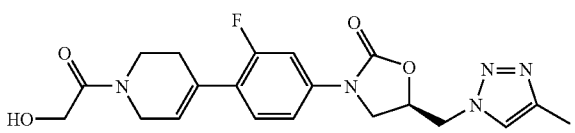

(5R)-3-[4-(1-Acetoxyacetyl-1,2,3,6-tetrahydropyridin-4-yl)-3-fluorophenyl]-5-[(4-methyl-1,2,3-triazol-1-yl)methyl]oxazolidin-2-one (Example 42) (1.06 g, 2.32 mmol) was suspended in anhydrous methanol (23 ml). A solution of ammonia in methanol (2 M, 15 ml) was added and the mixture was heated at 65° C. for 5 minutes and then left at room temperature for 7 hours. The product was collected by filtration, washed with methanol followed by diethyl ether, and dried under vacuum to give 618 mg of the title compound.

MS (ESP): 416 (MH$^+$) for $C_{20}H_{22}FN_5O_4$ $^1$H-NMR(DMSO-d$_6$) δ: 2.24 (s, 3H); 2.44-2.51 (m, 2H); 3.55 (m, 1H); 3.70 (m, 1H); 3.90 (dd, 1H); 4.07-4.19 (m, 4H); 4.25 (dd, 1H); 4.62 (m, 1H); 4.77 (d, 2H); 5.13 (m, 1H); 6.03 (m, 1H); 7.27-7.46 (m, 3H); 7.89 (s, 1H).

EXAMPLE 42

(5R)-3-[4-(1-Acetoxyacetyl-1,2,3,6-tetrahydropyridin-4-yl)-3-fluorophenyl-]5-[(4-methyl-1,2,3-triazol-1-yl)methyl]oxazolidin-2-one

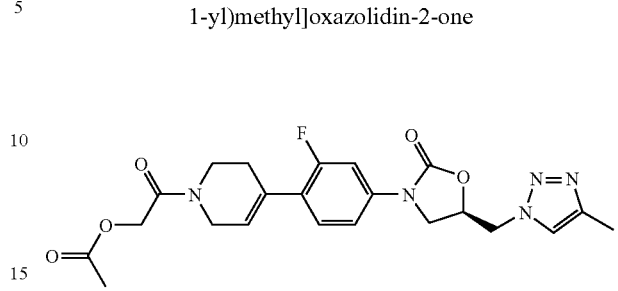

(5R)-3-[3-Fluoro-4-(1,2,3,6-tetrahydropyridin-4-yl)phenyl]-5-[(4-methyl-1,2,3-triazol-1-yl)methyl]oxazolidin-2-one (Intermediate 56) (2.49 g, 6.32 mmol) was suspended in dichloromethane (50 ml) and cooled to 0° C. Pyridine (5.10 ml, 63.22 mmol) was added followed by acetoxyacetyl chloride (1.40 ml, 12.64 mmol) and the mixture was allowed to warm to room temperature. After 16 hours water was added, the organic phase was extracted with dichloromethane, washed with brine, dried over magnesium sulfate and concentrated under vacuum. Chromatography on silica gel with ethyl acetate gave 1.33 g of the title product.

MS (APCI): 458 (MH$^+$) for $C_{22}H_{24}FN_5O_2$ $^1$H-NMR(500 MHz, DMSO-d$_6$) δ: 2.11 (s, 3H); 2.24 (s, 3H); 2.44 (m, 1H); 2.51 (m, 1H); 3.58 (dd, 1H); 3.66 (dd, 1H); 3.90 (dd. 1H); 4.09-4.12 (m, 2H); 4.25 (dd, 1H); 4.77 (d, 2H); 4.83 (s, 1H); 4.88 (s, 1H); 5.13 (m, 1H); 6.03 (m, 1H); 7.28 (dd, 1H); 7.39-7.47 (m, 2H); 7.89 (s, 1H).

Intermediate 56: (5R)-3-[3-Fluoro-4-(1,2,3,6-tetrahydropyridin-4-yl)phenyl]-5-[(4-methyl-1,2,3-triazol-1-yl)methyl]oxazolidin-2-one

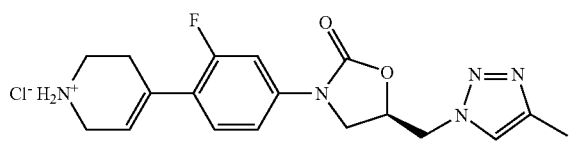

(5R)-3-[4-(1-Benzyl-1,2,3,6-tetrahydropyridin-4-yl)-3-fluorophenyl]-5-[(4-methyl-1H-1,2,3-triazol-1-yl)methyl]-1,3-oxazolidin-2-one (Example 43) (5.13 g, 11.46 mmol) was reacted with diisopropylethylamine (0.40 ml, 2.29 mmol) and 1-chloroethylchloroformate (1.50 ml, 13.76 mmol) as described for Intermediate 53 to give the crude title compound (4.4 g).

EXAMPLE 43

(5R)-3-[4-(1-Benzyl-1,2,3,6-tetrahydropyridin-4-yl)-3-fluorophenyl]-5-[(4-methyl-1,2,3-triazol-1-yl)methyl]oxazolidin-2-one

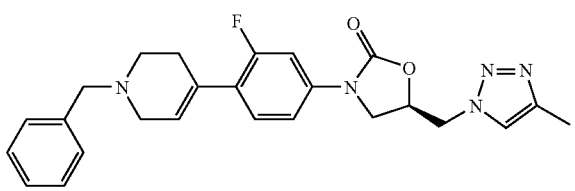

(5S)-5-(Aminomethyl)-3-[4-(1-benzyl-1,2,3,6-tetrahydropyridin-4-yl)-3-flurophenyl]-oxazolidin-2-one (Intermediate 57) (13 g, 34 mmol) was reacted with diisopropylethylamine (23 ml, 136 mmol) and 1,1-dichloroacetone toluenesulfonylhydrazone (15.1 g, 51 mmol) as described for Example 3. Chromatography on silica gel with 0-5% methanol in ethyl acetate gave 5.17 g of the title product.

MS (ESP): 448 (MH$^+$) for $C_{25}H_{26}FN_5O_2$ $^1$H-NMR(500 MHz, DMSO-$d_6$) δ: 2.24 (s, 3H); 2.45 (brs, 2H); 2.64 (dd, 2H); 3.08-3.09 (m, 2H); 3.61 (s, 2H); 3.89 (dd, 1H); 4.06 (dd, 1H); 4.76 (d, 2H); 5.12 (m, 1H); 5.99 (m, 1H); 7.34-7.38 (m, 8H); 7.88 (s, 1H).

Intermediate 57: (5S)-5-(Aminomethyl)-3-[4-(1-Benzyl-1,2,3,6-tetrahydropyridin-4-yl)-3-fluorophenyl]oxazolidin-2-one

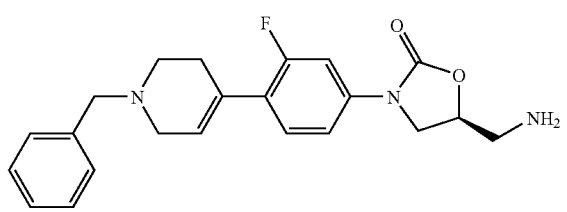

The procedure was identical to that used for Intermediate 54, except (5R)-5-(azidomethyl)-3-[4-(1-benzyl-1,2,3,6-tetrahydropyridin-4-yl)-3-fluorophenyl]-1,3-oxazolidin-2-one (WO 0181350 A1) (21.19 g, 52.00 mmol) was used as starting material. 13 g of the title product was obtained.

MS (ESP): 382 (MH$^+$) for $C_{22}H_{24}FN_3O_2$ $^1$H-NMR(500 MHz. DMSO-$d_6$) δ: 1.84 (s, 2H); 1.93 (s, 2H); 2.46 (br s, 2H); 2.63 (t, 2H); 3.04-3.08 (m, 2H); 3.48 (br s, 2H); 3.85 (dd, 1H); 4.18 (t, 1H); 4.93 (m, 1H); 5.99 (m, 1H); 7.33-7.52 (m, 8H).

EXAMPLE 44

(5R)-3-[4-(1-Benzyl-1,2,3,6-tetrahydropyridin-4-yl) 3,5-difluoro phenyl]-5-[(5-methyl-2H-1,2,3-tetrazol-2-yl)methyl]oxazolidin-2-one

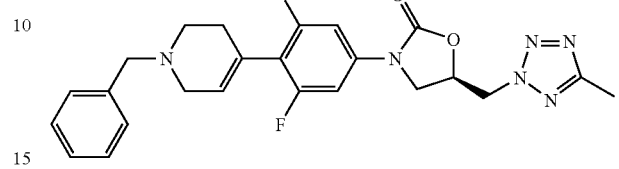

5-Methyl-1H-tetrazole (211 mg, 2.51 mmol) was added to a solution of (5R)-3-[4-(1-benzyl-1,2,3,6-tetrahydropyridin-4-yl)-3,5-difluoro phenyl]-5-(methane-sulfonyloxymethy)-1,3-oxazolidin-2-one (WO 0181350 A1) (1.00 g, 2.09 mmol) in N,N-dimethyformamide (10 ml). Triethylamine (0.35 ml, 2.51 mmol) was added and the mixture was a stirred at room temperature for 24 hours. N,N-dimethylaminopyridine (255 mg, 2.09 mmol) was added and the mixture was heated at 75° C. After an additional 16 hours, additional 5-methyl-1H-tetrazole (100 mg, 1.19 mmol) was added and it was stirred for another day. The mixture was poured into water, extracted with ethyl acetate, the organic phase was dried over magnesium sulfate and concentrated under vacuum. Chromatography on silica gel with 50%-0% hexanes in ethyl acetate gave 288 mg of the title product.

MS (ESP): 467 (MH$^+$) for $C_{24}H_{24}F_2N_6O_2$ $^1$H-NMR(500 MHz, DMSO-$d_6$) δ: 2.34 (brs, 2H); 2.46 (s, 3H); 2.64 (dd, 2H); 3.07 (brs, 2H); 3.61 (s, 2H); 3.91 (dd, 1H); 4.28 (dd, 1H); 5.05-5.17 (m, 2H); 5.28 (m, 1H); 5.82 (brs, 1H); 7.27-7.37 (m, 7H).

The invention claimed is:

1. A compound of the formula (I), or a pharmaceutically acceptable salt, or an in-vivo hydrolysable ester thereof,

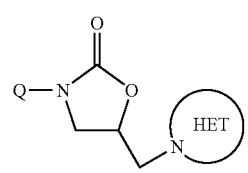

(I)

wherein
—N-HET is selected from structures I(d) to (If):

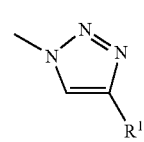

(Id)

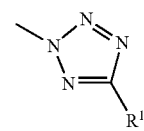

(If)

R¹ is a (1-4C)alkyl group;
Q is selected from Q1 to Q6:

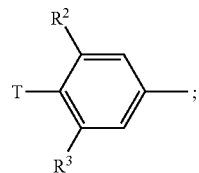
(Q1)

R² and R³ are independently selected from H, F, Cl, CF₃, OMe, SMe, Me and Et;
T is selected from the groups (TA) to (TE);
(TA) T is selected from the following groups:
   (TAa) AR1 or AR3; or
   (TAb) a group of formula (TAb1) to (TAb6):

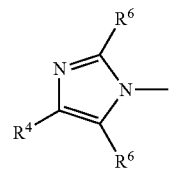
(Tab2)

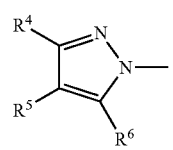
(Tab3)

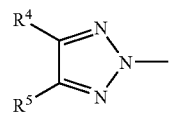
(Tab4)

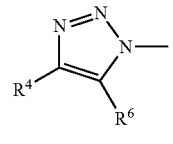
(Tab5)

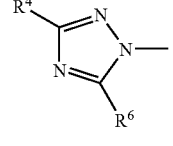
(Tab6)

wherein:
R⁶ is independently selected from hydrogen, (1-4C)alkyl, (1-4C)alkoxycarbonyl, (1-4C)alkanoyl, carbamoyl, and cyano;
R⁴ and R⁵ are independently selected from hydrogen, halo, trifluoromethyl, cyano, azido, nitro, (1-4C)alkoxy, (1-4C)alkylS(O)$_q$— (q is 0, 1, or 2), (1-4C)alkanoyl, (1-4C)alkoxycarbonyl, benzyloxy-(1-4C)alkyl, (2-4C)alkanoylamino, hydroxyimino, (1-4C)alkoxyimino, —CONRcRv, and —NRcRv wherein any (1-4C)alkyl group contained in R⁴ and R⁵ is optionally substituted with up to three substituents independently selected from hydroxy and azido (excluding C1 of an alkoxy group and geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1, or 2), (1-4C)alkylSO₂—NRv-, (1-4C)alkoxycarbonyl, —CONRcRv, and —NRcRv (excluding C1 of an alkoxy group and geminal disubstitution); wherein Rv is hydrogen or (1-4C)alkyl;

R⁴ and R⁵ may further be independently selected from (1-4C)alkyl {optionally substituted with up to three substituents independently selected from hydroxy or azido (excluding geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1, or 2), (1-4C)alkylSO₂—NRv-, (1-4C)alkoxycarbonyl, —CONRcRv, and —NRcRv (excluding geminal disubstitution); wherein Rv is hydrogen or (1-4C)alkyl}; and any (1-4C)alkyl group contained in the immediately preceding optional substituents (when R⁴ and R⁵ are independently (1-4C)alkyl) is itself optionally substituted with up to three substituents independently selected from hydroxy (excluding C1 of an alkoxy group and geminal disubstitution), oxo, trifluoromethyl, cyano, nitro, (1-4C)alkoxy, (2-4C)alkanoyloxy, hydroxyimino, (1-4C)alkoxyimino, (1-4C)alkylS(O)$_q$— (q is 0, 1, or 2), (1-4C)alkylSO₂NRv-, (1-4C)alkoxycarbonyl, —CONRcRv, and —NRcRv (excluding C1 of an alkoxy group and geminal disubstitution); wherein Rv is hydrogen or (1-4C)alkyl; or R⁴ is selected from one of the groups (TAba) to (TAbc) below, or one of R⁴ and R⁵ is selected from the above list of R⁴ and R⁵ values, and the other is selected from one of the groups (TAba) to (TAbc) below:
(TAba) a group of the formula (TAba1)

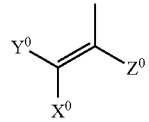
(TAba1)

wherein Z⁰ is hydrogen or (1-4C)alkyl;
X⁰ and Y⁰ are independently selected from hydrogen, (1-4C)alkyl, (1-4C)alkoxycarbonyl, halo, cyano, nitro, (1-4C)alkylS(O)$_q$— (q is 0, 1, or 2), RvRwNSO₂—, trifluoromethyl, pentafluoroethyl, (1-4C)alkanoyl, and —CONRvRw [wherein Rv is hydrogen or (1-4C)alkyl; Rw is hydrogen or (1-4C)alkyl]; or one of X⁰ and Y⁰ is selected from the above list of X⁰ and Y⁰ values, and the other is selected from phenyl, phenylcarbonyl, —S(O)$_q$-phenyl (q is 0, 1, or 2), N-(phenyl)carbamoyl, phenylaminosulfonyl, AR2, (AR2)-CO—, (AR2)-S(O)$_q$— (q is 0, 1, or 2), N-(AR2)carbamoyl, and (AR2)aminosulfonyl; wherein any phenyl group in (TAba) may be optionally substituted with up to three substituents independently selected from (1-4C)alkyl, cyano, trifluoromethyl, nitro, halo, and (1-4C)alkylsulfonyl;
(TAbb) an acetylene of the formula —≡—H or —≡-(1-4C)alkyl;
(TAbc) —X¹—Y¹-AR2, —X¹—Y¹-AR2a, —X¹—Y¹-AR2b, —X¹—Y¹-AR3, —X¹—Y¹-AR3a, or —X¹—Y¹-AR3b;
X¹ is a direct bond or —CH(OH)—; and Y¹ is —(CH₂)$_m$—, —(CH₂)$_n$—NH—(CH₂)$_m$—, —CO—(CH₂)$_m$—, —CONH—(CH₂)$_m$—, —C(=S)NH—(CH₂)$_m$—, or —C(=O)O—(CH₂)$_m$—; or
X¹ is —(CH₂)$_n$— or —CH(Me)-(CH₂)$_m$— and Y¹ is —(CH₂)$_m$—NH—(CH₂)$_m$—, —CO—(CH₂)$_m$—, —CONH—(CH$_2$)$_m$—, —C(═S)NH—(CH$_2$)$_m$—, —C(═O)O—(CH$_2$)$_m$ or —S(O)$_q$—(CH$_2$)$_m$—; or X$^1$ is —CH$_2$O—, —CH$_2$NH—, or —CH$_2$N((1-4C)alkyl)-; and Y$^1$ is —CO(CH$_2$)$_m$—, —CONH—(CH$_2$)$_m$—, or —C(═S)NH—(CH$_2$)$_m$—;

with the following provisos; Y$^1$ is —SO$_2$— when X$^1$ is —CH$_2$NH— or —CH$_2$N((1-4C)alkyl)-, and Y$^1$ is —(CH$_2$)$_m$— when X$^1$ is —CH$_2$O— or —CH$_2$N((1-4C)alkyl)-; wherein n is 1, 2, or 3; m is 0, 1, 2, or 3 and q is 0, 1, or 2; and when Y$^1$ is —(CH$_2$)$_m$—NH—(CH$_2$)$_m$— each m is independently selected from 0, 1, 2, or 3;

(TB) T is selected from halo, formyl, or —NRv$^1$Rw$^1$; or is selected from the following groups: (TBa) R$^{10}$CO—, R$^{10}$S(O)$_q$— (q is 0, 1, or 2) or R$^{10}$CS—wherein R$^{10}$ is selected from the following groups:

(TBaa) -CY1 or CY2;

(TBab) (1-4C)alkoxycarbonyl, trifluoromethyl, —NRvRw, ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, or 2-(AR2)ethenyl; and (TBac) (1-4C)alkyl {optionally substituted with one or more groups each independently selected from hydroxy, (1-4C)alkoxy, (1-4C)alkanoyl, cyano, halo, trifluoromethyl, (1-4C)alkoxycarbonyl, —NRvRw, (1-6C)alkanoylamino, (1-4C)alkoxycarbonylamino, N-(1-4C)alkyl-N-(1-6C)alkanoylamino, (1-4C)alkylS(O)$_q$— (q is 0, 1, or 2), CY1, CY2, AR1, (1-4C)alkylS(O)$_p$NH—, or (1-4C)alkylS(O)$_p$-((1-4C)alkyl)N— (p is 1 or 2)}; wherein Rv is hydrogen or (1-4C)alkyl; Rw is hydrogen or (1-4C)alkyl; Rv$^1$ is hydrogen, (1-4C)alkyl, or (3-8C)cycloalkyl; Rw$^1$ is hydrogen, (1-4C)alkyl, (3-8C)cycloalkyl, formyl, (1-4C)alkyl-CO—, or (1-4C)alkylS(O)$_q$— (q is 1, or 2);

(TC) T is

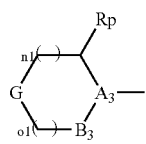

(TC4)

wherein in (TC4): n1 is 1 or 2; o1 is 1 or 2, and n1+o1=2 or 3; >A$_3$-B$_3$— is >C═C(Rr)-, >C(Rq)-CH(Rr)-, or >N—CH$_2$—, and G is —O—, —S—, —SO—, —SO$_2$—, or >N(Rc); Rp is hydrogen, (1-4C)alkyl (other than when such substitution is defined by >A$_3$-B$_3$—), hydroxy, (1-4C)alkoxy, or (1-4C)alkanoyloxy;

wherein in (TC4); m1; n1, and o1 are as defined hereinbefore in (TC):

>A$_3$-B$_3$— is >N—CH$_2$—, and G is >C(R$^{11}$)(R$^{12}$), >C═O, >C—OH, >C—(1-4C)alkoxy, >C═N—OH, >C═N-(1-4C)alkoxy, >C═N—NH-(1-4C)alkyl, >C═N—N((1-4C)alkyl)$_2$ (the last two (1-4C)alkyl groups above in G being optionally substituted with hydroxy), or >C═N—N—CO-(1-4C)alkoxy;

Rq is hydrogen, hydroxy, halo, (1-4C)alkyl, or (1-4C)alkanoyloxy;

Rr is independently hydrogen or (1-4C)alkyl;

R$^{11}$ is hydrogen, (1-4C)alkyl, fluoro(1-4C)alkyl, (1-4C)alkyl-thio-(1-4C)alkyl, or hydroxy-(1-4C)alkyl, and R$^{12}$ is —[C(Rr)(Rr)]$_{m2}$—N(Rr)(Rc) wherein m2 is 0, 1, or 2;

wherein Rc is selected from groups (Rc1) to (Rc5):

(Rc1) (1-6C)alkyl {optionally substituted with one or more (1-4C)alkanoyl groups (including geminal disubstitution) or optionally monosubstituted with cyano, (1-4C)alkoxy,trifluoromethyl, (1-4C)alkoxycarbonyl, phenyl (optionally substituted as AR1), or (1-4C)alkylS(O)$_q$— (q is 0, 1, or 2); or, on any but the first carbon atom of the (1-6C)alkyl chain, optionally substituted with one or more groups (including geminal disubstitution) each independently selected from hydroxy and fluoro, or optionally monosubstituted with oxo or —NRvRw [wherein Rv is hydrogen or (1-4C)alkyl; Rw is hydrogen, (1-4C)alkyl], (1-6C)alkanoylamino, (1-4C)alkoxycarbonylamino, N-(1-4C)alkyl-N-(1-6C)alkanoylamino, (1-4C)alkylS(O)$_p$NH—, or (1-4C)alkylS(O)$_p$-((1-4C)alkyl)N-(p is 1 or 2)};

(Rc2) formyl, R$^{13}$CO—, R$^{13}$SO$_2$—, or R$^{13}$CS— wherein R$^{13}$ is selected from (Rc2a) to (Rc2e):

(Rc2a) AR1, AR2, AR2a, AR2b, AR3, AR3a, AR3b, AR4, AR4a, CY1, or CY2;

(Rc2b) (1-4C)alkoxycarbonyl, trifluoromethyl, —NRvRw [wherein Rv is hydrogen or (1-4C)alkyl; Rw is hydrogen or (1-4C)alkyl], ethenyl, 2-(1-4C)alkylethenyl, 2-cyanoethenyl, 2-cyano-2-((1-4C)alkyl)ethenyl, 2-nitroethenyl, 2-nitro-2-((1-4C)alkyl)ethenyl, 2-((1-4C)alkylaminocarbonyl)ethenyl, 2-((1-4C)alkoxycarbonyl)ethenyl, 2-(AR1)ethenyl, 2-(AR2)ethenyl, or 2-(AR2a)ethenyl;

(Rc2c) (1-10C)alkyl {optionally substituted with one or more groups (including geminal disubstitution) each independently selected from hydroxy, (1-10C)alkoxy, (1-4C)alkoxy-(1-4C)alkoxy, (1-4C)alkoxy-(1-4C)alkoxy-(1-4C)alkoxy, (1-4C)alkanoyl, carboxy, phosphoryl [—O—P(O)(OH)$_2$, and mono- and di-(1-4C)alkoxy derivatives thereof], phophoryl [—O—P(OH)$_2$ and mono- and di-(1-4C)alkoxy derivatives thereof], and amino; or optionally substituted with one group selected from phosphonate[phosphono, —P(O)(OH)$_2$, and mono- and di-(1-4C)alkoxy derivatives thereof], phosphinate [—P(OH)$_2$ and mono- and di-(1-4C)alkoxy derivatives thereof], cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$-((1-4C)alkyl)N—, fluoro(1-4C)alkylS(O)$_p$NH—, fluoro(1-4C)alkylS(O)$_p$((1-4C)alkyl)N—, (1-4C)alkylS(O)$_q$— [the (1-4C)alkyl group of (1-4C)alkylS(O)$_q$— being optionally substituted with one substituent selected from hydroxy, (1-4C)alkoxy, (1-4C)alkanoyl, phosphoryl [—O—P(O)(OH)$_2$, and mono- and di-(1-4C)alkoxy derivatives thereof], phophoryl [—O—P(OH)$_2$ and mono- and di-(1-4C)alkoxy derivatives thereof], amino, cyano, halo, trifluoromethyl, (1-4C)alkoxycarbonyl, (1-4C)alkoxy-(1-4C)alkoxycarbonyl, (1-4C)alkoxy-(1-4C)alkoxy-(1-4C)alkoxycarbonyl, carboxy, (1-4C)alkylamino, di((1-4C)alkyl)amino, (1-6C)alkanoylamino, (1-4C)alkoxycarbonylamino, N-(1-4C)alkyl-N-(1-6C)alkanoylamino, (1-4C)alkylaminocarbonyl, di((1-4C)alkyl)aminocarbonyl, (1-4C)alkylS(O)$_p$NH—, (1-4C)alkylS(O)$_p$-((1-4C)alkyl)N—, (1-4C)

alkylS(O)$_q$—, AR1-S(O)$_q$—, AR2-S(O)$_q$—, AR3-S(O)$_q$—, and AR2a, AR2b, AR3a, and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1, or 2), and AR2a, AR2b, AR3a, and AR3b versions of AR2 and AR3 containing groups};

(Rc2d) $R^{14}C(O)O(1-6C)$alkyl wherein $R^{14}$ is AR1, AR2, (1-4C)alkylamino (the (1-4C)alkyl group being optionally substituted with (1-4C)alkoxycarbonyl, carboxy), benzyloxy-(1-4C)alkyl, or (1-10C)alkyl {optionally substituted as defined for (Rc2c)};

(Rc2e) $R^{15}O$— wherein $R^{15}$ is benzyl, (1-6C)alkyl {optionally substituted as defined for (Rc2c)}, CY1, CY2, or AR2b;

(Rc3) hydrogen, cyano, 2-cyanoethenyl, 2-cyano-2-((1-4C)alkyl)ethenyl, 2-((1-4C)alkylaminocarbonyl)ethenyl, 2-((1-4C)alkoxycarbonyl)ethenyl, 2-nitroethenyl, 2-nitro-2-((1-4C)alkyl)ethenyl, 2-(AR1)ethenyl, 2-(AR2)ethenyl, or (Rc3a)

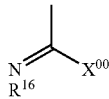
(Rc3a)

wherein $X^{00}$ is —$OR^{17}$, —$SR^{17}$, —$NHR^{17}$, or —$N(R^{17})_2$; $R^{17}$ is hydrogen (when $X^{00}$ is —$NHR^{17}$ or —$N(R^{17})_2$), and $R^{17}$ is (1-4C)alkyl, phenyl, or AR2 (when $X^{00}$ is —$OR^{17}$, —$SR^{17}$, or —$NHR^{17}$); and
$R^{16}$ is cyano, nitro, (1-4C)alkylsulfonyl, (4-7C)cycloalkylsulfonyl, phenylsulfonyl, (1-4C)alkanoyl, or (1-4C)alkoxycarbonyl;

(Rc4) trityl, AR1, AR2, AR2a, AR2b, AR3, AR3a, or AR3b;

(Rc5) RdOC(Re)=CH(C=O)—, RfC(=O)C(=O)—, RgN=C(Rh)C(=O)—, or RiNHC(Rj)=CHC(=O)—, wherein Rd is (1-6C)alkyl; Re is hydrogen or (1-6C)alkyl, or Rd and Re together form a (3-4C)alkylene chain; Rf is hydrogen, (1-6C)alkyl, hydroxy(1-6C)alkyl, (1-6C)alkoxy(1-6C)alkyl, —NRvRw [wherein Rv is hydrogen or (1-4C)alkyl; Rw is hydrogen or (1-4C)alkyl], (1-6C)alkoxy, (1-6C)alkoxy(1-6C)alkoxy, hydroxy(2-6C)alkoxy, (1-4C)alkylamino(2-6C)alkoxy, di-(1-4C)alkylamino(2-6C)alkoxy; Rg is (1-6C)alkyl, hydroxy, or (1-6C)alkoxy; Rh is hydrogen or (1-6C)alkyl; Ri is hydrogen, (1-6C)alkyl, AR1, AR2, AR2a, or AR2b, and Rj is hydrogen or (1-6C)alkyl; wherein AR1 is an optionally substituted phenyl or optionally substituted naphthyl;

AR2 is an optionally substituted 5- or 6-membered, fully unsaturated monocyclic heteroaryl ring containing up to four heteroatoms independently selected from O, N and S (but not containing any O—O, O—Se or S—S bonds), and linked via a ring carbon atom, or a ring nitrogen atom if the ring is not thereby quaternised;

AR2a is a partially hydrogenated version of AR2, linked via a ring carbon atom or linked via a ring nitrogen atom if the ring is not thereby quaternised;

AR2b is a fully hydrogenated version of AR2, linked via a ring carbon atom or linked via a ring nitrogen atom;

AR3 is an optionally substituted 8-, 9- or 10-membered, fully unsaturated bicyclic heteroaryl ring containing up to four heteroatoms independently selected from O, N, and S (but not containing any O—O, O—S, or S—S bonds), and linked via a ring carbon atom in either of the rings comprising the bicyclic system;

AR3a is a partially hydrogenated version of AR3, linked via a ring carbon atom, or linked via a ring nitrogen atom if the ring is not thereby quaternised, in either of the rings comprising the bicyclic system;

AR3b is a fully hydrogenated version of AR3, linked via a ring carbon atom, or linked via a ring nitrogen atom, in either of the rings comprising the bicyclic system;

AR4 is an optionally substituted 13- or 14-membered, fully unsaturated tricyclic heteroaryl ring containing up to four heteroatoms independently selected from O, N, and S (but not containing any O—O, O—S, or S—S bonds), and linked via a ring carbon atom in any of the rings comprising the tricyclic system;

AR4a is a partially hydrogenated version of AR4, linked via a ring carbon atom, or linked via a ring nitrogen atom if the ring is not thereby quaternised, in any of the rings comprising the tricyclic system;

CY1 is an optionally substituted cyclobutyl, cyclopentyl, or cyclohexyl ring;

CY2 is an optionally substituted cyclopentenyl or cyclohexenyl ring;

wherein; optional substituents on AR1, AR2, AR2a, AR2b, AR3, AR3a, AR3b, AR4, AR4a, CY1, and CY2 are (on an available carbon atom) up to three substituents independently selected from (1-4C)alkyl {optionally substituted with substituents selected independently from hydroxy, trifluoromethyl, (1-4C)alkyl S(O)$_q$— (q is 0, 1, or 2), (1-4C)alkoxy, (1-4C)alkoxycarbonyl, cyano, nitro, (1-4C)alkanoylamino, —CONRvRw or —NRvRw}, trifluoromethyl, hydroxy, halo, nitro, cyano, thiol, (1-4C)alkoxy, (1-4C)alkanoyloxy, dimethylaminomethyleneaminocarbonyl, di(N-(1-4C)alkyl)aminomethylimino, carboxy, (1-4C)alkoxycarbonyl, (1-4C)alkanoyl, (1-4C)alkylSO$_2$amino, (2-4C)alkenyl {optionally substituted with carboxy or (1-4C)alkoxycarbonyl}, (2-4C)alkynyl, (1-4C)alkanoylamino, oxo (=O), thioxo (=S), (1-4C)alkanoylamino {the (1-4C)alkanoyl group being optionally substituted with hydroxy}, (1-4C)alkyl S(O)$_q$— (q is 0, 1, or 2) {the (1-4C)alkyl group being optionally substituted with one or more groups independently selected from cyano, hydroxy and (1-4C)alkoxy}, —CONRvRw, or —NRvRw [wherein Rv is hydrogen or (1-4C)alkyl; Rw is hydrogen or (1-4C)alkyl];

and further optional substituents on AR1, AR2, AR2a, AR2b, AR3, AR3a, AR3b, AR4, AR4a, CY1, CY2 (on an available carbon atom), and alkyl groups (unless indicated otherwise) are up to three substituents independently selected from trifluoromethoxy, benzoylamino, benzoyl, phenyl {optionally substituted with up to three substituents independently selected from halo, (1-4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1-4C)alkyl, (1-4C)alkoxyimino(1-4C)alkyl, halo-(1-4C)alkyl, (1-4C)alkanesulfonamido, or —SO$_2$NRvRw [wherein Rv is hydrogen or (1-4C)alkyl; Rw is hydrogen or (1-4C)alkyl]; and optional substituents on AR2, AR2a, AR2b, AR3, AR3a, AR3b, AR4, and AR4a are (on an available nitrogen atom, where such substitution does not result in quaternization) (1-4C)alkyl, (1-4C)alkanoyl {wherein the (1-4C)alkyl and (1-4C)alkanoyl groups are optionally substituted with substituents independently selected from cyano, hydroxy, nitro, trifluoromethyl, (1-4C)alkyl S(O)$_q$— (q is 0, 1, or 2), (1-4C)alkoxy, (1-4C)alkoxycarbonyl, (1-4C)alkanoylamino, —CONRvRw, or —NRvRw [wherein Rv is hydrogen or (1-4C)alkyl; Rw is hydrogen or (1-4C)alkyl]}, (2-4C) alkenyl, (2-4C)alkynyl, (1-4C)alkoxycarbonyl, or oxo (to form an N-oxide).

2. A compound of claim 1, or a pharmaceutically acceptable salt or an in-vivo hydrolysable ester thereof, wherein T is selected from TA and TC.

3. A compound of claim 1, or a pharmaceutically acceptable salt or an in-vivo hydrolysable ester thereof, which is a compound of the formula (IB):

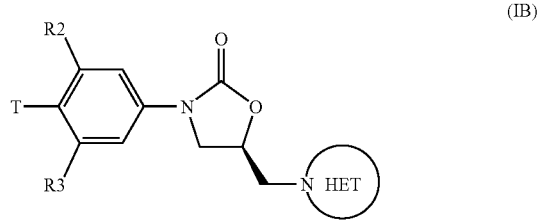

(IB)

wherein —N-HET is 1,2,3-triazol-1-yl or tetrazol-2-yl;
R1 is methyl;
R$^2$ and R$^3$ are independently hydrogen or fluoro; and
T is selected from (TAb2, 3, 5, or 6), (TC5), (TC12a, b or d), and (TC13a).

4. A compound of claim 1, or a pharmaceutically acceptable salt or an in-vivo hydrolysable ester thereof, which is a compound selected from:

(5R)-3-[4-(1 (R,S)-Oxo-3,6-dihydro-2H-thiopyran-4-yl)-3-fluorophenyl]-5-[(4-methyl)-1,2,3-triazol-1-ylmethyl]oxazolidin-2-one;

(5R)-3-[4-(1,1-Dioxo-3,6-dihydro-2H-thiopyran-4-yl)-3-fluorophenyl]-5-[(4-isopropyl)-1,2,3-triazol-1-yl)methyl]oxazolidin-2-one;

(5R)-3-[4-(1,1-Dioxo-3,6-dihydro-2H-thiopyran-4-yl)-3,5-difluorophenyl]-5-[(4-methyl)-1,2,3-triazol-1-yl)methyl]oxazolidin-2-one;

(5R)-3-[4-(1,1-Dioxo-3,6-dihydro-2H-thiopyran-4-yl)-3,5-difluorophenyl]-5-[(4-butyl)-1,2,3-triazol-1-yl)methyl]oxazolidin-2-one;

(5R)-3-[4-(1,1-Dioxo-3,6-dihydro-2H-thiopyran-4-yl)-3-fluorophenyl]-5-[(4-ethyl)-1,2,3-triazol-1-ylmethyl]oxazolidin-2-one;

(5R)-3-[4-(1,1-Dioxo-3,6-dihydro-2H-thiopyran-4-yl)-3-fluorophenyl]-5-[(4-methyl)-1,2,3-triazol-1-ylmethyl]oxazolidin-2-one;

(5R)-3-[3-Fluoro-4-(1-oxo-4-thiomorpholinyl)phenyl]-5-[(4-methyl-1,2,3-triazol-1-ylmethyl]oxazolidin-2-one;

(5R)-3-[4-(1,1-Dioxo-4-thiomorpholinyl)-3-fluorophenyl]-5-[(4-methyl-1,2,3-triazol-1-ylmethyl]oxazolidin-2-one;

(5R)-3-[3,5-Difluoro-4-(1-oxo-4-thiomorpholinyl)phenyl]-5-[4-methyl-1,2,3-triazol-1-ylmethyl]oxazolidin-2-one;

(5R)-3-[4-(1,1-Dioxo-4-thiomorpholinyl)-3,5-difluorophenyl]-5-[(4-methyl-1,2,3-triazol-1-yl)methyl]oxazolidin-2-one;

(5R)-3-[4-(1,1-Dioxo-tetrahydro-2H-thiopyran-4-yl)-3-fluorophenyl]-5-[4-methyl-1,2,3-triazol-1-ylmethyl]oxazolidin-2-one;

(5R)-3-[4-(1,1-Dioxo-2,5-dihydrothien-3-yl)-3-fluorophenyl]-5-[4-methyl-1,2,3-triazol-1-ylmethyl]oxazolidin-2-one;

(5R)-3-[3-Fluoro-4-(4-bromo-1H-imidazol-1-yl)phenyl]-5-[4-methyl-1,2,3-triazol-1-ylmethyl]oxazolidin-2-one;

(5R)-3-[3-Fluoro-4-(4-methyl-1,2,3-triazol-1-yl)phenyl]-5-[(4-methyl-1,2,3-triazol-1-yl)methyl]oxazolidin-2-one;

(5R)-3-[3-Fluoro-4-(3-methyl-1,2,4-triazol-1-yl)phenyl]-5-[(4-methyl-1,2,3-triazol-1-yl)methyl]oxazolidin-2-one;

(5R)-3-[3-Fluoro-4-[(4-carbaldehyde oxime)-imidazol-1-yl]phenyl]-5-[(4-methyl-1,2,3-triazol-1-yl)methyl]oxazolidin-2-one;

(5R)-3-[3-Fluoro-4-[(4-carboxaldehyde)-imidazol-1-yl]phenyl]-5-[(4-pentyl-1,2,3-triazol-1-yl)methyl]oxazolidin-2-one;

(5R)-3-{3-Fluoro-4-[4-(hydroxymethyl)-1H-imidazol-1-yl]phenyl}-5-[(4-methyl-1,2,3-triazol-1-yl)methyl]oxazolidin-2-one;

(5R)-3-[3-Fluoro-4-(4-methyl-1H-imidazol-1-yl)phenyl]-5-[(4-methyl-1,2,3-triazol-1-yl)methyl]oxazolidin-2-one;

(5R)-3-[3-fluoro-4-(1H-imidazol-1-yl)phenyl]-5-[(4-methyl-1,2,3-triazol-1-yl)methyl]oxazolidin-2-one;

(5R)-3-[3-Fluoro-4-(4-carbonitrile-1H-pyrazol-1-yl)phenyl]-5-[(4-methyl-1,2,3-triazol-1-yl)methyl]oxazolidin-2-one;

(5R)-3-[3-fluoro-4-(1-oxo-tetrahydro-2H-thiopyran-4-yl)phenyl]-5-[(4-methyl-1,2,3-triazol-1-yl)methyl]oxazolidin-2-one, E-Isomer;

(5R)-3-[3-Fluoro-4-(1-oxo-tetrahydro-2H-thiopyran-4-yl)phenyl]-5-[(4-methyl-1,2,3-triazol-1-yl)methyl]-1,3-oxazolidin-2-one, Z-Isomer;

(5R)-3-[4-(Tetrahydro-2H-thiopyran-4-yl)-3,5-difluorophenyl]-5-[(4-methyl-1,2,3-triazol-1-yl)methyl]oxazolidin-2-one;

(5R)-3-[4-(1,1-Dioxo-tetrahydro-2H-thiopyran-4-yl)-3,5-difluorophenyl]-5-[(4-methyl-1,2,3-triazol-1-yl)methyl]oxazolidin-2-one;

(5R)-3-[3,5-Difluoro-4-(1-oxo-tetrahydro-2H-thiopyran-4-yl)phenyl]-5-[(4-methyl-1,2,3-triazol-1-yl)methyl]-oxazolidin-2-one, E-Isomer;

(5R)-3-[3,5-Difluoro-4-(1-oxo-tetrahydro-2H-thiopyran-4-yl)phenyl]-5-[(4-methyl-1,2,3-triazol-1-yl)methyl]oxazolidin-2-one, Z-Isomer;

(5R)-3-[4-(1,1-Dioxo-3,6-dihydro-2H-thiopyran-4-yl)-3,5-difluorophenyl]-5-[(5-methyl-2H-tetrazol-2-yl)methyl]oxazolidin-2-one;

(5R)-3-[4-(1,1-Dioxo-3,6-dihydro-2H-thiopyran-4-yl)-3,5-difluorophenyl]-5-[(5-Ethyl-2H-tetrazol-2-yl)methyl]oxazolidin-2-one;

(5R)-3-[3-Fluoro-4-(4-carbonitrile-1H-pyrazol-1-yl)phenyl]-5-[(5-methyl-2H-tetrazol-2-yl)methyl]oxazolidin-2-one;

(5R)-3-[4-(1,1-Dioxo-3,6-dihydro-2H-thiopyran-4-yl)-3,5-difluorophenyl]-5-[(5-propyl-2H-tetrazol-2-yl)methyl]oxazolidin-2-one;

(5R)-3-[3-fluoro-4-(4-methyl-1H-1,2,3-triazol-1-yl)phenyl]-5-[(5-methyl-2H-tetrazol-2-yl)methyl]oxazolidin-2-one;

(5R)-3-{3-Fluoro-4-[4-(methylthio)-1H-1,2,3-triazol-1-yl]phenyl}-5-[(5-methyl-2H-tetrazol-2-yl)methyl]oxazolidin-2-one;

(5R)-3-[4-(Tetrahydro-2H-thiopyran-4-yl)-3,5-difluorophenyl]-5-[(5-methyl-2H-tetrazol-2-yl)methyl]oxazolidin-2-one;

(5R)-3-[4-(1,1-dioxo-tetrahydro-2H-thiopyran-4-yl)-3,5-difluorophenyl]-5-[(5-methyl-2H-tetrazol-2-yl)methyl]oxazolidin-2-one;

(5R)-3-[4-(1-Oxo-tetrahydro-2H-thiopyran-4-yl)-3,5-difluorophenyl]-5-[(5-methyl-2H-tetrazol-2-yl)methyl]oxazolidin-2-one, Z isomer;

(5R)-3-[3-Fluoro-4-(4-methyl-1H-imidazol-1-yl)phenyl]-5-[(5-methyl-2H-tetrazol-2-yl)methyl]oxazolidin-2-one;

(5R)-3-[3,5-Difluoro-4-(1-glycoloyl-1,2,3,6-tetrahydropyridin-4-yl)phenyl]-5-[(4-methyl-1,2,3-triazol-1-yl)methyl]oxazolidin-2-one;

(5R)-3-[4-(1-Benzyl-1,2,3,6-tetrahydropyridin-4-yl)-3,5-difluorophenyl]-5-[(4-methyl-1,2,3-triazol-1-yl)methyl]oxazolidin-2-one;

(5R)-3-(4-{1-[(2S)-2,3-Dihydroxypropanoyl]-1,2,3,6-tetrahydropyridin-4-yl}-3,5-difluorophenyl)-5-[(4-methyl-1,2,3-triazol-1-yl)methyl]oxazolidin-2-one;

(5R)-3-[3-Fluoro-4-(1-glycoloyl-1,2,3,6-tetrahydropyridin-4-yl)phenyl]-5-[(4-methyl-1,2,3-triazol-1-yl)methyl]oxazolidin-2-one;

(5R)-3-[4-(1-Acetoxyacetyl-1,2,3,6-tetrahydropyridin-4-yl)-3-fluorophenyl]-5-[(4-methyl-1,2,3-triazol-1-yl)methyl]oxazolidin-2-one;

(5R)-3-[4-(1-Benzyl-1,2,3,6-tetrahydropyridin-4-yl)-3-fluorophenyl]-5-[(4-methyl-1,2,3-triazol-1-yl)methyl]oxazolidin-2-one; and (5R)-3-[4-(1-Benzyl-1,2,3,6-tetrahydropyridin-4-yl) 3,5-difluoro phenyl]-5-[(5-methyl-2H-1,2,3-tetrazol-2-yl)methyl]oxazolidin-2-one.

5. A method for treating a bacterial infection, comprising administering to a warm blooded animal an effective amount of a compound of claim 1, or a pharmaceutically acceptable salt or in-vivo hydrolysable ester thereof to treat the bacterial infection, wherein the bacterial infection is caused by bacteria selected from the group consisting of Staphylococci, Enterococci, Streptococci, *Haemophilus, Moraxella,* and *Chlamydiae.*

6. A pharmaceutical composition which comprises a compound of claim 1, or a pharmaceutically acceptable salt or an in-vivo hydrolysable ester thereof, and a pharmaceutically acceptable diluent or carrier.

7. A process for the preparation of a compound of claim 1 or pharmaceutically acceptable salt or in-vivo hydrolysable ester thereof, which process comprises any one of processes (a) to (g);
(a) modifying a substituent in, or introducing a new substituent into, the substituent group R1 of HET of another compound of formula (I);
(b) reaction of a compound of formula (II):

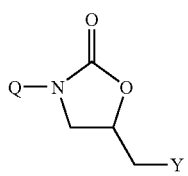

(II)

wherein Y is a displaceable group with a compound of the formula (III):

HET (III)

wherein HET (of formula (Ia) to (If), already substituted and optionally protected) is HET-H free-base form or HET-anion formed from the free base form; or
(c) reaction of a compound of the formula (IV):

Q-Z (IV)

wherein Z is an isocyanate, amine, or urethane group with an epoxide of the formula (V); or with a related compound of formula (VI) where
the hydroxy group at the internal C-atom is conventionally protected and where the leaving group Y at the terminal C-atom is a conventional leaving group; or

(V)

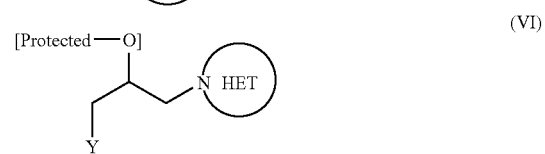

(VI)

(d) (i) coupling, using catalysis by transition metals such as palladium(0), of a compound of formula (VII):

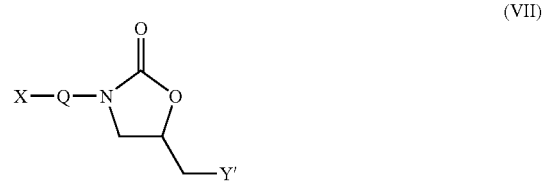

(VII)

wherein Y' is a group HET as hereinbefore defined, X is a replaceable substituent;
with a compound of the formula (VIII), or an analogue thereof, which is suitable to give a T substituent as defined by (TA)-(TE), in which the link is via an sp² carbon atom (D=CH=C-Lg where Lg is a leaving group; or as in the case of reactions carried out under Heck reaction conditions Lg may also be hydrogen) or in which the link is via an N atom (D=NH)

(VIII)

where T₁ and T₂ may be the same or different or may together with D form a ring of type T;
(d) (ii) by coupling, using catalysis by transition metals such as palladium(0), of a compound of formula (VIIA):

(VIIA)

wherein Y' is a group HET as hereinbefore defined, with a compound [Aryl]-X, where X is a replaceable substituent;

(e) Where N-HET is 1,2,3-triazole by cycloaddition via the azide (wherein Y in (II) is azide), with a substituted acetylene or a masked acetylene;

(f) Where N-HET is 1,2,3-triazole by reaction of a compound of formula (II) where Y=NH$_2$ (primary amine) with a compound of formula (IX), namely the arenesulfonylhydrazone of a methyl ketone that is further geminally substituted on the methyl group with two substituents (Y' and Y") capable of being eliminated from this initial, and the intermediate, substituted hydrazones as HY' and HY" (or as conjugate bases thereof);

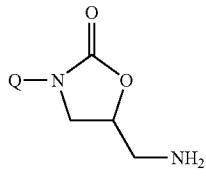

(II: Y = NH$_2$)

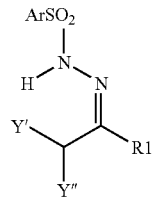

(IX)

(g) where N-HET is 1,2,3-triazole regioselective synthesis may be carried out by cycloaddition via the azide (wherein Y in (II) is azide) with a terminal alkyne using Cu(I) catalysis to give 4-substituted 1,2,3-triazoles;

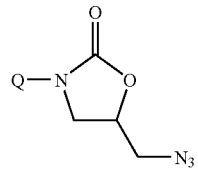

(II : Y = N$_3$)

and thereafter if necessary:
(i) removing any protecting groups;
(ii) forming a pharmaceutically acceptable salt; and/or
(iii) forming an in-vivo hydrolysable ester.

* * * * *